United States Patent
Witek et al.

(10) Patent No.: US 11,261,458 B2
(45) Date of Patent: Mar. 1, 2022

(54) *POTYVIRUS* RESISTANCE GENES AND METHODS OF USE

(71) Applicant: TWO BLADES FOUNDATION, Evanston, IL (US)

(72) Inventors: Kamil Witek, Norwich (GB); Marta Grech-Baran, Warsaw (PL); Jacek Hennig, Warsaw (PL); Jonathan D. G. Jones, Norwich (GB); Waldemar Marczewski, Mlochów (PL); Katarzyna Szajko, Grójec (PL)

(*) Notice: Subject to any disclaimer, the term of this patent is extended or adjusted under 35 U.S.C. 154(b) by 0 days.

(21) Appl. No.: 16/634,384

(22) PCT Filed: Jul. 27, 2018

(86) PCT No.: PCT/US2018/044108
§ 371 (c)(1),
(2) Date: Jan. 27, 2020

(87) PCT Pub. No.: WO2019/023587
PCT Pub. Date: Jan. 31, 2019

(65) Prior Publication Data
US 2021/0115465 A1    Apr. 22, 2021

Related U.S. Application Data

(60) Provisional application No. 62/538,020, filed on Jul. 28, 2017.

(51) Int. Cl.
*C12N 15/82*    (2006.01)
(52) U.S. Cl.
CPC ................. *C12N 15/8283* (2013.01)
(58) Field of Classification Search
None
See application file for complete search history.

(56) References Cited

U.S. PATENT DOCUMENTS

2012/0102589 A1    4/2012    Rommens et al.

OTHER PUBLICATIONS

International Search Report in PCT/US2018/044108, dated Oct. 9, 2018.
Written Opinion of the International Searching Authority, in PCT/US2018/044108, dated Oct. 9, 2018.
Cernak Istvan et al, "Development of a locus-specific marker and localization of the Ry(sto) gene based on linkage to a catalase gene on chromosome XII in the tetrapioid potato genome," Breeding Science, vol. 58, No. 3, pp. 309-314, Sep. 3, 2008 (Sep. 2008).
Ye-Su Song et al, "Development of STS Markers for Selection of Extreme Resistance (RY sto ) to PVY and Maternal Pedigree Analysis of Extremely Resistant Cultivars," American Journal of Potato Research, vol. 85, No. 2, pp. 159-170, Apr. 1, 2008 (Apr. 1, 2008).
Xianzhou Nie et al, "Detection of molecular markers linked to Ry genes in potato germplasm for marker-assisted selection for extreme resistance to PVY in AAFC's potato breeding program," Canadian Journal of Plant Science, vol. 96, No. 5, pp. 737-742, Oct. 1, 2016 (Oct. 1, 2016).
Valkonen J P T et al, "Evidence for utility of the same PCR-based markers for selection of extreme resistance to Potato virus Y controlled by Ry(sto) of Solanum stoloniferum derived from different sources," Annals of Applied Biology, vol. 152, No. 1, pp. 121-130, 2008.
Flis Bogdan et al, "The Ry-fsto gene from Solanum stoloniferum for extreme resistant to Potato vims Y maps to potato chromosome XII and is diagnosed by PCR marker GP122718 in PVY resistant potato cultivars," Molecular Breeding, vol. 15, No. 1, pp. 95-101, Jan. 2005 (Jan. 2005).
Database NCBI accession No. XP_006349899, "Predicted: putative late blight resistance protein homolog R1B-23," XP002784902, Jan. 5, 2016 (Jan. 5, 2016).
Database NCBI accession No. XP_006367311, "Predicted: TMV resistance protein N-like [Solanum tuberosum]," XP002784901, Jan. 5, 2016 (Jan. 5, 2016).

*Primary Examiner* — Elizabeth F McElwain
(74) *Attorney, Agent, or Firm* — Williams Mullen; David M. Saravitz

(57) ABSTRACT

Compositions and methods and for enhancing the resistance of plants to plant diseases caused by potyviruses are provided. The compositions comprise nucleic acid molecules encoding resistance (R) gene products and variants thereof and plants, seeds, and plant cells comprising such nucleic acid molecules. The methods for enhancing the resistance of a plant to plant disease caused by a potyvirus comprise introducing a nucleic acid molecule encoding an R gene product into a plant cell. Additionally provided are methods for using the plants in agriculture to limit plant disease.

Figures 1A, 1B:
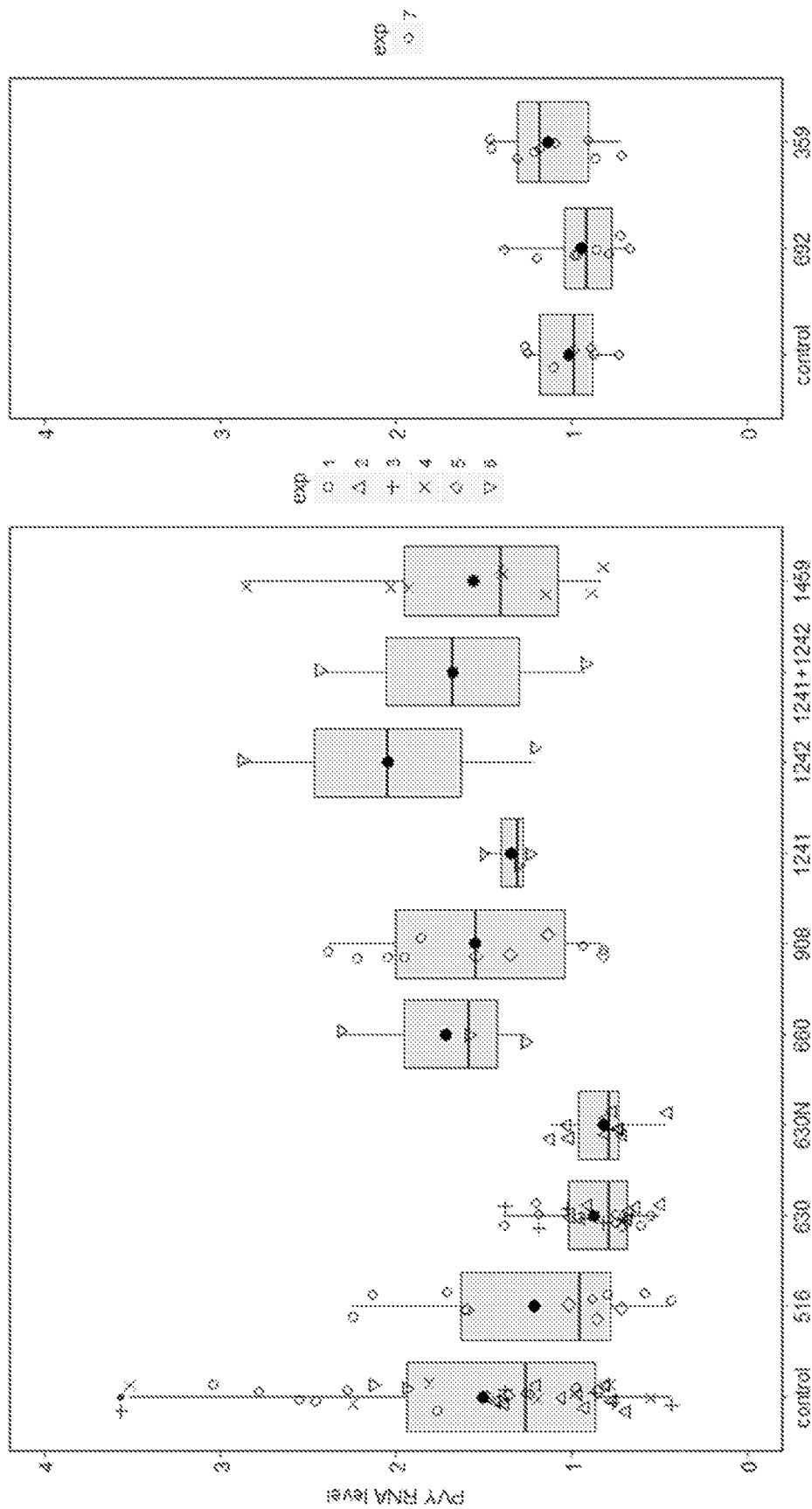

17 Claims, 12 Drawing Sheets
Specification includes a Sequence Listing.

POTYVIRUS RESISTANCE GENES AND METHODS OF USE

CROSS-REFERENCE TO RELATED APPLICATIONS

This application is the U.S. National Stage of International Application PCT/US2018/044108, filed Jul. 27, 2018, which designates the U.S. and was published by the International Bureau in English on Jan. 31, 2019, and which claims the benefit of U.S. Provisional Patent Application No. 62/538,020, filed Jul. 28, 2017, all of which are hereby incorporated herein in their entirety by reference.

REFERENCE TO A SEQUENCE LISTING SUBMITTED AS A TEXT FILE

The official copy of the sequence listing is submitted electronically via EFS-Web as an ASCII formatted sequence listing with a file named 070294-0146SEQLST.TXT, created on Jul. 24, 2018, and having a size of 105 kilobytes, and is filed concurrently with the specification. The sequence listing contained in this ASCII formatted document is part of the specification and is herein incorporated by reference in its entirety.

FIELD OF THE INVENTION

The present invention relates to the fields of gene isolation and plant improvement, particularly to enhancing the resistance of plants to plant disease through the use of disease resistance genes.

BACKGROUND OF THE INVENTION

Potato virus Y (PVY), a member of the Potyvirus genus (Potyviridae family), is the most economically important virus infecting potatoes, with tuber yield and quality losses reaching 85% (Valkonen (2007) "Potato viruses: economical losses and biotechnological potential," in *Potato biology and biotechnology*, Viola et al., eds., Elsevier, San Diego, pp 619-641). PVY exists in nature as several distinct strains: the common (ordinary) group $PVY^O$, the stipple streak group $PVY^C$, a group of $PVY^Z$ strains, the tobacco veinal necrosis group $PVY^N$, and the tuber necrosis strain group $PVY^{NTN}$. Additionally, a new group that does not induce tobacco veinal necrosis was identified and named $PVY^E$ (Singh et al. (2008) *Arch. Virol.* 153: 1-13).

PVY is easily transmitted mechanically and can also be transmitted by over 40 aphid species in a non-persistent manner (Brunt (2001) "Potyviruses," in *Virus and virus-like diseases of potatoes and production of seed-potatoes*, Loebenstein et al., eds., Kluwer Academic Publishers, London, pp. 77-84). Virus strains $PVY^O$ and $PVY^C$ usually induce mild symptoms of infection, e.g. leaf mosaic lesions, crinkling, leaf drop and dwarfing, while leaf symptoms of $PVY^N$ and $PVY^{N\text{-}Wilga}$ infection are barely noticeable. In addition to severe leaf symptoms, $PVY^{NTN}$ infection leads to potato tuber necrotic ringspot disease (PTNRD) (Schubert et al. (2007) *J. Virol. Methods* 140: 66-74).

The pathogenicity of PVY is not limited to potato; other solanaceous crops such as pepper (*Capsicum* spp.), tomato (*Solanum lycopersicum* L.) and tobacco (*Nicotiana tabacum* L.) are affected by PVY as well. Potato and pepper as hosts seem to be selective for PVY strains, while it seems that tomato and tobacco can be infected with most PVY strains from potato and pepper (Aramburu (2006) *Plant Pathol.* 115:247-58).

Breeding of resistant cultivars is one of the most effective strategies to achieve protection against PVY (Świeżyński (1994) "Inheritance of resistance to viruses," in *Potato Genetics*, Bradshaw and and Mackay, eds., CAB International, Wallingford, UK, pp. 339-363). In potato, there are two main types of resistance to PVY, the hypersensitive response (HR) and extreme resistance (ER) (Valkonen et al. (1996) *Plant Breed.* 115:433-38). The hypersensitive response to PVY is usually strain specific and may result in a range of necrotic reactions both in locally and systemically infected leaves (Valkonen et al. (1998) *Phytopathology* 88:1073-77). Genes conferring HR (Ny genes) are widely distributed in potato cultivars (Ruiz de Galarreta et al. (1998) *Potato Res.* 41:57-68). In some cases, however, hypersensitivity may be ineffective for restriction of PVY in plants (Vidal et al. (2002) *Mol. Plant Microbe Interact.* 15:717-27). ER genes are broad-spectrum and confer strong and durable resistance, characterized by lack of visible symptoms after inoculation (Flis et al. (2005)*Mol. Breed.* 15:95-101).

Resistance genes against PVY infection had been introduced into potato cultivars from many sources (Table 1), as was summarized by van Eck et al. ((2017) *Theor. Appl. Genet.* 130:515-528)). Some of these genes, for example Ry from *Solanum stoloniferum* (also referred to as "$Ry_{sto}$"), were introduced into multiple European cultivars and were shown to confer durable resistance against multiple PVY strains. $Ry_{sto}$ and $Ry\text{-}f_{sto}$, another PVY resistance gene from *S. stoloniferum*, are widely used in the breeding of potato varieties for resistance to PVY (Flis et al. (2005) *Mol. Breed.* 15:95-101; Song et al. (2005) *Theor. Appl. Genet.* 111:879-887).

TABLE 1

Resistance Loci Against PVY Infection

| Locus | Chromosome | Ancestral germplasm | References |
|---|---|---|---|
| Ncspl | 4 | S. sparsipilum | Moury et al. (2011) Mol. Plant-Microbe Interact. 24: 787-797 |
| Nytbr | 4 | S. tuberosum | Celebi-Toprak et al. (2002) Theor. Appl. Genet. 104: 669-674 |
| $Ry_{chc}$ | 9 | S. chacoense | Hosaka et al. (2001) Am. J. Potato Res. 78: 191-196 Sato et al. (2006) Euphytica 149: 367-372 |
| Ny-1 | 9 | cv. Rywal | Szajko et al. (2008) Theor. Appl. Genet. 116: 297-303 |
| Ny-Smira | 9 | cv. Sarpo Mira | Tomczyńska et al. (2014) Mol. Breed. 34: 471-480 |
| $Ry_{adg}$ | 11 | group andigena | Hämäläinen et al. (1997) Theor. Appl. Genet. 94: 192-197 Hämäläinen et al. (1998) Theor. Appl. Genet. 96: 1036-1043 |
| Ny-2 | 11 | cv. Romula | Szajko et al. (2014) Mol. Breed. 34: 267-271 |
| $Ry_{sto}$ | 11 | S. stoloniferum | Brigneti et al. (1997) Theor. Appl. Genet. 94: 198-203 |
| $Ry\text{-}f_{sto}$ | 12 | S. stoloniferum | Flis et al. (2005) Mol. Breed. 15: 95-101 Song et al. (2005) Theor. Appl. Genet. 111: 879-887 |

There is a high demand for new solanaceous crop plant varieties comprising strong and durable resistance genes against PVY to limit the economic losses caused by this devastating plant pathogen. However, producing such new solanaceous crop plant varieties by traditional plant breeding methods can be both laborious and time consuming. More rapid methods involving the introduction of cloned resistance genes into existing elite germplasm via genetic engineering can be used to produce new solanaceous crop plant varieties, but such rapid methods depend on the availability of cloned resistance genes. Unfortunately, none of the genes conferring effective HR or ER-type of resistance have yet been reported to have been cloned (Vidal et al. (2002) *Mol. Plant Microbe Interact.* 15:717-27; Kim et al. (2017) New Phytol. 213:886-899). The available of cloned resistance genes against PVY would enable plant breeders to produce more rapidly new solanaceous crop plant varieties comprising, not only multiple resistance genes against multiple strains of PVY, but also one or more resistance genes against other important plant pathogens such as, for example, *Phytophthora infestans*, the causal agent of late blight of potatoes and tomatoes.

BRIEF SUMMARY OF THE INVENTION

The present invention provides nucleic acid molecules of resistance (R) genes that are capable of conferring to a plant resistance to at least one potyvirus that is known to cause a plant disease in the plant. In certain embodiments of the invention, the nucleic acid molecules of R genes are capable of conferring to a plant, particularly a solanaceous plant, resistance to at least one strain of Potato virus Y (PVY) and/or Potato virus A (PVA) that is known to cause a plant disease in the plant. Preferably, such nucleic acid molecules are capable of conferring to a plant enhanced resistance to multiple strains of PVY and/or PVA including, for example, at least two, three, four, five, or more strains of PVY and/or PVA. In one embodiment, the present invention provides nucleic acid molecules of an R gene, which is referred to herein as c630, and its variants including, for example, orthologs, and other naturally and non-naturally occurring variants of c630. In another embodiment, the present invention provides nucleic acid molecules of an R gene, which is referred to herein as c516, and its variants including, for example, orthologs and other naturally and non-naturally occurring variants of c516.

The present invention further provides plants, plant cells, and seeds comprising in their genomes one or more heterologous polynucleotides of the invention. The heterologous polynucleotides comprise a nucleotide sequence encoding a resistance (R) protein of the present invention. Such R proteins are encoded by the R genes of the present invention, particularly c630 and c516, their respective orthologs and other naturally and non-naturally occurring variants of c630 and c516. In a preferred embodiment, the plants and seeds are transgenic solanaceous plants and seeds that have been transformed with one or more heterologous polynucleotides of the invention. Preferably, such solanaceous plants comprise enhanced resistance to at least one strain of PVY and/or PVA that is known to cause a plant disease in a solanaceous plant, when compared to the resistance of a control plant that does not comprise the heterologous polynucleotide. More preferably, such solanaceous plants comprise enhanced resistance to two, three, four, or more strains of PVY and/or PVA that a known to cause a plant disease in a solanaceous plant, when compared to the resistance of a control plant that does not comprise the heterologous polynucleotide. Solanaceous plants of the invention include, but are not limited to, domesticated solanaceous plants including, for example, domesticated varieties of potato, tomato, pepper, and tobacco.

The present invention provides methods for enhancing the resistance of a plant to at least one potyvirus that is known to cause a plant disease in the plant. In certain embodiments of the invention, the methods involve enhancing the resistance of a plant, particularly a solanaceous plant, to a plant disease caused by at least one strain of PVY and/or PVA. Such methods comprise introducing into at least one plant cell a heterologous polynucleotide comprising a nucleotide sequence of an R gene of the present invention. Preferably, the heterologous polynucleotide or part thereof is stably incorporated into the genome of the plant cell. The methods can optionally further comprise regenerating the plant cell into a plant that comprises in its genome the heterologous polynucleotide. Preferably, such a plant comprises enhanced resistance to a plant disease caused by at least one potyvirus, particularly at least one strain of PVY and/or PVA, relative to the resistance of a control plant not comprising the heterologous polynucleotide. More preferably, such a plant comprises enhanced resistance to plant disease(s) caused by at least two, three, four, five, or more strains of PVY and/or PVA, relative to the resistance of a control plant not comprising the heterologous polynucleotide. In the certain embodiments, the plant produced by the methods of the present invention comprises enhanced resistance to at least one potyvirus that is not PVY or PVA. In the certain embodiments, the plant produced by the methods of the present invention comprises enhanced resistance to at least one least one strain of PVY and/or at least one least one strain of PVA, and further comprises enhanced resistance to at least one additional potyvirus, wherein the additional potyvirus is not PVY or PVA.

The present invention additionally provides methods for identifying a solanaceous plant that comprises an R gene for a plant disease caused by at least one strain of PVY and/or PVA. The methods comprise detecting in the solanaceous plant the presence of c630, c516, or both c630 and c516.

Methods of using the plants of the present invention in agricultural crop production to limit plant disease caused by at least one strain of PVY, at least one strain of PVA, and/or at least one other potyvirus are also provided. The methods comprise planting a plant (e.g. a seedling), a tuber, or a seed of the present invention, wherein the plant, tuber, or seed comprises at least one R gene nucleotide sequence of the present invention. The methods further comprise growing a plant under conditions favorable for the growth and development of the plant, and optionally harvesting at least one fruit, tuber, leaf, or seed from the plant.

Additionally provided are plants, plant parts, seeds, plant cells, other host cells, expression cassettes, and vectors comprising one or more of the nucleic acid molecules of the present invention.

BRIEF DESCRIPTION OF THE DRAWINGS

FIGS. 1A-1B are graphs illustrating levels of PVY mRNA after infection of *N. benthamiana* leaves transiently expressing candidate contigs. For the results shown in FIG. 1A, the third leaves of *N. benthamiana* plants were separately infiltrated with the vector pICSLUS0003::35S overexpressing candidate contig c124_1, c124_2, c516, c630, c908, c1459 or c660, or with an empty vector (negative control). Twenty-four hours later the leaves were inoculated with $PVY^{NTN}$ (isolate NIB-NTN). Seven days after the PVY inoculation, mRNA was isolated from upper, non-inoculated leaves and PVY mRNA levels were quantified with quantitative RT-PCR. Two constructs, c630 and c516, showed significant reduction of viral mRNA levels. Expression of candidate c630 from pICSLUS0001 vector under control of native regulatory elements, resulted in a similar reduction of viral mRNA level as for pICSLUS0003::35S::c630 construct. For the results shown in FIG. 1B, the experiment was performed as described above for FIG. 1A with two additional candidate genes, c359 and c692, and with an empty vector as a negative control. There was no statistically significant difference in viral mRNA levels between these candidate contigs and the negative control. For both FIGS. 1A and 1B, the experiments were performed on 3-10 plants for each construct and the points on the graph represent mRNA levels in independent plants. For some constructs, the experiment was repeated two to three times; different point shapes on the graph represent plants from different experiments.

Figure 2:
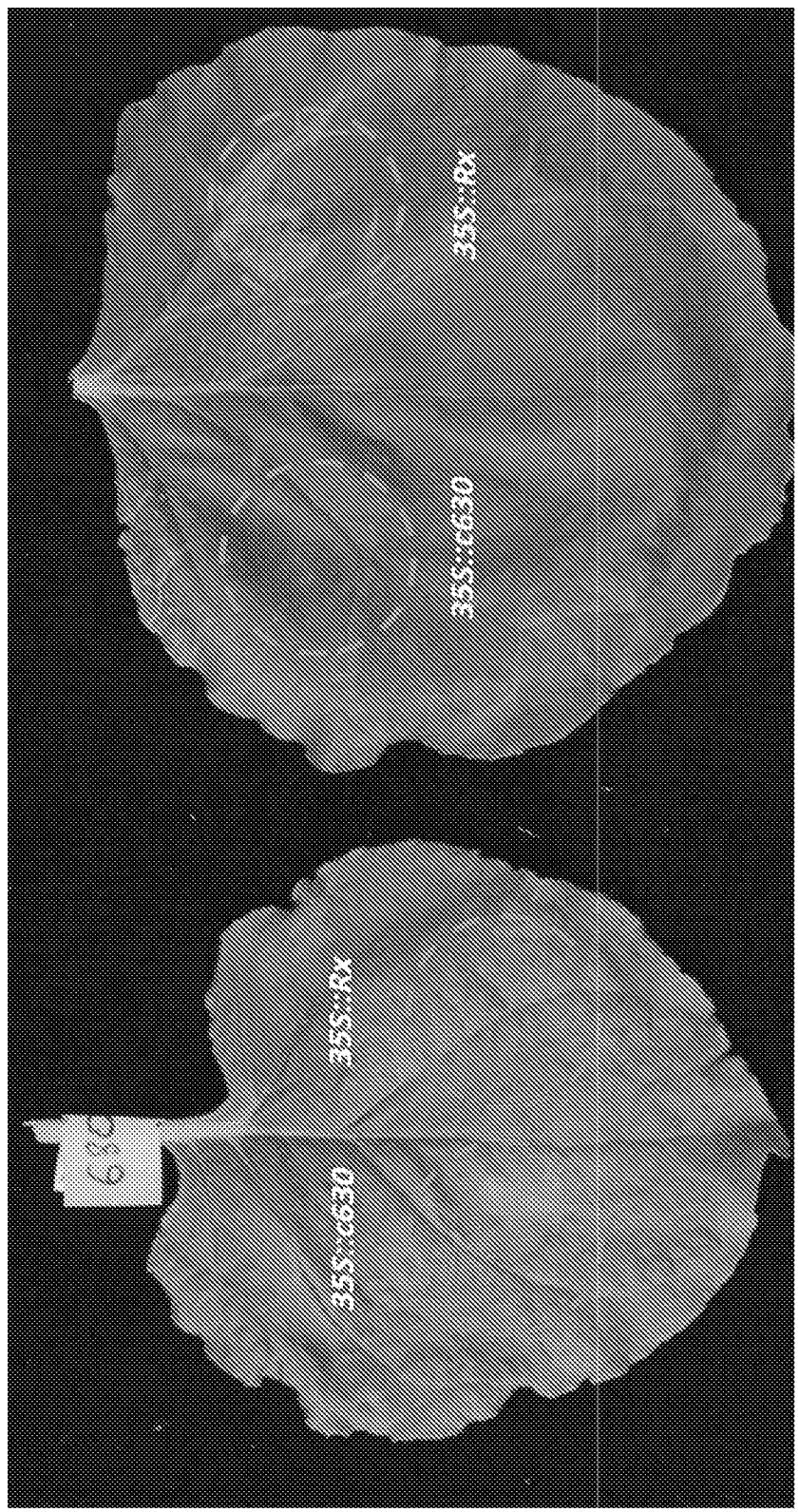

FIG. 2. is a photographic illustration of the HR developed after infiltration of c630 into *N. benthamiana* plants systemically infected with PVY. Four-week-old *N. benthamiana* plants systemically infected with PVY$^{NTN}$ (NIB-NTN, left) or PVX (right) were infiltrated with the vector pICSLUS0003::35S overexpressing c630 or c516 (not shown) candidate genes, or Rx control gene. Only the infiltration of c630 into PVY-infected plants resulted in a strong HR at 3 days post inoculation (dpi), similar to the one in the control experiment in which Rx was infiltrated into PVX-carrying plants (right). The photographs were taken at 5 dpi.

Figure 3:
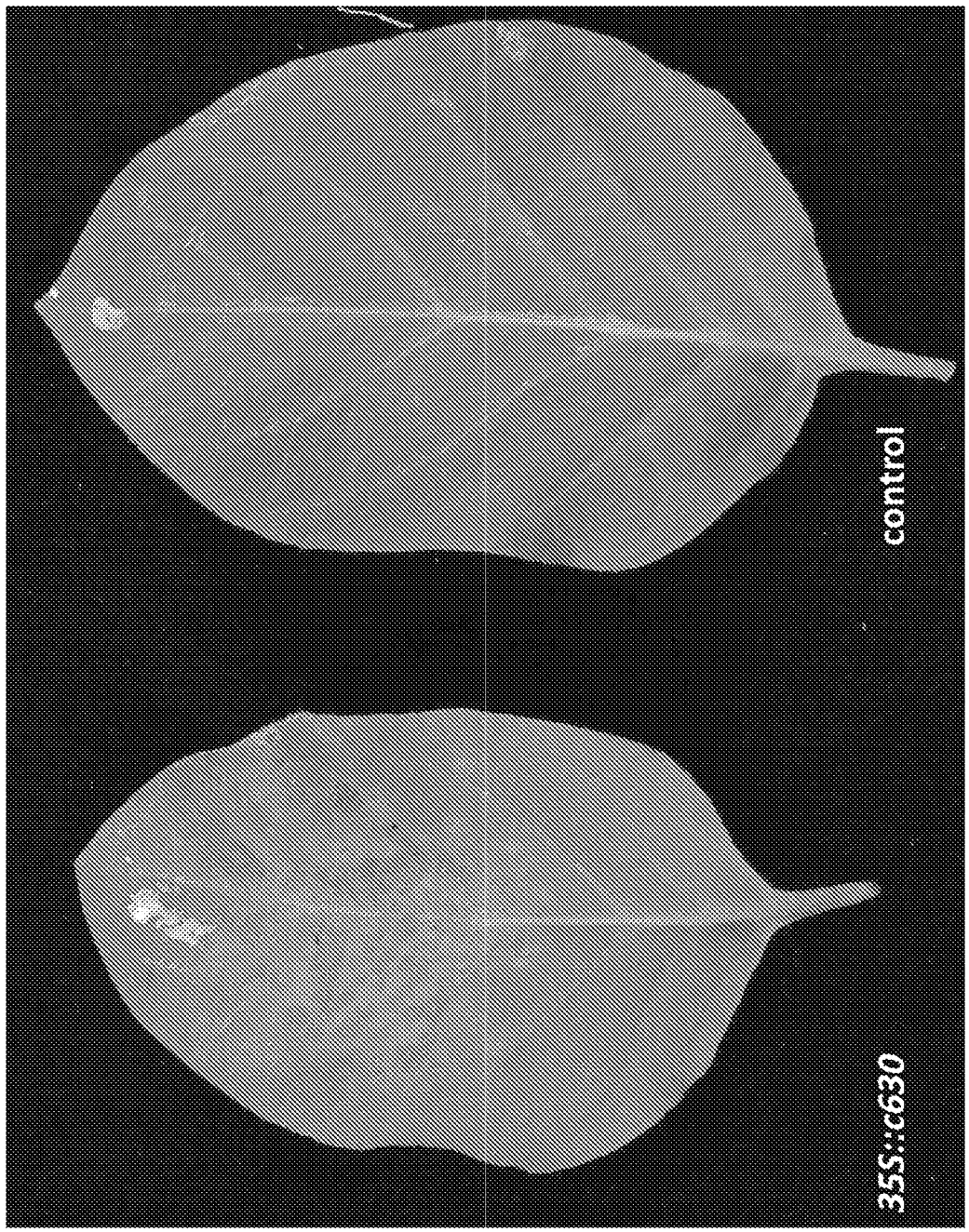

FIG. 3. is a photographic illustration of the HR response after PVY inoculation in stable transgenic *N. tabacum* plants transformed with 35S::c630. Seven-week-old *N. tabacum* 35S transgenic and wild-type (WT) control, *N. tabacum* plants were inoculated with PVY$^{NTN}$ (isolate NIB-NTN). The HR was observed only on *N. tabacum*/35S:c630 inoculated leaves at 3 dpi. WT control plants remained symptomless. The photographs were taken at 7 dpi.

Figure 4A:
Figure 4B:

FIGS. 4A-4B are photographic illustrations of systemic, non-inoculated leaves of *N. tabacum* plants after 14 days after inoculation with PVY. FIG. 4A shows leaves from *N. tabacum* plants transformed with 35S::c630. FIG. 4B shows leaves from WT control, *N. tabacum* plants. Seven-week-old *N. tabacum* 35S::c630 transgenic plants and WT control, *N. tabacum* plants were inoculated with PVY$^{NTN}$ (isolate NIB-NTN). While typical symptoms of PVY infection were observed on WT control plants (FIG. 4B), lines 630A, 630B and 630E transformed with 35S::c630 did not show any symptoms of infection. FIG. 4A shows line 630A which is representative of the other two transformed lines. The photographs were taken at 14 dpi.

Figure 5:

FIG. 5. is a photographic illustration of systemic, non-inoculated leaves of transgenic 35S::c630 *N. tabacum* plants showing partial resistance to PVY at 14 dpi. Seven-week-old *N. tabacum* transgenic 35S::c630 plants were inoculated with PVY$^{NTN}$ as above. Lines C, D, F, G and H showed severe infections symptoms on upper leaves, leading eventually to systemic necrotization and plant death. Only line 630G is shown for the purpose of illustration.

Figure 6B:
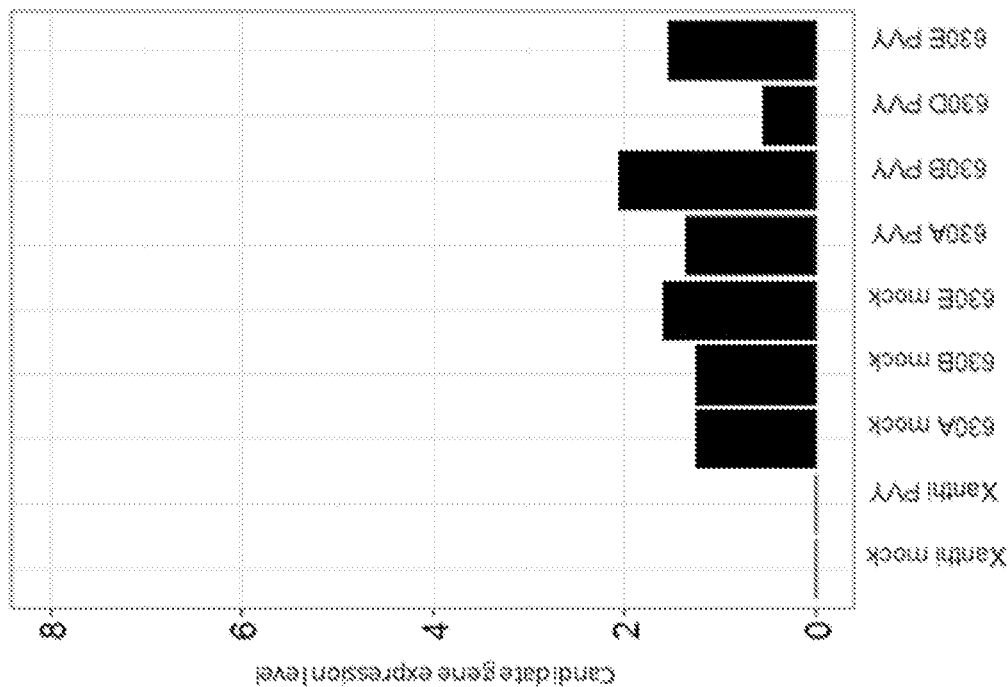
Figure 6A:
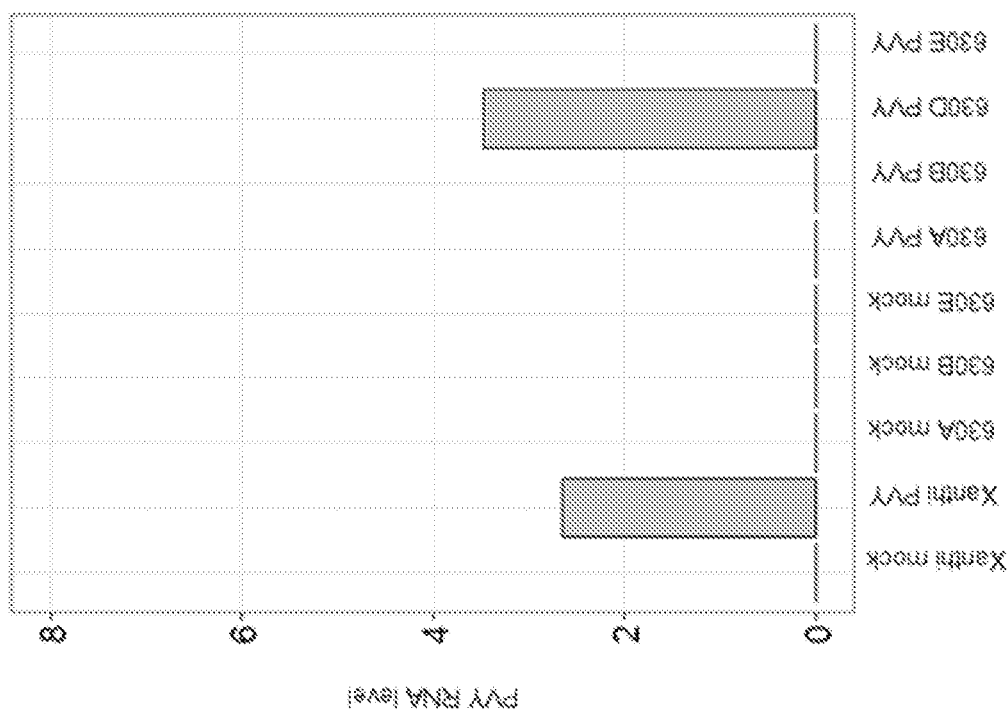
Figure 6D:
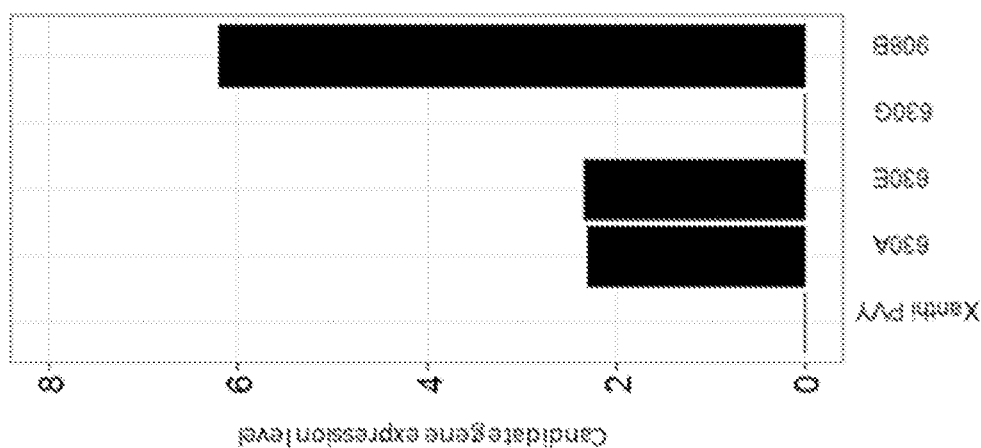
Figure 6C:
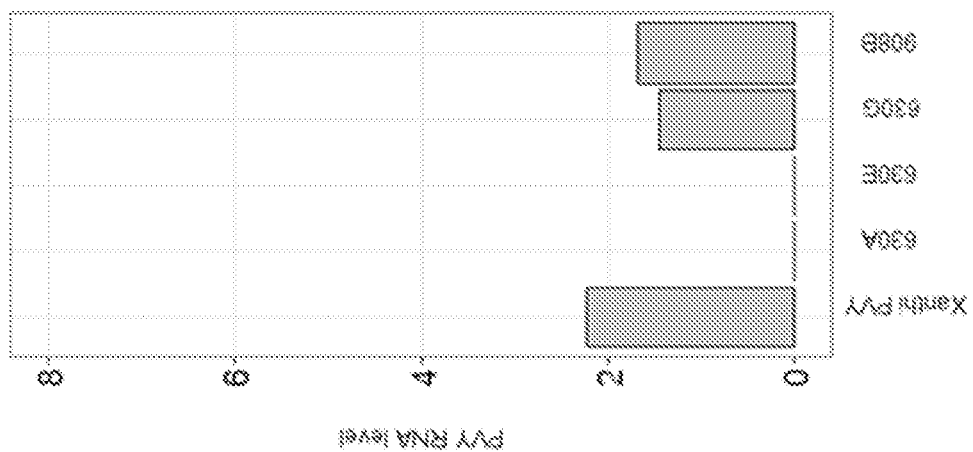

FIGS. 6A-6D is a multi-panel figure that provides graphical illustrations of PVY mRNA levels and the expression levels of candidate gene c630 in stably transformed plants following PVY inoculation. FIGS. 6A and 6C are graphs illustrating levels of PVY mRNA after infection of stable transgenic *N. tabacum* plants transformed with a 35S::c630 construct, and FIGS. 6B and 6D are graphs showing the expression of candidate gene c630 in the same plants. Seven-week-old *N. tabacum* 35S::c630 transgenic and WT control, *N. tabacum* plants were inoculated with PVY$^{NTN}$ as described above or mock treated with inoculation buffer. Seven and 14 days after PVY inoculation, mRNA was isolated from upper, non-inoculated leaves. PVY mRNA levels and the expression of candidate gene c630 were quantified with quantitative RT-PCR. The high expression of the candidate gene c630 (FIG. 6B) correlated with lack of PVY mRNA (FIG. 6A) for lines A, B and E in stable transgenic T0 plants. Resistant lines A and E were again tested in the T1 generation, confirming the results from T0 (FIGS. 6C, 6D). Line 630G (susceptible), for which the expression of c630 was not detected, had PVY mRNA levels similar to control line c908B carrying a non-functional paralog (FIGS. 6C, 6D).

Figure 7A:
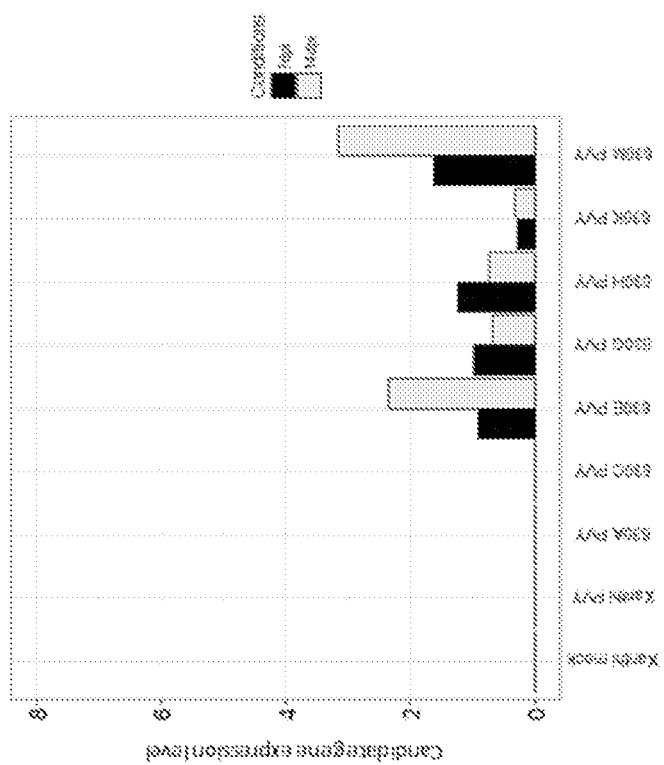
Figure 7B:
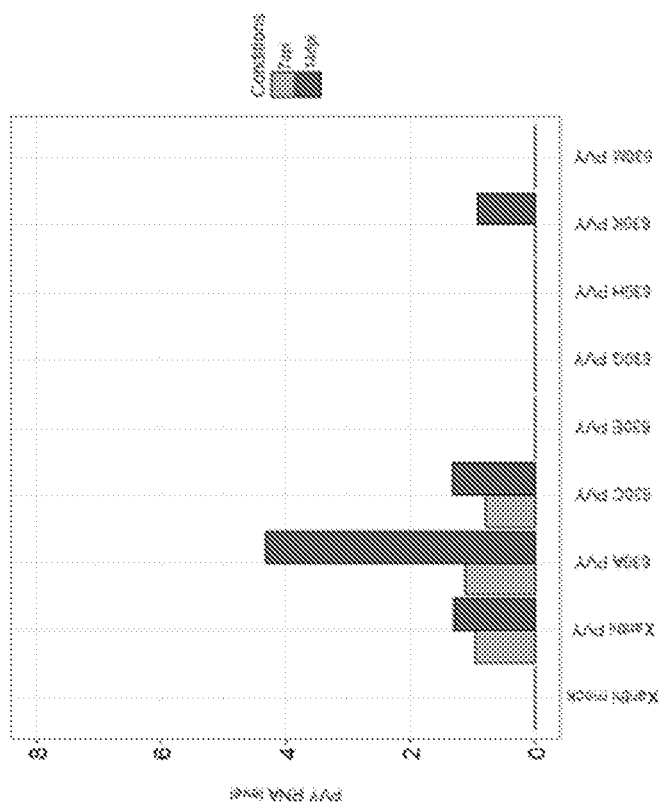

FIGS. 7A-7B is a multi-panel figure that provides graphical illustrations of PVY mRNA levels and the expression levels of candidate gene c630 in stable transgenic *N. tabacum* plants transformed with the c630 gene under the control of its native regulatory elements following PVY inoculation. Seven-week-old *N. tabacum* 35S::c630 transgenic and WT control, *N. tabacum* plants were inoculated with PVY$^{NTN}$ as described above. Seven and 14 days after PVY inoculation, mRNA was isolated from upper, non-inoculated leaves. PVY mRNA levels and the expression of candidate gene c630 were quantified with quantitative RT-PCR. In lines E, G, H and M, high expression of the candidate gene c630 (FIG. 7B) correlated with lack of PVY mRNA (FIG. 7A) in stable transgenic T0 plants.

Figure 8:
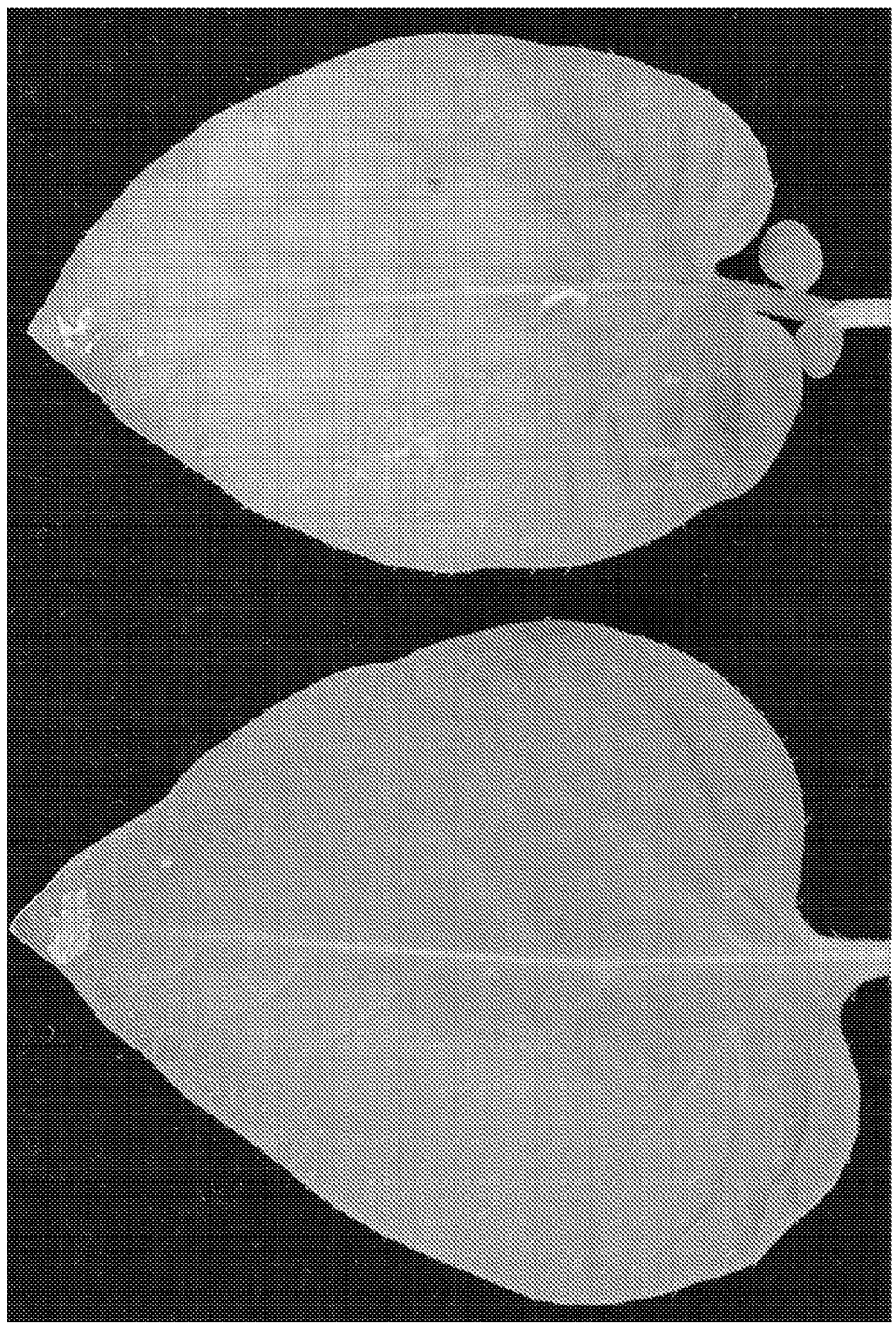

FIG. 8. is a photographic illustration of PVY-inoculated leaves of transgenic 35S::c630 and wild type (WT) *S. tuberosum* cv. Russet Burbank plants showing an ER-type of response. Four-week-old transgenic potato plants cv. Russet Burbank carrying construct 35S::c630, and WT control plants were inoculated with PVY$^{NTN}$ (NIB-NTN). Chlorosis were observed on inoculated leaves of WT plants since 11 dpi (right leaf). Transgenic plants (left leaf) carrying construct 35S::c630 remained symptomless for at least 3 weeks post inoculation (wpi).

Figure 9B:
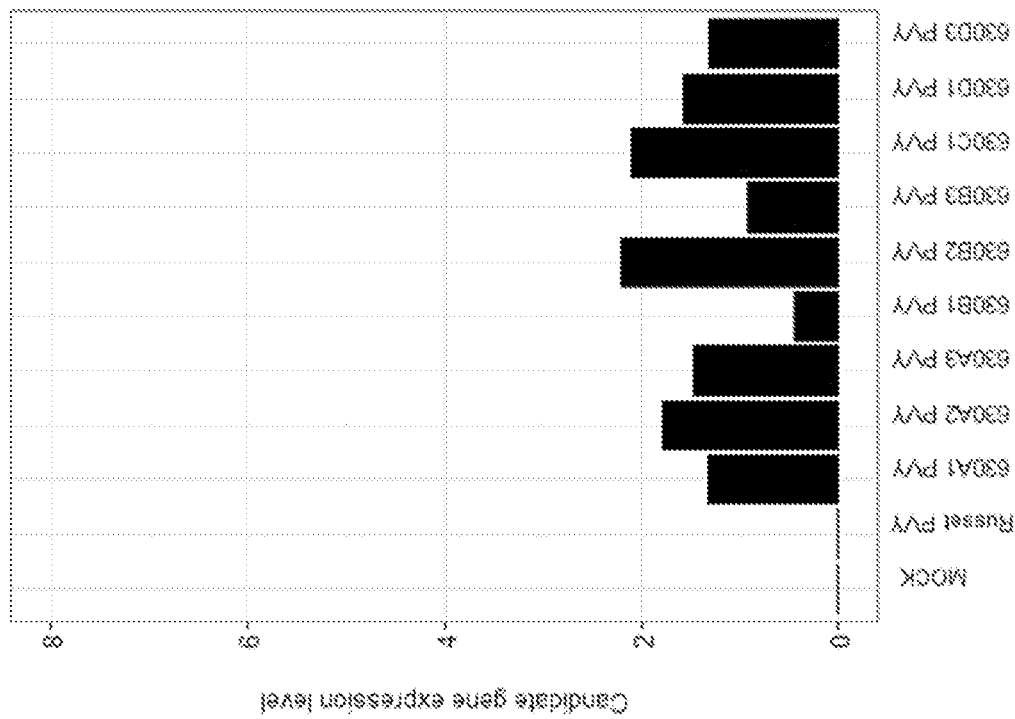
Figure 9A:
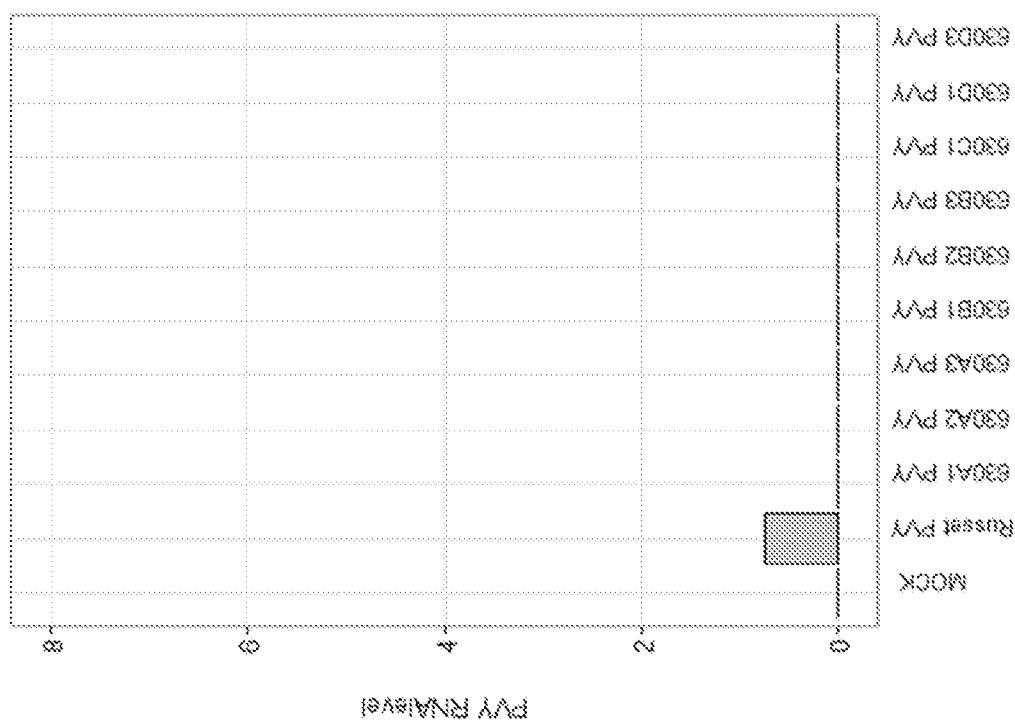

FIGS. 9A-9B. is a multi-panel figure that provides graphical illustrations of PVY mRNA levels and the expression levels of candidate gene c630 in stable, transgenic *S. tuberosum* cv. Russet Burbank plants transformed with the 35S::c630 construct following inoculation with PVY. Seven-week-old potato 35S::c630 transgenic and WT Russet Burbank plants were inoculated with PVY$^{NTN}$ as described above. Three weeks after PVY inoculation, mRNA was isolated from upper, non-inoculated leaves. PVY mRNA levels, and the expression of candidate gene c630 were quantified with quantitative RT-PCR. In all tested lines (A, B, C and D), expression of the candidate gene c630 (FIG. 9B) correlated with lack of PVY mRNA (FIG. 9A) in stable transgenic T0 plants. The presence of PVY mRNA was only detected in WT control plants. The experiment was performed on three plants for line 630A and 630B, on two plants for line 630D, and on one plant for line 630C.

Figure 10B:
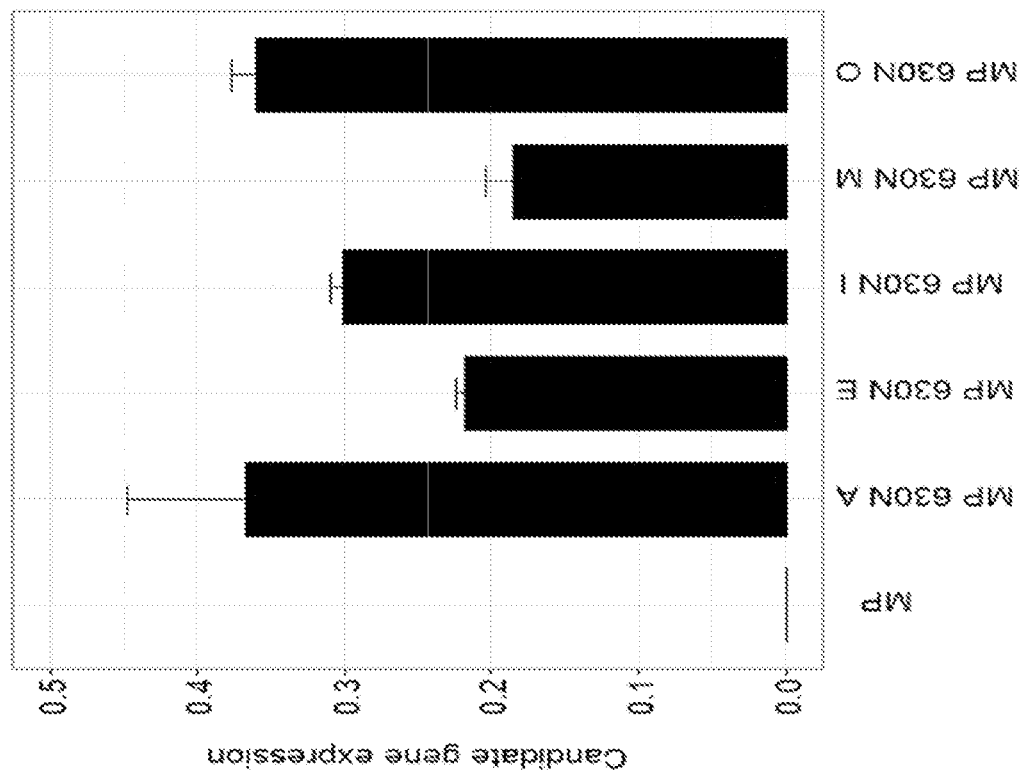
Figure 10A:
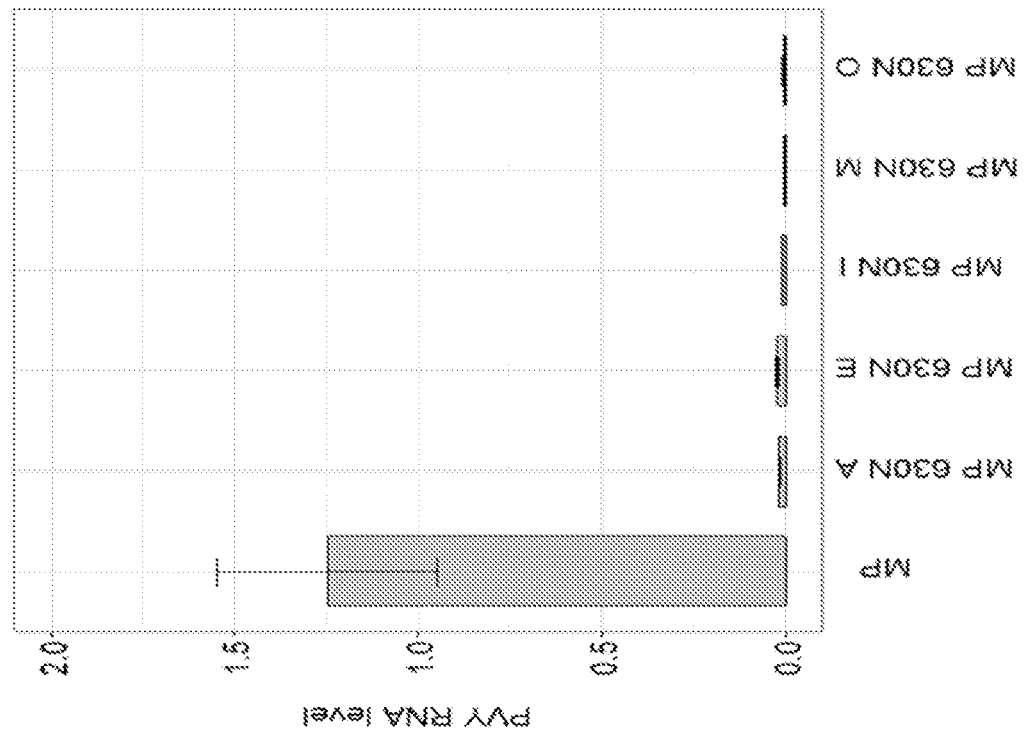

FIGS. 10A-10B is a multi-panel figure that provides graphical illustrations of PVY mRNA levels (FIG. 10A) and the expression levels of the c630 gene (FIG. 10B) in stable, transgenic *S. tuberosum* cv. *Maris* Piper plants transformed with the c630 gene construct comprising the native c630 5'- and 3'-regulatory elements. Four-week-old transgenic potato plants cv. *Maris* Piper carrying the c630 construct were inoculated with PVY$^{NTN}$. Three weeks after PVY inoculation, mRNA was isolated from upper, non-inoculated leaves. In all tested lines (A, E, I, M and O), expression of the candidate gene c630 (FIG. 10B) correlated with lack of PVY mRNA (FIG. 10A) in stable transgenic T0 plants. The presence of PVY mRNA was only detected in WT control plants. The PVY mRNA levels and the expression of Rysto-630 were quantified with qPCR, relative to the expression of the EF1 and Sec3 reference genes and expressed as means±SD calculated from three biological replicates per plant line.

Figure 11:
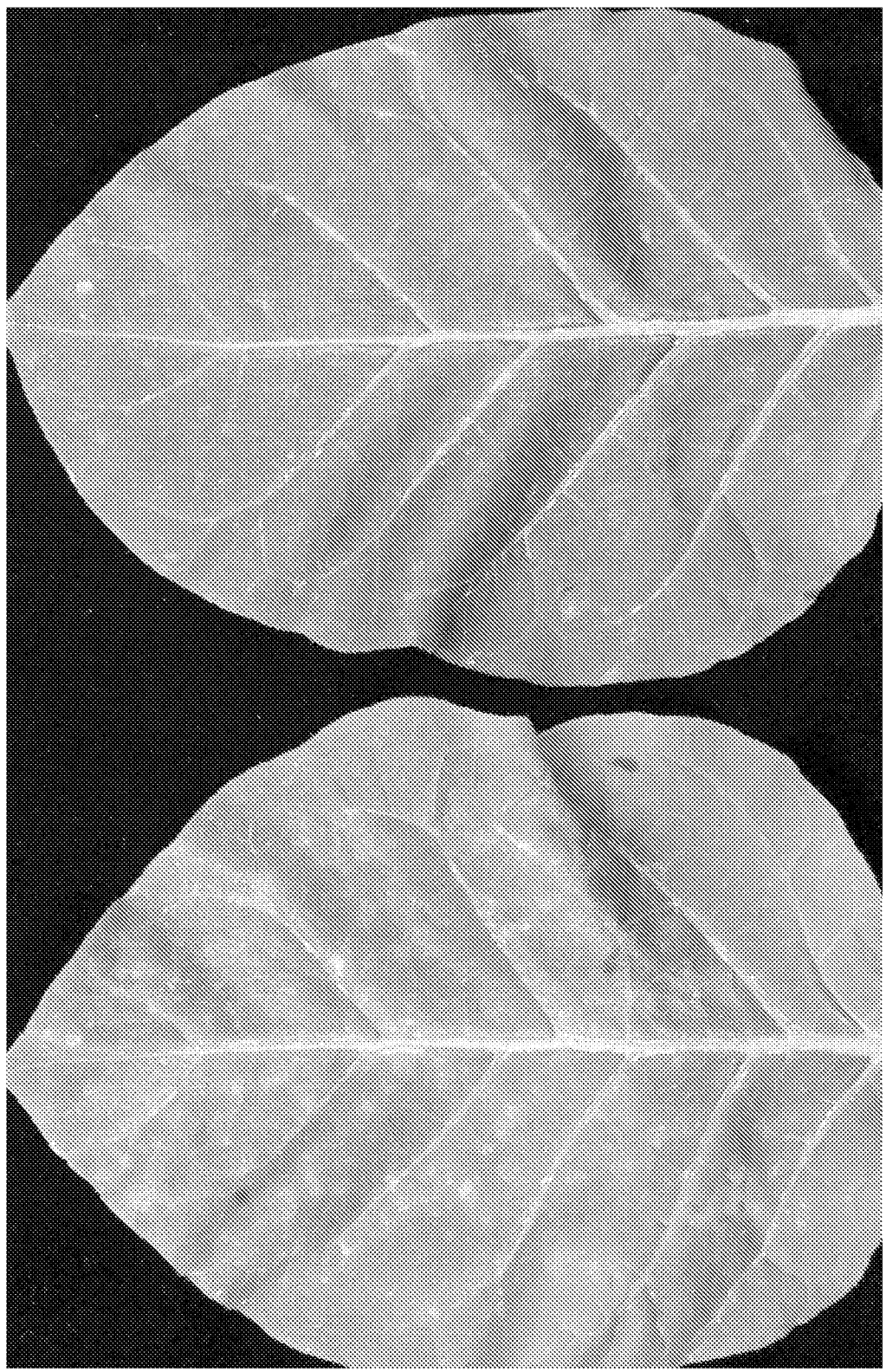

FIG. 11 is a photographic illustration of the HR response after PVA inoculation in stable transgenic N. tabacum plants transformed with 35S::c630. Seven-week-old N. tabacum 35S transgenic and wild-type (WT) control, N. tabacum plants were inoculated with PVA (strain SASA). The HR was observed only on N. tabacum/35S::c630 inoculated leaves (leaf leaf) at 7 dpi. WT control plants remained symptomless (right leaf). The photographs were taken at 10 dpi.

SEQUENCE LISTING

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

SEQ ID NO: 1 sets forth the nucleotide sequence of the R gene, c630.

SEQ ID NO: 2 sets forth the amino acid sequence C630-SV1, the R protein encoded by splice variant 1 of c630.

SEQ ID NO: 3 sets forth the nucleotide sequence of the coding region of the cDNA of splice variant 1 of c630. If desired, a stop codon (e.g. TAA, TAG, TGA) can be operably linked to the 3' end of nucleic acid molecule comprising SEQ ID NO: 3. The native stop codon of this cDNA is TGA.

SEQ ID NO: 4 sets forth the amino acid sequence C630-SV2, the R protein encoded by splice variant 2 of c630.

SEQ ID NO: 5 sets forth the nucleotide sequence of the coding region of the cDNA of splice variant 2 of c630. If desired, a stop codon (e.g. TAA, TAG, TGA) can be operably linked to the 3' end of nucleic acid molecule comprising SEQ ID NO: 5. The native stop codon of this cDNA is TGA.

SEQ ID NO: 6 sets forth the nucleotide sequence of the R gene, c516.

SEQ ID NO: 7 sets forth the amino acid of the R protein encoded by c516

SEQ ID NO: 8 sets forth the nucleotide sequence of the coding region of the cDNA of c516. If desired, a stop codon (e.g. TAA, TAG, TGA) can be operably linked to the 3' end of nucleic acid molecule comprising SEQ ID NO: 8. The native stop codon of this cDNA is TAG.

SEQ ID NO: 9 sets forth the nucleotide sequence of the CaMV 35S promoter::c630 construct that used in to transformed plants as described below in the Examples.

SEQ ID NO: 10 sets forth the nucleotide sequence of the portion of SEQ ID NO: 9 that corresponds to a fragment of c630 (SEQ ID NO: 1) comprising the coding region.

SEQ ID NO: 11 sets forth the nucleotide sequence of the CaMV 35S promoter::c516 construct that used to transform plants as described below in the Examples below.

SEQ ID NO: 12 sets forth the nucleotide sequence of the s portion of SEQ ID NO: 11 that corresponds to a fragment of c516 (SEQ ID NO: 6) comprising the coding region.

SEQ ID NO: 13 sets forth the nucleotide sequence of the c630 native construct (i.e. native regulatory elements) that was used to transform plants as described in the Examples below.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention relates to the isolation of plant resistance (R) genes, particularly R genes that confer upon a solanaceous plant resistance to plant disease(s) caused by one or more strains of the potyviruses, Potato virus Y (PVY) and/or Potato virus A (PVA). As disclosed hereinbelow, an R gene, referred to herein as c630, was isolated from a diploid potato (Solanum tuberosum) mapping population obtained from a cross between PVY-resistant, heterozygous dihaploid clone dH Alicja and susceptible, diploid clone 83-3121 using a method that combined bulked segregant analysis and R gene enrichment and sequencing (RenSeq) to rapidly identify candidate genes encoding nucleotide binding-leucine rich repeat (NLR) proteins.

dH Alicja was selected as the source of PVY resistance because dH Alicja is known to comprise in its genome the resistance gene $Ry_{sto}$ which confers extreme resistance (ER) to multiple strains of PVY. As described in additional detail below, $Ry_{sto}$ was introgressed into the S. tuberosum genome via an interspecific cross with a Solanum stoloniferum plant comprising in its genome $Ry_{sto}$. While it is believed that the results disclosed hereinbelow in the Examples conclusively demonstrate that c630 is $Ry_{sto}$, the present invention does not depend on c630 being $Ry_{sto}$ or $Ry-f_{sto}$, or even on c630 being derived from DNA in the genome of dH Alicja that was introgressed from the genome of S. stoloniferum.

Moreover, it is recognized that there are at least two sources of the Ry resistance trait or gene that is derived from Solanum stoloniferum. One Ry resistance trait is derived from an S. stoloniferum line of Russia origin that is fertile and has the designation $Ry-f_{sto}$ ("f" for fertile). The other Ry resistance trait is derived from an S. stoloniferum line of German origin that is male sterile and has the designation $Ry_{sto}$. It is recognized that dH Alicj a, which is the source of c630 of the present invention, comprises the Ry$_{sto}$ resistance trait that is derived from the male sterile, *S. stoloniferum* line of German origin.

Because the Ry-f$_{sto}$ and Ry$_{sto}$ resistance traits map to the same site on chromosome 12 and potato plants comprising either Ry-f$_{sto}$ or Ry$_{sto}$ have the same PVY resistance phenotype, Ry-f$_{sto}$ and Ry$_{sto}$ may be different alleles of one Ry gene or even the same allele of one Ry gene. Alternatively, Ry-f$_{sto}$ and Ry$_{sto}$ may be separate Ry genes that are tightly linked. Nevertheless, the methods and compositions of the present invention do not depend on whether or not Ry-fito and Ry$_{sto}$ are different alleles of one Ry gene, the same allele of one Ry gene, or are separate Ry genes.

The present invention provides nucleic acid molecules comprising the nucleotide sequences of R genes, particularly the nucleotide sequences of c630 and other naturally occurring (e.g. orthologs and allelic variants) and synthetic or artificial (i.e. non-naturally occurring) variants thereof. As used herein, such nucleic acid molecules are referred to herein as "c630 nucleic acid molecules". Likewise, the nucleotide sequences of c630 and other naturally occurring (e.g. orthologs and allelic variants) and synthetic or artificial (i.e. non-naturally occurring) variants thereof are referred to herein as "c630 nucleotide sequences".

The present invention further provides nucleic acid molecules comprising the nucleotide sequences of R genes, particularly the nucleotide sequences of c516 and other naturally occurring (e.g. orthologs and allelic variants) and synthetic or artificial (i.e. non-naturally occurring) variants thereof. As used herein, such nucleic acid molecules are referred to herein as "c516 nucleic acid molecules". Likewise, the nucleotide sequences of c516 and other naturally occurring (e.g. orthologs and allelic variants) and synthetic or artificial (i.e. non-naturally occurring) variants thereof are referred to herein as "c516 nucleotide sequences". It is recognized that, as used herein, the term "R genes of the present invention" encompasses both the c630 nucleic acid molecules and the c516 nucleic acid molecules described above.

The c630 nucleotide sequences and the c516 nucleotide sequences of the present invention are nucleotide sequences of R genes, which are also referred to herein as R gene nucleotide sequences. Preferably, such nucleotide sequences of R genes encode R proteins. c630 nucleotide sequences and c516 nucleotide sequences of the invention include, but not limited to: the nucleotide sequences of the wild-type or native c630 and c516 genes comprising a native promoter and the native 3' adjacent region comprising the coding region; cDNA sequences; and nucleotide sequences comprising only the coding region. Examples of such c630 nucleotide sequences include the nucleotide sequences set forth in SEQ ID NOS: 1, 3, 5, 9, 10, and 13, and variants thereof. Examples of such c516 nucleotide sequences include the nucleotide sequences set forth in SEQ ID NOS: 6, 8, 11, and 12, and variants thereof. In embodiments in which the native c630 or c516 gene promoter is not used to drive the expression of the nucleotide sequence encoding the R protein, a heterologous promoter can be operably linked a nucleotide sequence encoding an R protein of the invention to drive the expression of nucleotide sequence encoding an R protein in a plant.

Preferably, the R proteins encoded by the c630 nucleotide sequences and the c516 nucleotide sequences of the invention are functional R proteins, or part(s), or domain(s) thereof, which are capable of conferring on a plant, particularly a solanaceous plant, comprising the R protein, enhanced resistance to a plant disease caused by at least one strain of PVY and/or PVA. PVY strains include, but are not limited to, PVY$^O$, PVY$^C$, PVY$^Z$, PVY$^N$, PVY$^{NTN}$, PVY$^{N\text{-}Wilga}$, and PVY$^E$. PVA strains include, but are not limited to, PVA-1, PVA-2, PVA-3 which correspond to isolates PVA-U, PVA-M, and PVA-B11, respectively (Valkonen et al. (1995) Plant Dis. 79:748-753.) Other PVA strains include, for example, PVA-SASA and PVA-X Bonin.

In certain preferred embodiments, the R proteins of the present invention comprise broad-spectrum resistance to multiple strains of PVY and/or PVA and include, for example, C630-SV1 (SEQ ID NO: 2) and C630-SV2 (SEQ ID NO: 4), the two R proteins encoded by c630 (SEQ ID NO: 1). Such R proteins are encoded by the c630 nucleotide sequences set forth in SEQ ID NOS: 1, 3, and 5 and variants thereof. In certain other preferred embodiments, the R proteins of the present invention comprise broad-spectrum resistance to multiple strains of PVY and include, for example, C516 (SEQ ID NO: 7), the R protein encoded by c516 (SEQ ID NO: 6). Such R proteins are encoded by the c516 nucleotide sequences set forth in SEQ ID NOS: 6, 8, 11, and 12, and variants thereof.

The present invention further provides plants comprising a heterologous polynucleotide which comprises an R gene nucleotide sequence of the present invention. Preferably, such an R gene nucleotide sequence encodes a full-length R protein of the present invention, or at least a functional part(s) or domain(s) thereof. In some embodiments, such a heterologous polynucleotide of the present invention is stably incorporated into the genome of the plant, and in other embodiments, the plant is transformed by a transient transformation method and the heterologous polynucleotide is not stably incorporated into the genome of the plant.

In other embodiments, a plant comprising a heterologous polynucleotide which comprises an R gene nucleotide sequence of the present invention is produced using a method of the present invention that involves genome editing to modify the nucleotide sequence of a native or non-native gene in the genome of the plant. The native or non-native gene comprises a nucleotide sequence that is different from (i.e. not identical to) an R gene nucleotide sequence of the present invention, and after modification by methods disclosed in further detail hereinbelow, the modified native or non-native gene comprises an R gene nucleotide sequence of the present invention. Generally, such methods comprise the use of a plant comprising in its genome a native or non-native gene wherein the native or non-native gene comprises a nucleotide sequence that is homologous to an R gene nucleotide sequence of the present invention and further comprises introducing into the plant a nucleic acid molecule comprising at least part of an R gene nucleotide sequence of the present invention. Preferably, a nucleotide sequence of native or non-native gene comprises about 70%, 75% 80%, 85%, 90%, 95%, 96%, 97%, 98%, 99% or greater nucleotide sequence identity to at least one R gene nucleotide sequence of the present invention. Such a native or non-native gene can be, for example an R gene, or a non-functional homolog of such an R gene that is not, or is not known to be, capable of conferring to a plant, resistance to a plant disease. It is recognized that a plant produced by genome engineering as disclosed herein is a stably transformed plant when the native or non-native gene that is modified is stably incorporated in the genome of the plant.

Methods for both the stable and transient transformation of plants and genome editing are disclosed elsewhere herein or otherwise known in the art. In one embodiment of the invention, the plants are stably transformed potato or tomato plants comprising a heterologous polynucleotide of the present invention stably incorporated into their respective genomes and further comprising enhanced resistance to plant disease caused by at least one strain of PVY, enhanced resistance to plant disease caused by at least one strain of PVA, and/or enhanced resistance to plant disease caused by at least other potyvirus (i.e. a potyvirus other than PVY or PVA). In another embodiment of the invention, the plants are stably transformed potato or tomato plants comprising a heterologous polynucleotide of the present invention stably incorporated into their respective genomes and further comprising enhanced resistance to plant disease caused by at least two, three, four, five, six or more strains of PVY and/or PVA, and optionally comprise enhanced resistance to at least one other potyvirus.

In certain embodiments, a plant of the invention comprises a heterologous polynucleotide which comprises a nucleotide sequence encoding an R protein of the present invention and a heterologous promoter that is operably linked for expression of the nucleotide sequence encoding an R protein. The choice of heterologous promoter can depend on a number of factors such as, for example, the desired timing, localization, and pattern of expression as well as responsiveness to particular biotic or abiotic stimulus. Promoters of interest include, but are not limited to, pathogen-inducible, constitutive, tissue-preferred, wound-inducible, and chemical-regulated promoters.

In certain embodiments of the invention, the plant of the invention, particularly a solanaceous plant, can comprise one, two, three, four, five, six, or more nucleotide sequences encoding an R protein. Typically, but not necessarily, the two or more R proteins will be different from each other. For the present invention, an R protein is different from another R protein when the two R proteins have non-identical amino acid sequences. In some embodiments of the invention, a solanaceous plant can comprise a nucleotide sequence encoding both C630-SV1 and C630-SV2. In other embodiments, a solanaceous plant can comprise a first nucleotide sequence encoding C630-SV1 and a second nucleotide sequence encoding C630-SV2. In yet other embodiments, a solanaceous plant can comprise a first nucleotide sequence encoding both C630-SV1 and C630-SV2 and a second nucleotide sequence encoding C516. In still yet other embodiments, a solanaceous plant can comprise a first nucleotide sequence encoding C630-SV1, a second nucleotide sequence encoding C630-SV2, and a third nucleotide sequence encoding C516.

One or more nucleic acid molecules comprising an R genes nucleotide sequences of the present invention can be combined in a single plant, particularly solanaceous plant, with any one or more other R genes for plant disease caused by PVY and/or PVA, or for any other plant disease caused by a plant pathogen such as, for example, late blight caused by *Phytophthora infestans*. Other R genes for plant disease caused by PVY include, but are not limited to, Ncspl, Nytbr, $Ry_{chc}$, Ny-1, Ny-Smira, $Ry_{adg}$, and Ny-2 (see Table 1 above). Late blight R genes, which are also referred to as Rpi (i.e. Resistance to *Phytophthora infestans*) genes, can be combined in single solanaceous plant (e.g. a potato plant) comprising at least one R gene nucleotide sequence of the present invention include, but are not limited to, the following cloned Rpi genes: Rpi-amr1e and the Rpi-amr1e orthologs (U.S. Provisional Pat. App. No. 62/435,451; filed Dec. 16, 2016), Rpi-amr3i (Accession No. KT373889; SEQ ID NO: 1 of WO 2016/182881) Rpi-blb1 (also known as "RB"; Accession Nos. FB764493.1 and AY336128.1), Rpi-sto1 (Accession No. EU884421), Rpi-pta1 (Accession No. EU884422), Rpi-b1b2 (Accession No. DQ122125), Rpi-b1b3 (Accession No. FJ536326), Rpi-abpt (Accession No. FJ536324), R2-like (Accession No. FJ536323), R2 (Accession No. FJ536325), Rpi-edn1.1 (Accession No. GU563963), Rpi-edn1.2, Rpi-snk1.1, Rpi-snk1.2, Rpi-hjt1.1-Rpi-hjt1.3 (Accession No. GU563971-3), Rpi-bt1 (Accession No. FJ188415), R1 (Accession No. AF447489), R3a (Accession No. AY849382), R3b (Accession No. JF900492), Rpi-vnt1.1 (Accession No. FJ423044), Rpi-vnt1.2 (Accession No. FJ423045), Rpi-vnt1.3 (Accession No. FJ423046), Rpi-mcql (Accession No. GN043561), Rpi-chc, Ph-3 (Accession No. KJ563933), and R8 (Accession No. KU530153). The nucleotide sequences corresponding to the accession numbers of either the genes listed above or any genes or proteins disclosed elsewhere herein can be obtained from publicly accessible, online nucleotide and amino acid sequence databases such as, for example, the GenBank and EMBL databases (available on the World Wide Web at ncbi.nlm.nih.gov/genbank and ebi.ac.uk, respectively).

A plant of the invention comprising multiple R genes can be produced, for example, by transforming a plant that already comprises one or more other R gene nucleotide sequences with a heterologous polynucleotide comprising an R gene nucleotide sequence of the present invention including, for example, an c630 or c516 nucleotide sequence. Such a plant that already comprises one or more other R gene nucleotide sequences can comprise R genes that are native to the genome or the plant, that were introduced into the plant via sexual reproduction, or that were introduced by transforming the plant or a progenitor thereof with an R gene nucleotide sequence. Alternatively, the one or more other R gene nucleotide sequences can be introduced into a plant of the invention, which already comprises a heterologous polynucleotide of the invention, by, for example, transformation or sexual reproduction.

In other embodiments, two or more different R gene sequences can be introduced into a plant by stably transforming the plant with a heterologous polynucleotide or vector comprising two or more R gene nucleotide sequences. It is recognized that such an approach can be preferred for plant breeding as it is expected that the two or more R gene nucleotide sequences will be tightly linked and thus, segregate a single locus. Alternatively, a heterologous polynucleotide of the present invention can be incorporated into the genome of a plant in the immediate vicinity of another R gene nucleotide sequence using homologous recombination-based genome modification methods that are described elsewhere herein or otherwise known in the art.

The present invention further provides methods for enhancing the resistance of a plant to a plant disease caused by at least one potyvirus, particularly at least one strain of PVY and/or at least one strain of PVA. The methods comprise modifying at least one plant cell to comprise a heterologous polynucleotide, and optionally regenerating a plant from the modified plant comprising the heterologous polynucleotide. In a first aspect, the methods for enhancing the resistance of a plant to a plant disease caused by at least one potyvirus comprise introducing a heterologous polynucleotide of the invention into at least one plant cell, particularly a plant cell from a solanaceous plant. In certain embodiments, the heterologous polynucleotide is stably incorporated into the genome of the plant cell.

In a second aspect, the methods for enhancing the resistance of a plant to a plant disease caused by at least one potyvirus, particularly at least one strain of PVY and/or at least one strain of PVA, involve the use of a genome-editing method to modify the nucleotide sequences of a native or non-native gene in the genome of the plant cell to comprise a heterologous polynucleotide of the present invention. The methods comprise introducing a nucleic acid molecule into the plant cell, wherein the nucleic acid molecule comprises a nucleotide sequence comprising at least a part of the R gene nucleotide sequence of the present invention and wherein at least a part of the nucleotide sequence of the native or non-native gene is replaced with at least a part of the nucleotide sequence of the nucleic acid molecule. Thus, the methods of the invention involve gene replacement to produce a heterologous polynucleotide of the present invention in the genome of a plant cell.

If desired, the methods of the first and/or second aspect(s) can further comprise regenerating the plant cell into a plant comprising in its genome the heterologous polynucleotide. Preferably, such a regenerated plant comprises enhanced resistance to a plant disease caused by at least one potyvirus, at least one strain of PVY, and/or at least one strain of PVA, relative to the resistance of a control plant to the plant disease or diseases caused by the same potyvirus(es), strain(s) of PVY and/or strain(s) of PVA.

The methods of the present invention for enhancing the resistance of a plant to a plant disease caused by at least one potyvirus, at least one strain of PVY, and/or at least one strain of PVA can further comprise producing a plant comprising two, three, or more nucleotide sequences encoding an R protein, preferably each nucleotide sequence encoding a different R protein. Such a plant comprising multiple R gene nucleotide sequences comprises one or more additional R gene nucleotide sequences of the present invention and/or any other nucleotide sequence encoding an R protein known in the art. It is recognized that the methods of the first and/or second aspect can be used to produce such a plant comprising multiple nucleotide sequences encoding an R protein. Moreover, it is recognized that a heterologous polynucleotide of the present invention can comprise, for example, one or more R gene nucleotide sequences of the present invention or at least one R gene nucleotide sequences of the present invention and one or more nucleotide sequences encoding an R protein that is known in the art.

The plants disclosed herein find use in methods for limiting plant disease caused by at least one potyvirus, at least one strain of PVY, and/or at least one strain of PVA in agricultural crop production, particularly in regions where such a plant disease is prevalent and is known to negatively impact, or at least has the potential to negatively impact, agricultural yield. The methods of the invention comprise planting a plant (e.g. a seedling), tuber, or seed of the present invention, wherein the plant, tuber, or seed comprises at least one R gene nucleotide sequence of the present invention. The methods further comprise growing the plant that is derived from the seedling, tuber, or seed under conditions favorable for the growth and development of the plant, and optionally harvesting at least one fruit, tuber, leaf, or seed from the plant.

The present invention additionally provides methods for identifying a solanaceous plant that comprises an R gene for a plant disease caused by at least one potyvirus, at least one strain of PVY, and/or at least one strain of PVA. The methods find use in breeding solanaceous plants for resistance to plant diseases caused PVY, PVA, and/or other potyviruses. Such resistant plants find use in the agricultural production of fruits, tubers, leaves, and/or seeds for human or livestock consumption or other use. The methods comprise detecting in a solanaceous plant, or in at least one part or cell thereof, the presence of: a c630 nucleotide sequence of the present invention, a c516 nucleotide sequence of the present invention, or both a c630 nucleotide sequence and a c516 nucleotide sequence. In some embodiments of the invention, detecting the presence of the c630 or c516 nucleotide sequence comprises detecting the entire c630 or c516 nucleotide sequence in genomic DNA isolated from a solanaceous plant. In preferred embodiments, however, detecting the presence of a c630 or c516 nucleotide sequence comprises detecting the presence of at least one marker within the c630 or c516 nucleotide sequence, respectively. In other embodiments of the invention, detecting the presence of a c630 nucleotide sequence comprises detecting the presence of either one, or both, of the R proteins encoded by the c630 nucleotide sequence using, for example, immunological detection methods involving an antibody preparation specific to C630-SV1 and/or an antibody preparation specific to C630-SV2. Alternatively, an antibody preparation (e.g. polyclonal antibody) that is capable of binding to both C630-SV1 and C630-SV2 can be used if the separate detection of the variant C630 proteins is not desired. In yet embodiments of the invention, detecting the presence of a nucleotide sequence comprises detecting the presence of the R protein encoded by the c516 nucleotide sequence using, for example, immunological detection methods involving antibodies specific to C516.

In the methods for identifying a solanaceous plant that comprises an R gene for a plant disease caused by at least one potyvirus, at least one strain of PVY, and/or at least one strain of PVA, detecting the presence of the c630 nucleotide sequence and/or the c516 nucleotide sequence in the solanaceous plant can involve one or more of the following molecular biology techniques that are disclosed elsewhere herein or otherwise known in the art including, but not limited to, isolating genomic DNA and/or RNA from the plant, amplifying nucleic acid molecules comprising the c630 nucleotide sequence and/or the c516 nucleotide sequence and/or marker(s) therein by PCR amplification, sequencing nucleic acid molecules comprising the c630 nucleotide sequence and/or the c516 nucleotide sequence and/or marker(s), identifying the c630 nucleotide sequence and/or the c516 nucleotide sequence, the marker(s), or a transcript or transcripts of the c630 nucleotide sequence and/or a transcript the c516 nucleotide sequence by nucleic acid hybridization, and conducting an immunological assay for the detection of the R protein(s) encoded by the c630 nucleotide sequence and/or the c516 nucleotide sequence. It is recognized that oligonucleotide probes and PCR primers can be designed to identity the c630 nucleotide sequence and/or the c516 nucleotide sequence of the present invention and that such probes and PCR primers can be utilized in methods disclosed elsewhere herein or otherwise known in the art to rapidly identify in a population of plants one or more plants comprising the presence of an c630 nucleotide sequence and/or an c516 nucleotide sequence of the present invention.

Depending on the desired outcome, the heterologous polynucleotides of the invention can be stably incorporated into the genome of the plant cell or not stably incorporated into genome of the plant cell. If, for example, the desired outcome is to produce a stably transformed plant with enhanced resistance to a plant disease caused by at least one potyvirus, at least one strain of PVY, and/or at least one strain of PVA, then the heterologous polynucleotide can be, for example, fused into a plant transformation vector suitable for the stable incorporation of the heterologous polynucleotide into the genome of the plant cell. Typically, the stably transformed plant cell will be regenerated into a transformed plant that comprises in its genome the heterologous polynucleotide. Such a stably transformed plant is capable of transmitting the heterologous polynucleotide to progeny plants in subsequent generations via sexual and/or asexual reproduction. Plant transformation vectors, methods for stably transforming plants with an introduced heterologous polynucleotide and methods for plant regeneration from transformed plant cells and tissues are generally known in the art for both monocotyledonous and dicotyledonous plants or described elsewhere herein.

In other embodiments of the invention in which it is not desired to stably incorporate the heterologous polynucleotide in the genome of the plant, transient transformation methods can be utilized to introduce the heterologous polynucleotide into one or more plant cells of a plant. Such transient transformation methods include, for example, viral-based methods which involve the use of viral particles or at least viral nucleic acids. Generally, such viral-based methods involve constructing a modified viral nucleic acid comprising a heterologous polynucleotide of the invention operably linked to the viral nucleic acid and then contacting the plant either with a modified virus comprising the modified viral nucleic acid or with the viral nucleic acid or with the modified viral nucleic acid itself. The modified virus and/or modified viral nucleic acid can be applied to the plant or part thereof, for example, in accordance with conventional methods used in agriculture, for example, by spraying, irrigation, dusting, or the like. The modified virus and/or modified viral nucleic acids can be applied in the form of directly sprayable solutions, powders, suspensions or dispersions, emulsions, oil dispersions, pastes, dustable products, materials for spreading, or granules, by means of spraying, atomizing, dusting, spreading or pouring. It is recognized that it may be desirable to prepare formulations comprising the modified virus and/or modified viral nucleic acids before applying to the plant or part or parts thereof. Methods for making pesticidal formulations are generally known in the art or described elsewhere herein.

The present invention provides nucleic acid molecules comprising c630 nucleotide sequences and nucleic acid molecules comprising c516 nucleotide sequences. Preferably, such nucleic acid molecules are capable of conferring upon a host plant, particularly a solanaceous host plant, enhanced resistance to a plant disease caused by at least one potyvirus, at least one strain of PVY, and/or at least one strain of PVA. Thus, such nucleic acid molecules find use in limiting a plant disease caused by PVY, PVA, and/or other potyviruses in agricultural production. The nucleic acid molecules of the present invention include, but are not limited to, nucleic acid molecules comprising at least one of the c630 and c516 nucleotide sequence disclosed herein but also additional orthologs and other variants of the c630 and c516 nucleotide sequences that are capable of conferring to a plant resistance to a plant disease caused by at least one potyvirus, at least one strain of PVY, and/or at least one strain of PVA. Methods are known in the art or otherwise disclosed herein for determining resistance of a plant a plant disease caused by at least one potyvirus, at least one strain of PVY, and/or at least one strain of PVA, including, for example, the assays described hereinbelow.

Additionally provided are methods for introducing c630 and/or c516 into a solanaceous plant lacking in its genome c630 (SEQ ID NO: 1, 10, or 13) and/or c516 (SEQ ID NO: 6 or 12). The methods comprise crossing (i.e. cross-pollinating) a first solanaceous plant comprising in its genome at least one copy of c630 and/or c516 with a second solanaceous plant lacking in its genome c630 and/or c516. The first and second solanaceous plants can be the same solanaceous species or can be different solanaceous species. For example, the first solanaceous plant can be a *S. stoloniferum* plant or *S. tuberosum* plant and the second solanaceous plant can be *S. tuberosum* lacking c630 and/or c516. Such a crossing of a first species of a plant to a second species of a plant is known as an interspecific hybridization and can be used to introgress a gene or genes of interest (e.g. c630) from one species into a related species lacking the gene or genes of interest and typically involves multiple generations of backcrossing of the progeny with the related species and selection at each generation of progeny comprising the gene or genes of interest. Such interspecific hybridization, introgression, and backcrossing methods are well known in the art and can be used in the methods of the present invention. See "Principals of Cultivar Development," Fehr, 1993, Macmillan Publishing Company, New York; and "Fundamentals of Plant Genetics and Breeding," Welsh, 1981, John Wiley & Sons, Inc., New York.

In methods of the present invention for introducing c630 and/or c516 into a solanaceous plant lacking in its genome c630 and/or c516, either the first solanaceous plant or the second solanaceous plant can be the pollen donor plant. For example, if the first solanaceous plant is the pollen donor plant, then the second solanaceous plant is the pollen-recipient plant. Likewise, if the second solanaceous plant is the pollen donor plant, then the first solanaceous plant is the pollen-recipient plant. Following the crossing, the pollen-recipient plant is grown under conditions favorable for the growth and development of the plant and for a sufficient period of time for seed to mature or to achieve an otherwise desirable growth stage for use in a subsequent in vitro germination procedure such as, for example, embryo rescue that is described below. The seed can then be harvested and those seed comprising c630 and/or c516 identified by any method known in the art including, for example, the methods for identifying a solanaceous plant that comprises an R gene for a plant disease caused by at least one strain of PVY and at least one strain of PVA that are described elsewhere herein. In certain embodiments, the first solanaceous plant is a *S. stoloniferum* or a *S. tuberosum* plant comprising c630 and/or c516 and the second plant is *S. tuberosum* plant lacking c630 and/or c516.

It is recognized, however, that in certain embodiments of the invention involving interspecific hybridizations, it may be advantageous to harvest the seed resulting from such interspecific hybridizations at an immature growth stage and then to germinate the immature seeds in culture (i.e. in vitro), whereby the seeds are allowed germinate in culture using methods known in art as "embryo rescue" methods. See Reed (2005) "Embryo Rescue," in *Plant Development and Biotechnology*, Trigiano and Gray, eds. CRC Press, Boca Raton, pp. 235-239; and Sharma et al. (1996) *Euphytica* 89: 325-337. It is further recognized that "embryo rescue methods are typically used when mature seeds produced by an interspecific cross display little or no germination, whereby few or no interspecific hybrid plants are produced.

The methods of the present invention find use in producing plants with enhanced resistance to a plant disease caused by at least one potyvirus, at least one strain of PVY, and/or at least one strain of PVA. Typically, the methods of the present invention will enhance or increase the resistance of the subject plant to the plant disease by at least 25%, 50%, 75%, 100%, 150%, 200%, 250%, 500% or more when compared to the resistance of a control plant to the same potyvirus(es), strain(s) of PVY and/or strain(s) of PVA. Unless stated otherwise or apparent from the context of a use, a control plant for the present invention is a plant that does not comprise the heterologous polynucleotide, the c630 nucleotide sequence and/or the c516 nucleotide sequence of the present invention. Preferably, the control plant is essentially identical (e.g. same species, subspecies, and variety) to the plant comprising the heterologous polynucleotide of the present invention except the control does not comprise the heterologous polynucleotide, the c630 nucleotide sequence and/or the c516 nucleotide sequence. In some embodiments, the control will comprise a heterologous, control polynucleotide (e.g. vector control) that does comprise the one or more c630 and/or c516 nucleotide sequences that are in a heterologous polynucleotide of the present invention.

Additionally, the present invention provides transformed plants, seeds, and plant cells produced by the methods of present invention and/or comprising a heterologous polynucleotide of the present invention. Also provided are progeny plants and seeds thereof comprising a heterologous polynucleotide of the present invention. The present invention also provides fruits, seeds, tubers, leaves, stems, roots, and other plant parts produced by the transformed plants and/or progeny plants of the invention as well as food products and other agricultural products comprising, or produced or derived from, the plants or any part or parts thereof including, but not limited to, fruits, tubers, leaves, stems, roots, and seed. Other agricultural products include, for example, smoking products produced from tobacco leaves (e.g., cigarettes, cigars, and pipe and chewing tobacco) and food and industrial starch products produced from potato tubers. It is recognized that such food products can be consumed or used by humans and other animals including, but not limited to, pets (e.g., dogs and cats), livestock (e.g., pigs, cows, chickens, turkeys, and ducks), and animals produced in freshwater and marine aquaculture systems (e.g. fish, shrimp, prawns, crayfish, and lobsters).

Non-limiting examples of the compositions and methods of the present invention are as follows:

1. A nucleic acid molecule comprising a nucleotide sequence selected from the group consisting of:
   (a) the nucleotide sequence set forth in SEQ ID NO: 1, 6, 10, 12, or 13;
   (b) a nucleotide sequence encoding the amino acid sequence set forth in SEQ ID NO: 2, 4, or 7, and optionally, wherein the nucleotide sequence is not naturally occurring;
   (c) the nucleotide sequence set forth in SEQ ID NO: 3, 5, 8, 9, or 11;
   (d) a nucleotide sequence having at least 90% sequence identity to at least one of the nucleotide sequences set forth in SEQ ID NOS: 1, 3, 5, 6, 8, 10, 12, and 13, wherein the nucleic acid molecule is capable of conferring resistance to a plant disease caused by at least one strain of Potato virus Y (PVY), at least one strain of Potato virus A (PVA), and/or at least one potyvirus, relative to a control plant not comprising the nucleic acid molecule and optionally, wherein the nucleotide sequence is not naturally occurring; and
   (e) a nucleic acid molecule comprising a nucleotide sequence encoding an amino acid sequence having at least 90% sequence identity to at least one of the amino acid sequences set forth in SEQ ID NO: 2, 4 and 7, wherein the nucleic acid molecule is capable of conferring resistance to a plant disease caused by at least one strain of PVY, at least one strain of PVA, and/or at least one potyvirus, relative to a control plant not comprising the nucleic acid molecule and optionally, wherein the nucleotide sequence is not naturally occurring.

2. The nucleic acid molecule of embodiment 1, wherein the nucleic acid molecule is an isolated nucleic acid molecule.
3. An expression cassette comprising the nucleic acid molecule of embodiment 1 or 2 and an operably linked heterologous promoter.
4. A vector comprising the nucleic acid molecule of embodiment 1 or 2 or the expression cassette of embodiment 3.
5. A vector of embodiment 4, further comprising an additional R gene.
6. A host cell transformed with the nucleic acid molecule of embodiment 1 or 2, the expression cassette of embodiment 3, or the vector of embodiment 4 or 5.
7. The host cell of embodiment 6, wherein the host cell is a plant cell, a bacterium, a fungal cell, or an animal cell.
8. The host cell of embodiment 6 or 7, wherein the host cell is a solanaceous plant cell.
9. A plant or plant cell comprising the nucleic acid molecule of embodiment 1 or 2, the expression cassette of embodiment 3, or the vector of embodiment 4 or 5.
10. The plant or plant cell of embodiment 9, wherein the plant is a solanaceous plant and the plant cell is a solanaceous plant cell.
11. The plant of embodiment 10, wherein the solanaceous plant is the solanaceous plant is selected from the group consisting of potato, tomato, eggplant, pepper, tomatillo, tobacco, and petunia.
12. A plant or plant cell comprising stably incorporated in its genome a heterologous polynucleotide comprising a nucleotide sequence selected from the group consisting of:
   (a) the nucleotide sequence set forth in SEQ ID NO: 1, 6, 10, 12, or 13;
   (b) a nucleotide sequence encoding the amino acid sequence set forth in SEQ ID NO: 2, 4, or 7;
   (c) the nucleotide sequence set forth in SEQ ID NO: 3, 5, 8, 9, or 11;
   (d) a nucleotide sequence having at least 90% sequence identity to at least one of the nucleotide sequences set forth in SEQ ID NOS: 1, 3, 5, 6, 8, 10, 12, and 13, wherein the nucleic acid molecule is capable of conferring resistance to a plant disease caused by at least one strain of PVY, at least one strain of PVA, and/or at least one potyvirus, relative to a control plant not comprising the nucleic acid molecule; and
   (e) a nucleic acid molecule comprising a nucleotide sequence encoding an amino acid sequence having at least 90% sequence identity to at least one of the amino acid sequences set forth in SEQ ID NO: 2, 4 and 7, wherein the nucleic acid molecule is capable of conferring resistance to a plant disease caused by at least one strain of PVY, at least one strain of PVA, and/or at least one potyvirus, relative to a control plant not comprising the nucleic acid molecule.
13. The plant or plant cell of embodiment 12, wherein the heterologous polynucleotide comprises the nucleotide sequence of any one of (b)-(e) and further comprises a promoter operably linked for the expression of the nucleotide sequence in a plant.
14. The plant or plant cell of embodiment 13, wherein the promoter is selected from the group consisting of pathogen-inducible, constitutive, tissue-preferred, wound-inducible, and chemical-regulated promoters.
15. The plant or plant cell of any one of embodiments 12-14, wherein the plant or plant cells is a solanaceous plant or plant cell.
16. The plant or plant cell of any one of embodiments 12-15, wherein the solanaceous plant or plant cell is selected from the group consisting of potato, tomato, eggplant, pepper, tomatillo, tobacco, and petunia.

17. The plant or plant cell of any one of embodiments 12-16, wherein the plant or plant cell comprises enhanced resistance to a plant disease caused by at least one strain of PVY and/or PVA, relative to the resistance of a control plant.

18. The plant or plant cell of embodiment 17, wherein the plant or plant cell comprises enhanced resistance to plant disease(s) caused by at least two strains of PVY and/or PVA, relative to a control plant.

19. The plant or plant cell of any one of embodiments 12-18, wherein the plant or plant cell is a potato or tomato plant or plant cell.

20. A method for enhancing the resistance of a plant to a plant disease caused by at least one strain of PVY, at least one strain of PVA, and/or at least one potyvirus, the method comprising modifying at least one plant cell to comprise a heterologous polynucleotide, the heterologous polynucleotide comprising a nucleotide sequence selected from the group consisting of:

(a) the nucleotide sequence set forth in SEQ ID NO: 1, 6, 10, 12, or 13;

(b) a nucleotide sequence encoding the amino acid sequence set forth in SEQ ID NO: 2, 4, or 7;

(c) the nucleotide sequence set forth in SEQ ID NO: 3, 5, 8, 9, or 11;

(d) a nucleotide sequence having at least 90% sequence identity to at least one of the nucleotide sequences set forth in SEQ ID NOS: 1, 3, 5, 6, 8, 10, 12, and 13, wherein the nucleic acid molecule is capable of conferring resistance to a plant disease caused by at least one strain of PVY, at least one strain of PVA, and/or at least one potyvirus, relative to a control plant not comprising the nucleic acid molecule; and (e) a nucleic acid molecule comprising a nucleotide sequence encoding an amino acid sequence having at least 90% sequence identity to at least one of the amino acid sequences set forth in SEQ ID NO: 2, 4 and 7, wherein the nucleic acid molecule is capable of conferring resistance to a plant disease caused by at least one strain of PVY, at least one strain of PVA, and/or at least one potyvirus, relative to a control plant not comprising the nucleic acid molecule.

21. The method of embodiment 20, wherein the heterologous polynucleotide is stably incorporated into the genome of the plant cell.

22. The method of embodiment 20 or 21, wherein the plant cell is regenerated into a plant comprising in its genome the heterologous polynucleotide.

23. The method of any one of embodiments 20-22, wherein modifying at least one plant cell to comprise a heterologous polynucleotide comprises introducing the heterologous polynucleotide into at least one plant cell.

24. The method of any one of embodiments 20-23, wherein the heterologous polynucleotide comprises the nucleotide sequence of any one of (b)-(e) and further comprises a promoter operably linked for the expression of the nucleotide sequence in a plant.

25. The method of embodiment 24, wherein the promoter is selected from the group consisting of pathogen-inducible, constitutive, tissue-preferred, wound-inducible, and chemical-regulated promoters.

26. The method of any one of embodiments 20-22, wherein modifying at least one plant cell to comprise a heterologous polynucleotide comprises using genome editing to modify the nucleotide sequences of a native or non-native gene in the genome of the plant cell to comprise the nucleotide sequence of any one of (a)-(e).

27. The method of embodiment 26, wherein the modifying further comprise introducing a nucleic acid molecule into the plant cell, wherein the nucleic acid molecule comprises a nucleotide sequence comprising at least a part of the nucleotide sequence of any one of (a)-(e).

28. The method of embodiment 27, wherein at least a portion of the at least a part of the nucleotide sequence of the native or non-native gene is replaced with at least a part of the nucleotide sequence of the nucleic acid molecule.

29. The method of any one of embodiments 20-28, wherein the plant comprising the heterologous polynucleotide comprises enhanced resistance to a plant disease caused by at least one strain of PVY, at least one strain of PVA, and/or at least one potyvirus, relative to the resistance of a control plant.

30. The method of any one of embodiments 20-29, wherein the plant comprising the heterologous polynucleotide comprises enhanced resistance to plant disease(s) caused by at least two strains of PVY and/or PVA, relative to the resistance of a control plant.

31. The method of any one of embodiments 20-30, wherein the plant is selected from the group consisting of potato, tomato, eggplant, pepper, tomatillo, tobacco, and petunia.

32. A plant produced or producible by the method of any one of embodiments 20-31.

33. A fruit, tuber, leaf, or seed of the plant of any one of embodiments 9-19 and 32, wherein the fruit, tuber, leaf or seed comprises the heterologous polynucleotide.

34. A method of limiting a plant disease caused by at least one strain of PVY, at least one strain of PVA, and/or at least one potyvirus in agricultural crop production, the method comprising planting a seedling, tuber, or seed of the plant of any one of embodiments 9-19 and 32 and growing the seedling, tuber, or seed under conditions favorable for the growth and development of a plant resulting therefrom, wherein the seedling, tuber, or seed comprises the nucleic acid molecule, expression cassette, vector, or heterologous polynucleotide.

35. The method of embodiment 34, further comprising harvesting at least one fruit, tuber, leaf and/or seed from the plant, and optionally processing the harvested fruit, tuber, leaf, and/or seed into a food product.

36. A fruit, tuber, leaf, seed, or food product obtained or obtainable using the method of claim 35.

37. A method for identifying a solanaceous plant that comprises an R gene for a plant disease caused by at least one strain of PVY, at least one strain of PVA, and/or at least one potyvirus, the method comprising detecting in the plant, or in at least one part or cell thereof, the presence of: a c630 nucleotide sequence, a c516 nucleotide sequence, or a c630 nucleotide sequence and a c516 nucleotide sequence.

38. The method of embodiment 37, wherein the solanaceous plant comprises enhanced resistance to at plant disease(s) caused by at least two strains of PVY and/or PVA.

39. The method of embodiment 37 or 38, wherein the solanaceous plant is a potato or tomato plant.

40. The method of any one of embodiments 37-39, wherein the presence of the c630 nucleotide sequence is detected by detecting at least one marker within the c630 nucleotide sequence and wherein the presence of the c516 nucleotide sequence is detected by detecting at least one marker within the c516 nucleotide sequence.

41. The method of any one of embodiments 37-40, wherein the c630 nucleotide sequence comprises or consists of the nucleotide sequence set forth in SEQ ID NOS: 1, 3, 5, 10, or 12 and wherein the c516 nucleotide sequence comprises or consists of the nucleotide sequence set forth in SEQ ID NOS: 6, 8, or 12.

42. The method of any one of embodiments 37-41, wherein detecting the presence of the c630 and/or c516 nucleotide sequence comprises a member selected from the group consisting of PCR amplification, nucleic acid sequencing, nucleic acid hybridization, and an immunological assay for the detection of (i) either one or both of the R proteins encoded by the c630 nucleotide sequence and/or (ii) the R protein encoded by the c516 nucleotide sequence.

43. A solanaceous plant identified or indentifiable by the method of any one of embodiments 37-42.

44. The solanaceous plant of embodiment 43, wherein the solanaceous plant is selected from the group consisting of potato, tomato, eggplant, pepper, tomatillo, tobacco, and petunia.

45. A fruit, tuber, leaf, or seed of the solanaceous plant of embodiment 43 or 44.

46. A solanaceous plant or plant cell comprising c630 or c516, wherein the plant is not a *Solanum stoloniferum* plant or a *Solanum tuberosum* plant.

47. The solanaceous plant of embodiment 46, wherein the solanaceous plant comprises enhanced resistance to at least one strain of PVY and/or PVA.

48. A method for introducing c630 and/or c516 into a solanaceous plant, the method comprising:
  (a) crossing a first solanaceous plant comprising in its genome at least one copy of c630, c516, or both c630 and c516, with a second solanaceous plant lacking in its genome c630, c516, or both c630 and c516, respectively, whereby at least one progeny plant is produced; and
  (b) selecting at least one progeny plant comprising in its genome c630, c516, or both c630 and c516 by detecting in the progeny plant the presence of c630, c516, or both c630 and c516, respectively.

49. The method of embodiment 48, wherein the first solanaceous plant is a *S. stoloniferum* plant or a *S. tuberosum* plant and the second solanaceous plant is *S. tuberosum* plant lacking in its genome c630 and/or c516.

50. The method of embodiment 48 or 49, wherein c630 comprises or consists of a nucleotide sequence selected from the group consisting of the nucleotide sequences set forth in SEQ ID NOS: 1, 10, and 13.

51. The method of any one of embodiments 48-50, wherein c516 comprises or consists of a nucleotide sequence selected from the group consisting of the nucleotide sequences set forth in SEQ ID NOS: 6 and 12.

52. The method of any one of embodiments 48-51, wherein detecting in the progeny plant the presence of c630, c516, or both c630 and c516 comprises detecting in the progeny plant, or in at least one part or cell thereof, the presence of a c630 nucleotide sequence, a c516 nucleotide sequence, or a c630 nucleotide sequence and a c516 nucleotide sequence, respectively, using the method according to any one of embodiments 37-42.

53. The method of any one of embodiments 48-52, further comprising (i) backcrossing at least one selected progeny plant of (b) to a solanaceous plant that is of the same species and genotype as second solanaceous plant or of the same species as the second solanaceous plant and lacking in its genome c630, c516, or both c630 and c516, whereby at least one progeny plant is produced from the backcrossing; and (ii) selecting at least one progeny plant comprising in its genome c630, c516, or both c630 and c516 that is produced from the backcrossing of (i).

54. A progeny plant obtained or obtainable using the method of any one of embodiments 48-53.

55. The progeny plant of embodiment 54, wherein the progeny plant comprises enhanced resistance to at least one strain of PVY and/or PVA.

56. A fruit, tuber, leaf, or seed obtained or obtainable from the solanaceous plant of embodiment 54 or 55.

57. Use of the plant, fruit, tuber, leaf or seed of any one of embodiments 9-19, 32, 33, 43-47, and 54-56 in agriculture.

58. A human or animal food product comprising, or produced using, the plant, fruit, tuber, leaf, and/or seed of any one of embodiments 9-19, 32, 33, 43-47, and 54-56.

59. A polypeptide comprising an amino acid sequence selected from the group consisting of:
  (a) the amino acid sequence encoded by the nucleotide sequence set forth in SEQ ID NO: 2, 4, or 7;
  (b) the amino acid sequence encoded by the nucleotide sequence set forth in SEQ ID NO: 1, 3, 5, 6, 8, 9, 10, 11, 12, or 13; and
  (c) an amino acid sequence having at least 90% sequence identity to at least one of the amino acid sequences set forth in SEQ ID NO: 2, 4, and 7, wherein a polypeptide comprising the amino acid sequence is capable of conferring resistance to a plant disease caused by at least one strain of PVY, at least one strain of PVA, and/or at least one potyvirus, relative to a control plant not comprising the polypeptide the polypeptide.

Additional embodiments of the methods and compositions of the present invention are described elsewhere herein.

Preferred plants of the invention are solanaceous plants. As used herein, the term "solanaceous plant" refers to a plant that is a member of the Solanaceae family. Such solanaceous plants include, for example, domesticated and non-domesticated members of Solanaceae family. Solanaceous plants of the present invention include, but are not limited to, potato (*Solanum tuberosum*), eggplant (*Solanum melongena*), petunia (*Petunia* spp., e.g., *Petunia×hybrida* or *Petunia hybrida*), tomatillo (*Physalis philadelphica*), other *Physalis* spp., woody nightshade (*Solanum dulcamara*), garden huckleberry (*Solanum scabrum*), gboma eggplant (*Solanum macrocarpon*), pepper (*Capsicum* spp; e.g., *Capsicum annuum, C. baccatum, C. chinense, C. frutescens, C. pubescens*, and the like), tomato (*Solanum lycopersicum* or *Lycopersicon esculentum*), tobacco (*Nicotiana* spp., e.g. *N. tabacum, N benthamiana*), *Solanum americanum, Solanum demissum, Solanum stoloniferum, Solanum papita, Solanum bulbocastanum, Solanum edinense, Solanum schenckii, Solanum hjertingii, Solanum venturi, Solanum mochiquense, Solanum chacoense*, and *Solanum pimpinellifolium*. In preferred embodiments of the methods and compositions of the present invention, the solanaceous plants are solanaceous plants grown in agriculture including, but not limited to, potato, tomato, eggplant, pepper, tomatillo, tobacco and petunia. In more preferred embodiments, the solanaceous plants are potato and tomato. In even more preferred embodiments, the preferred plant is potato.

Other plants of interest for the methods and compositions of the present invention include, for example, any plant that is a host for PVY, PVA, and/or other Potyvirus. Such plants include, but are not limited to, plant species in the following plant families: Amaranthaceae (particularly in the subfamily Chenopodiaceae), Leguminosae, and Compositae.

Examples of other plant species of interest for the compositions and methods of the present invention include, but are not limited to, corn (*Zea mays*), *Brassica* sp. (e.g., *B.* napus, B. rapa, B. juncea), particularly those Brassica species useful as sources of seed oil, alfalfa (*Medicago sativa*), rice (*Oryza sativa*), rye (*Secale cereale*), triticale (×*Triticosecale* or *Triticum*×*Secale*) sorghum (*Sorghum bicolor, Sorghum vulgare*), teff (*Eragrostis* ten, millet (e.g., pearl millet (*Pennisetum glaucum*), proso millet (*Panicum miliaceum*), foxtail millet (*Setaria italica*), finger millet (*Eleusine coracana*)), switchgrass (*Panicum virgatum*), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), strawberry (e.g. *Fragaria× ananassa, Fragaria vesca, Fragaria moschata, Fragaria virginiana, Fragaria chiloensis*), sweet potato (*Ipomoea batatus*), yam (*Dioscorea* spp., *D. rotundata, D. cayenensis, D. alata, D. polystachya, D. bulbifera, D. esculenta, D. dumetorum, D. trifida*), cassava (*Manihot esculenta*), coffee (*Coffea* spp.), coconut (*Cocos nucifera*), oil palm (e.g. *Elaeis guineensis, Elaeis oleifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), date (*Phoenix dactylifera*), cultivated forms of *Beta vulgaris* (sugar beets, garden beets, chard or spinach beet, mangelwurzel or fodder beet), spinach (*Spinacia oleracea*), sugarcane (*Saccharum* spp.), quinoa (*Chenopodium quinoa*), oat (*Avena sativa*), barley (*Hordeum vulgare*), cannabis (*Cannabis sativa, C. indica, C. ruderalis*), poplar (*Populus* spp.), eucalyptus (*Eucalyptus* spp.), *Arabidopsis thaliana, Arabidopsis rhizogenes, Nicotiana benthamiana, Brachypodium distachyon* vegetables, ornamentals, and conifers and other trees. In specific embodiments, plants of the present invention are crop plants (e.g. maize, sorghum, wheat, millet, rice, barley, oats, sugarcane, alfalfa, soybean, peanut, sunflower, cotton, safflower, *Brassica* spp., lettuce, strawberry, apple, citrus, etc.).

Vegetables include tomatoes (*Lycopersicon esculentum*), eggplant (also known as "aubergine" or "brinjal") (*Solanum melongena*), pepper (*Capsicum annuum*), lettuce (e.g., *Lactuca sativa*), green beans (*Phaseolus vulgaris*), lima beans (*Phaseolus limensis*), peas (*Lathyrus* spp.), chickpeas (*Cicer arietinum*), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Fruit trees and related plants include, for example, apples, pears, peaches, plums, oranges, grapefruits, limes, pomelos, palms, and bananas. Nut trees and related plants include, for example, almonds, cashews, walnuts, pistachios, macadamia nuts, filberts, hazelnuts, and pecans.

The term "solanaceous plant" is intended to encompass solanaceous plants at any stage of maturity or development, as well as any cells, tissues or organs (plant parts) taken or derived from any such plant unless otherwise clearly indicated by context. Solanaceous plant parts include, but are not limited to, fruits, stems, tubers, roots, flowers, ovules, stamens, leaves, embryos, meristematic regions, callus tissue, anther cultures, gametophytes, sporophytes, pollen, microspores, protoplasts, and the like. As used herein, the term "tuber" is intended to mean a whole tuber or any part thereof such as, for example, a slice or a portion of potato tuber comprising one or more buds (i.e. "eyes") suitable for planting in a field to produce a potato plant. The present invention also includes seeds produced by the solanaceous plants of the present invention.

The present invention provides resistance nucleic acid molecules that are capable of conferring to a plant resistance to a plant disease caused by at least one plant pathogen, plants and plants cells comprising such nucleic acid molecules and related methods. Plant pathogens include, for example, viruses, bacteria, fungi, oomycetes, nematodes, and the like. Preferred plant pathogens of the present invention are viruses, particularly viruses in the family Potyviridae, more particularly viruses in the genus Potyvirus, most particularly PVY and PVA. Virus species of interest in the in the family Potyviridae include, but are not limited to, virus species in the following genera: *Potyvirus, Ipomovirus, Brambyvirus, Tritimovirus, Rymovirus, Bymovirus, Poacevirus*, and *Macluravirus*. Examples of Potyvirus species of interest for the compositions and methods of the present invention include, but are not limited to, Alstroemeria mosaic potyvirus, *Amaranthus* leaf mottle potyvirus, *Apium* virus Y, Araujia mosaic potyvirus, Arracacha Y potyvirus, Artichoke latent potyvirus, Asparagus 1 potyvirus, Banana bract mosaic potyvirus, Bean common mosaic necrosis potyvirus, Bean common mosaic potyvirus, Bean yellow mosaic potyvirus, Beet mosaic potyvirus, *Bidens* mosaic potyvirus, *Bidens* mottle virus, Brugmansia mosaic virus, Caladenia virus A, Canna yellow streak virus, Cardamom mosaic potyvirus, Carnation vein mottle potyvirus, Carrot thin leaf potyvirus, Cassava brown streak potyvirus, *Cassia* yellow spot potyvirus, Celery mosaic virus, Chickpea bushy dwarf potyvirus, Chickpea distortion mosaic potyvirus, Chilli ringspot virus [2], Chilli veinal mottle virus, Clitoria chlorosis virus, Clover yellow vein virus, Cocksfoot streak virus, *Commelina diffusa* potyvirus, *Commelina* mosaic virus, Cowpea green vein-banding potyvirus, Cowpea Moroccan aphid-borne mosaic potyvirus, Cowpea rugose mosaic potyvirus, *Crinum* mosaic potyvirus, Daphne Y potyvirus, Dasheen mosaic potyvirus, *Datura* Colombian potyvirus, *Datura* distortion mosaic potyvirus, *Datura* necrosis potyvirus, *Datura* shoestring potyvirus, Dendrobium mosaic potyvirus, *Desmodium* mosaic potyvirus, *Dioscorea alata* potyvirus, *Dioscorea* green banding mosaic potyvirus, Eggplant green mosaic potyvirus, *Euphorbia* ringspot potyvirus, Freesia mosaic potyvirus, Groundnut eyespot potyvirus, Guar symptomless potyvirus, Guinea grass mosaic potyvirus, Hardenbergia mosaic virus, Helenium Y potyvirus, Henbane mosaic potyvirus, *Hippeastrum* mosaic potyvirus, Hyacinth mosaic potyvirus, Iris *fulva* mosaic potyvirus, Iris mild mosaic potyvirus, Iris severe mosaic potyvirus, Japanese hornwort mosaic virus, Johnsongrass mosaic potyvirus, Kennedya Y potyvirus, Leek yellow stripe potyvirus, Lettuce mosaic potyvirus, Lily mottle potyvirus, Lupine potyvirus, Maize dwarf mosaic potyvirus, Malva vein clearing potyvirus, Marigold mottle potyvirus, *Narcissus* degeneration virus, *Narcissus* late season yellows virus, *Narcissus* yellow stripe virus, Nerine potyvirus, Onion yellow dwarf potyvirus, Ornithogalum mosaic potyvirus, *Papaya* ringspot potyvirus, Parsnip mosaic potyvirus, *Passiflora* ringspot potyvirus, *Passiflora* South African potyvirus, *Passiflora* virus Y, Passionfruit woodiness virus, Patchouli mosaic potyvirus, Pea mosaic potyvirus, Pea seed-borne mosaic potyvirus, Peanut green mosaic potyvirus, Peanut mottle virus, Pepper Indian mottle potyvirus, Pepper mottle virus, Pepper severe mosaic potyvirus, Pepper vein banding virus, Pepper veinal mottle potyvirus, Plum pox potyvirus, Pokeweed mosaic potyvirus, Potato virus A potyvirus, Potato virus V potyvirus, Potato virus Y, *Primula* mosaic potyvirus, *Ranunculus* mottle potyvirus, Shallot yellow stripe potyvirus, Sorghum mosaic potyvirus, Soybean mosaic virus, Statice Y potyvirus, Sugarcane mosaic virus, Sweet potato feathery mottle potyvirus, Sweet potato G potyvirus, Sweet potato latent virus, Swordbean distortion mosaic potyvirus, Sunflower chlorotic mottle virus, Tamarillo mosaic potyvirus, Telfairia mosaic potyvirus, Tobacco etch virus, Tobacco vein-banding mosaic potyvirus, Tobacco vein mottling potyvirus, Tobacco wilt potyvirus, Tomato Peru potyvirus, Tradescantia mosaic virus, Triteleia mosaic virus, *Tropaeolum* 1 potyvirus, *Tropaeolum* 2 potyvirus, Tuberose potyvirus, Tulip band-breaking potyvirus, Tobacco vein banding mosaic virus, Tulip breaking potyvirus, Tulip chlorotic blotch potyvirus, Turnip mosaic potyvirus, Tradescantia mosaic virus, Ullucus mosaic potyvirus, Vallota mosaic potyvirus, Vanilla mosaic potyvirus, Vanilla necrosis potyvirus, Voandzeia distortion mosaic potyvirus, Watermelon mosaic virus, Wild potato mosaic potyvirus, *Wisteria* vein mosaic potyvirus, Yam mosaic potyvirus, Zucchini yellow fleck potyvirus, Zucchini yellow mosaic virus, Asystasia gangetica mottle potyvirus, Celery latent potyvirus, *Datura* mosaic potyvirus, Endive necrotic mosaic potyvirus, Kalanchoe mosaic potyvirus, Konjak mosaic potyvirus, Nasturtium mosaic potyvirus, Patchouli mottle potyvirus, Shallot yellow stripe potyvirus, Sweet potato vein mosaic potyvirus, and Welsh onion yellow stripe potyvirus.

In preferred embodiments of the present invention, a nucleic acid molecule of an R gene is capable of conferring to a plant resistance to a plant disease caused by at least one potyvirus. In more preferred embodiments, a nucleic acid molecule of an R gene is capable of conferring to a plant resistance to a plant disease caused by at least one strain of PVY or PVA. In even more preferred embodiments, a nucleic acid molecule of an R gene is capable of conferring to a plant resistance to a plant disease caused by at least one strain of PVY and at least one strain of PVA. In yet even more preferred embodiments, a nucleic acid molecule of an R gene is capable of conferring to a plant resistance to a plant disease caused by multiple strains of PVY or PVA. In the most preferred embodiments, a nucleic acid molecule of an R gene is capable of conferring to a plant resistance to a plant disease caused by multiple strains of PVY and multiple strains of PVA.

In one embodiment of the invention, the nucleotide sequences encoding R proteins have at least about 75%, 80%, 85%, 90%, 91%, 92%, 93%, 94%, 95%, 96%, 97%, 98%, 99% or more sequence identity to the entire nucleotide sequence set forth in SEQ ID NO: 1 or 6, or to a fragment thereof. Such fragments include, for example, those comprising or consisting of the entire nucleotide sequence set forth in SEQ ID NO: 10, 12, or 13. In another embodiment of the invention, the nucleotide sequences encoding R proteins have at least about 75%, 80%, 85%, 90%, 91%, 92%, 93%, 94%, 95%, 96%, 97%, 98%, 99% or more sequence identity to the entire nucleotide sequence set forth in SEQ ID NO: 3, 5, and/or 8, or to a fragment thereof.

The present invention encompasses isolated or substantially purified polynucleotide (also referred to herein as "nucleic acid molecule", "nucleic acid" and the like) or protein (also referred to herein as "polypeptide") compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed polynucleotides and proteins encoded thereby are also encompassed by the present invention. By "fragment" is intended a portion of the polynucleotide or a portion of the amino acid sequence and hence protein encoded thereby. Fragments of polynucleotides comprising coding sequences may encode protein fragments that retain biological activity of the full-length or native protein. Alternatively, fragments of a polynucleotide that are useful as hybridization probes generally do not encode proteins that retain biological activity or do not retain promoter activity. Thus, fragments of a nucleotide sequence may range from at least about 20 nucleotides, about 50 nucleotides, about 100 nucleotides, and up to the full-length polynucleotide of the invention.

In certain embodiments of the invention, the fragments and variants of the disclosed polynucleotides and proteins encoded thereby are those that are capable of conferring to a plant resistance to a plant disease caused by at least one potyvirus, at least one strain of PVY, and/or at least one strain of PVA. Preferably, a polynucleotide comprising a fragment of a native R polynucleotide of the present invention is capable of conferring resistance to a plant disease caused by at least one potyvirus, at least one strain of PVY, and/or at least one strain of PVA to a plant comprising the polynucleotide. Likewise, a protein or polypeptide comprising a native R protein of the present invention is preferably capable of conferring resistance to a plant disease caused by at least one potyvirus, at least one strain of PVY, and/or at least one strain of PVA to a plant comprising the protein or polypeptide.

Polynucleotides that are fragments of a native R polynucleotide comprise at least 16, 20, 50, 75, 100, 125, 150, 175, 200, 250, 300, 400, 500, 1000, 2000, 3000, 4000, 5000, 6000, 7000, or 8000 contiguous nucleotides, or up to the number of nucleotides present in a full-length R polynucleotide disclosed herein (for example, 8335, 3315, 3774, 8206, 2817, 5065, 6232, and 7488 nucleotides for of SEQ ID NOS: 1, 3, 5, 6, 8, 10, 12, and 13 respectively).

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native"

polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the R proteins of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode an R protein of the invention. Generally, variants of a particular polynucleotide of the invention will have at least about 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein. In certain embodiments of the invention, variants of a particular polynucleotide of the invention will have at least about 75%, 80%, 85%, 90%, 91%, 92%, 93%, 94%, 95%, 96%, 97%, 98%, 99% or more sequence identity to at least one nucleotide sequence selected from the group consisting of SEQ ID NOS: 1, 3, 5, 6, 8, 10, 12, and 13, and optionally comprise a non-naturally occurring nucleotide sequence that differs from the nucleotide sequence set forth in SEQ ID NO: 1, 3, 5, 6, 8, 10, 12, and/or 13 by at least one nucleotide modification selected from the group consisting of the substitution of at least one nucleotide, the addition of at least one nucleotide, and the deletion of at least one nucleotide. It is understood that the addition of at least one nucleotide can be the addition of one or more nucleotides within a nucleotide sequence of the present invention (e.g. SEQ ID NO: 1, 3, 5, 6, 8, 10, 12, and 13), the addition of one or more nucleotides to the 5' end of a nucleotide sequence of the present invention, and/or the addition of one or more nucleotides to the 3' end of a nucleotide sequence of the present invention.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, a polynucleotide that encodes a polypeptide with a given percent sequence identity to at least one polypeptide having the amino acid sequence selected from the group consisting of SEQ ID NOS: 2, 4, and 7, is disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 60%, 65%, 70%, 75%, 80%, 85%, 90%, 91%, 92%, 93%, 94%, 95%, 96%, 97%, 98%, 99% or more sequence identity. In certain embodiments of the invention, variants of a particular polypeptide of the invention will have at least about 60%, 65%, 70%, 75%, 80%, 85%, 90%, 91%, 92%, 93%, 94%, 95%, 96%, 97%, 98%, 99% or more sequence identity to the amino acid sequence set forth in SEQ ID NO: 2, 4, or 7, and optionally comprises a non-naturally occurring amino acid sequence that differs from at least one amino acid sequence selected from the group consisting of SEQ ID NO: 2, 4, and 7 by at least one amino acid modification selected from the group consisting of the substitution of at least one amino acid, the addition of at least one amino acid, and the deletion of at least one amino acid. It is understood that the addition of at least one amino acid can be the addition of one or more amino acids within an amino acid sequence of the present invention (e.g. SEQ ID NO: 2, 4, or 7), the addition of one or more amino acids to the N-terminal end of an amino acid sequence of the present invention, and/or the addition of one or more amino acids to the C-terminal end of an amino acid sequence of the present invention.

"Variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Such variants may result from, for example, genetic polymorphism or from human manipulation. Biologically active variants of an R protein will have at least about 75%, 80%, 85%, 90%, 91%, 92%, 93%, 94%, 95%, 96%, 97%, 98%, 99% or more sequence identity to the amino acid sequence for the native protein (e.g. the amino acid sequence set forth in SEQ ID NO: 2, 4, or 7) as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant and other variant forms. Likewise, the proteins of the invention encompass naturally occurring proteins as well as variations and modified forms thereof. More preferably, such variants confer to a plant or part thereof comprising the variant enhanced resistance a plant disease caused by at least one strain of PVY and/or PVA. In some embodiments, the mutations that will be made in the DNA encoding the variant will not place the sequence out of reading frame. Optimally, the mutations will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assays that are disclosed herein below.

Variant polynucleotides and proteins also encompass sequences and proteins derived from a mutagenic and recombinogenic procedure such as DNA shuffling. Strategies for such DNA shuffling are known in the art. See, for example, Stemmer (1994) *Proc. Natl. Acad. Sci. USA* 91:10747-10751; Stemmer (1994) Nature 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that encode R proteins and which hybridize under stringent conditions to at least one of the R proteins disclosed herein or otherwise known in the art, or to variants or fragments thereof, are encompassed by the present invention.

In one embodiment, the orthologs of the present invention have coding sequences comprising at least 80%, 85%, 90%, 91%, 92%, 93%, 94%, 95%, 96%, 97%, 98%, 99%, or greater nucleotide sequence identity to at least one nucleotide sequence selected from the group consisting of the nucleotide sequences set forth in SEQ ID NOS: 1, 3, 5, 6, 8, 10, 12, and 13 and/or encode proteins comprising least 80%, 85%, 90%, 91%, 92%, 93%, 94%, 95%, 96%, 97%, 98%, 99%, or greater amino acid sequence identity to at least one amino acid sequence selected from the group consisting of the amino acid sequences set forth in SEQ ID NO: 2, 4, and 7.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the polynucleotides of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire polynucleotide disclosed herein, or one or more portions thereof, may be used as a probe capable of specifically hybridizing to corresponding polynucleotide and messenger RNAs. To achieve specific hybridization under a variety of conditions, such probes include sequences that are unique among the sequence of the gene or cDNA of interest sequences and are optimally at least about 10 nucleotides in length, and most optimally at least about 20 nucleotides in length. Such probes may be used to amplify corresponding polynucleotides for the particular gene of interest from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.). An extensive guide to the hybridization of nucleic acids is found in Tijssen (1993) *Laboratory Techniques in Biochemistry and Molecular Biology Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

It is recognized that the R protein coding sequences of the present invention encompass polynucleotide molecules comprising a nucleotide sequence that is sufficiently identical to the nucleotide sequence of any one or more of SEQ ID NOS: 1, 3, 5, 6, 8, 10, 12, and 13. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably 75% identity, more preferably 85%, 90%, 95%, 96%, 97%, 98% or 99% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to the polynucleotide molecules of the invention. BLAST protein searches can be performed with the XBLAST program, score=50, wordlength=3, to obtain amino acid sequences homologous to protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. BLAST, Gapped BLAST, and PSI-Blast, XBLAST and NBLAST are available on the World Wide Web at ncbi.nlm.nih.gov. Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. Alignment may also be performed manually by inspection.

Unless otherwise stated, sequence identity/similarity values provided herein refer to the value obtained using the full-length sequences of the invention and using multiple alignment by mean of the algorithm Clustal W (Nucleic Acid Research, 22(22):4673-4680, 1994) using the program AlignX included in the software package Vector NTI Suite Version 7 (InforMax, Inc., Bethesda, Md., USA) using the default parameters; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by CLUSTALW (Version 1.83) using default parameters (available at the European Bioinformatics Institute website on the World Wide Web at ebi.ac.uk/Tools/clustalw/index).

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The heterologous polynucleotides or polynucleotide constructs comprising R protein coding regions can be provided in expression cassettes for expression in the plant or other organism or non-human host cell of interest. The cassette will include 5' and 3' regulatory sequences operably linked to the R protein coding region. "Operably linked" is intended to mean a functional linkage between two or more elements. For example, an operable linkage between a polynucleotide or gene of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the R protein coding region to be under the transcriptional regulation of the regulatory regions. The expression cassette may additionally contain selectable marker genes.

The expression cassette will include in the 5'-3' direction of transcription, a transcriptional and translational initiation region (i.e., a promoter), a R protein coding region of the invention, and a transcriptional and translational termination region (i.e., termination region) functional in plants or other organism or non-human host cell. The regulatory regions (i.e., promoters, transcriptional regulatory regions, and translational termination regions) and/or the R protein coding region or of the invention may be native/analogous to the host cell or to each other. Alternatively, the regulatory regions and/or the R protein coding region of the invention may be heterologous to the host cell or to each other.

As used herein, "heterologous" in reference to a nucleic acid molecule, polynucleotide, nucleotide sequence, or polynucleotide construct is a nucleic acid molecule, polynucleotide, nucleotide sequence, or polynucleotide construct that originates from a foreign species, or, if from the same species, is modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

As used herein, a "native gene" is intended to mean a gene that is a naturally-occurring gene in its natural or native position in the genome of a plant. Such a native gene has not been genetically engineered or otherwise modified in nucleotide sequence and/or positon in the genome the plant through human intervention, nor has such a native gene been introduced into the genome of the plant via artificial methods such as, for example, plant transformation.

As used herein, a "non-native gene" is intended to mean a gene that has been introduced into a plant by artificial means and/or comprises a nucleotide sequence that is not naturally occurring in the plant. Non-native genes include, for example, a gene (e.g. an R gene) that is introduced into the plant by a plant transformation method. Additionally, when a native gene in the genome of a plant is modified, for example by a genome-editing method, to comprise a nucleotide sequence that is different (i.e. non-identical) from the nucleotide sequence of native gene, the modified gene is a non-native gene.

The present invention provides host cells comprising at least of the nucleic acid molecules, expression cassettes, and vectors of the present invention. In preferred embodiments of the invention, a host cells is plant cell. In other embodiments, a host cell is selected from the group consisting of a bacterium, a fungal cell, and an animal cell. In certain embodiments, a host cell is non-human animal cell. However, in some other embodiments, the host cell is an in-vitro cultured human cell.

While it may be optimal to express the R protein using heterologous promoters, the native promoter of the corresponding R gene may be used.

The termination region may be native with the transcriptional initiation region, may be native with the operably linked R protein coding region of interest, may be native with the plant host, or may be derived from another source (i.e., foreign or heterologous to the promoter, the R protein of interest, and/or the plant host), or any combination thereof. Convenient termination regions are available from the Ti-plasmid of *A. tumefaciens*, such as the octopine synthase (OCS) and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gown (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants. Such constitutive promoters include, for example, the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced expression of the R protein coding sequences within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) *Plant J.* 12(2):255-265; Kawamata et al. (1997) *Plant Cell Physiol.* 38(7):792-803; Hansen et al. (1997)*Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201;

Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Additionally, as pathogens find entry into plants through wounds or insect damage, a wound-inducible promoter may be used in the heterologous polynucleotides of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225: 1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-la promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992)*Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Act USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990)*Mot Cell. Biol.* 10:3343-3356; Zambretti et al. (1992) *Proc. Natl. Acad. Sci. USA* 89:3952-3956; Bairn et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not intended to be limiting. Any selectable marker gene can be used in the present invention.

Numerous plant transformation vectors and methods for transforming plants are available. See, for example, An, G. et al. (1986) *Plant Pysiol.*, 81:301-305; Fry, J., et al. (1987) *Plant Cell Rep.* 6:321-325; Block, M. (1988) *Theor. Appl Genet.* 76:767-774; Hinchee, et al. (1990) *Stadler. Genet. Symp.* 203212.203-212; Cousins, et al. (1991) *Aust. J. Plant Physiol.* 18:481-494; Chee, P. P. and Slightom, J. L. (1992) *Gene.* 118:255-260; Christou, et al. (1992) *Trends. Biotechnol.* 10:239-246; D'Halluin, et al. (1992) *Bio/Technol.* 10:309-314; Dhir, et al. (1992) *Plant Physiol.* 99:81-88; Casas et al. (1993) *Proc. Nat. Acad Sci. USA* 90:11212-11216; Christou, P. (1993) *In Vitro Cell. Dev. Biol.*-Plant; 29P:119-124; Davies, et al. (1993) *Plant Cell Rep.* 12:180-183; Dong, J. A. and Mchughen, A. (1993) *Plant Sci.* 91:139-148; Franklin, C. I. and Trieu, T. N. (1993) *Plant. Physiol.* 102:167; Golovkin, et al. (1993) *Plant Sci.* 90:41-52; Guo Chin Sci. Bull. 38:2072-2078; Asano, et al. (1994) *Plant Cell Rep.* 13; Ayeres N. M. and Park, W. D. (1994) *Crit. Rev. Plant. Sci.* 13:219-239; Barcelo, et al. (1994) *Plant. J.* 5:583-592; Becker, et al. (1994) *Plant. J* 5:299-307; Borkowska et al. (1994) *Acta. Physiol Plant.* 16:225-230; Christou, P. (1994) *Agro. Food. Ind. Hi Tech.* 5: 17-27; Eapen et al. (1994) *Plant Cell Rep.* 13:582-586; Hartman, et al. (1994) *Bio-Technology* 12: 919923; Ritala, et al. (1994) *Plant. Mol. Biol.* 24:317-325; and Wan, Y. C. and Lemaux, P. G. (1994) *Plant Physiol.* 104:3748.

The methods of the invention involve introducing a heterologous polynucleotide or polynucleotide construct into a plant. By "introducing" is intended presenting to the plant the heterologous polynucleotide or polynucleotide construct in such a manner that the construct gains access to the interior of a cell of the plant. The methods of the invention do not depend on a particular method for introducing a heterologous polynucleotide or polynucleotide construct to a plant, only that the heterologous polynucleotide or polynucleotide construct gains access to the interior of at least one cell of the plant. Methods for introducing heterologous polynucleotides or polynucleotide constructs into plants are known in the art including, but not limited to, stable transformation methods, transient transformation methods, and virus-mediated methods.

By "stable transformation" is intended that the heterologous polynucleotide or polynucleotide construct introduced into a plant integrates into the genome of the plant and is capable of being inherited by progeny thereof. By "transient transformation" is intended that a heterologous polynucleotide or polynucleotide construct introduced into a plant does not integrate into the genome of the plant. It is recognized that stable and transient transformation methods comprise introducing one or more nucleic acid molecules (e.g. DNA), particularly one or more recombinant nucleic acid molecules (e.g. recombinant DNA) into a plant, plant cell, or other host cell or organism.

For the transformation of plants and plant cells, the nucleotide sequences of the invention are inserted using standard techniques into any vector known in the art that is suitable for expression of the nucleotide sequences in a plant or plant cell. The selection of the vector depends on the preferred transformation technique and the target plant species to be transformed.

Methodologies for constructing plant expression cassettes and introducing foreign nucleic acids into plants are generally known in the art and have been previously described. For example, foreign DNA can be introduced into plants, using tumor-inducing (Ti) plasmid vectors. Other methods utilized for foreign DNA delivery involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et al.; Bilang et al. (1991) *Gene* 100: 247-250; Scheid et al., (1991)*Mol. Gen. Genet.,* 228: 104-112; Guerche et al., (1987) *Plant Science* 52: 111-116; Neuhause et al., (1987) *Theor. Appl Genet.* 75: 30-36; Klein et al., (1987) *Nature* 327: 70-73; Howell et al., (1980) *Science* 208:1265; Horsch et al., (1985) *Science* 227: 1229-1231; DeBlock et al., (1989) *Plant Physiology* 91: 694-701; *Methods for Plant Molecular Biology* (Weissbach and Weissbach, eds.) Academic Press, Inc. (1988) and *Methods in Plant Molecular Biology* (Schuler and Zielinski, eds.) Academic Press, Inc. (1989). The method of transformation depends upon the plant cell to be transformed, stability of vectors used, expression level of gene products and other parameters.

Other suitable methods of introducing nucleotide sequences into plant cells and subsequent insertion into the plant genome include microinjection as Crossway et al. (1986) *Biotechniques* 4:320-334, electroporation as described by Riggs et al. (1986) *Proc. Natl. Acad. Sci. USA* 83:5602-5606, *Agrobacterium*-mediated transformation as described by Townsend et al., U.S. Pat. No. 5,563,055, Zhao et al., U.S. Pat. No. 5,981,840, direct gene transfer as described by Paszkowski et al. (1984) *EMBO I* 3:2717-2722, and ballistic particle acceleration as described in, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lecl transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in The Experimental Manipulation of Ovule Tissues, ed. Chapman et al. (*Longman*, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The polynucleotides of the invention may be introduced into plants by contacting plants with a virus or viral nucleic acids. Generally, such methods involve incorporating a heterologous polynucleotide or polynucleotide construct of the invention within a viral DNA or RNA molecule. Further, it is recognized that promoters of the invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

If desired, the modified viruses or modified viral nucleic acids can be prepared in formulations. Such formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al. Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, antifreezing agents, for seed treatment formulation also optionally colorants and/or binders and/or gelling agents.

In specific embodiments, the polynucleotides, polynucleotide constructs, and expression cassettes of the invention can be provided to a plant using a variety of transient transformation methods known in the art. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *PNAS Sci.* 91: 2176-2180 and Hush et al. (1994) *J. Cell Science* 107:775-784, all of which are herein incorporated by reference. Alternatively, the polynucleotide can be transiently transformed into the plant using techniques known in the art. Such techniques include viral vector system and *Agrobacterium tumefaciens*-mediated transient expression as described elsewhere herein.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a heterologous polynucleotide or polynucleotide construct of the invention, for example, an expression cassette of the invention, stably incorporated into their genome.

Any methods known in the art for modifying DNA in the genome of a plant can be used to modify genomic nucleotide sequences in planta, for example, to create or insert a resistance gene or even to replace or modify an endogenous resistance gene or allele thereof. Such methods include, but are not limited to, genome-editing (or gene-editing) techniques, such as, for example, methods involving targeted mutagenesis, homologous recombination, and mutation breeding. Targeted mutagenesis or similar techniques are disclosed in U.S. Pat. Nos. 5,565,350; 5,731,181; 5,756,325; 5,760,012; 5,795,972, 5,871,984, and 8,106,259; all of which are herein incorporated in their entirety by reference. Methods for gene modification or gene replacement comprising homologous recombination can involve inducing double breaks in DNA using zinc-finger nucleases (ZFN), TAL (transcription activator-like) effector nucleases (TALEN), Clustered Regularly Interspaced Short Palindromic Repeats/CRISPR-associated nuclease (CRISPR/Cas nuclease), or homing endonucleases that have been engineered endonucleases to make double-strand breaks at specific recognition sequences in the genome of a plant, other organism, or host cell. See, for example, Durai et al., (2005) *Nucleic Acids Re.s* 33:5978-90; Mani et al. (2005) *Biochem. Biophys. Res. Comm.* 335:447-57; U.S. Pat. Nos. 7,163,824, 7,001,768, and 6,453,242; Arnould et al. (2006)*J Mol. Biol.* 355:443-58; Ashworth et al., (2006) *Nature* 441:656-9; Doyon et al. (2006) *J. Am. Chem. Soc.* 128:2477-84; Rosen et al., (2006) *Nucleic Acids Res.* 34:4791-800; and Smith et al., (2006) *Nucleic Acids Res.* 34:e149; U.S. Pat. App. Pub. No. 2009/0133152; and U.S. Pat. App. Pub. No. 2007/0117128; all of which are herein incorporated in their entirety by reference.

Unless stated otherwise or apparent from the context of a use, the term "gene replacement" is intended to mean the replacement of any portion of a first polynucleotide molecule or nucleic acid molecule (e.g. a chromosome) that involves homologous recombination with a second polynucleotide molecule or nucleic acid molecule using a genome-editing technique as disclosed elsewhere herein, whereby at least a part of the nucleotide sequence of the first polynucleotide molecule or nucleic acid molecule is replaced with the second polynucleotide molecule or nucleic acid molecule. It is recognized that such gene replacement can result in additions, deletions, and/or modifications in the nucleotide sequence of the first polynucleotide molecule or nucleic acid molecule and can involve the replacement of an entire gene or genes, the replacement of any part or parts of one gene, or the replacement of non-gene sequences in the first polynucleotide molecule or nucleic acid molecule.

TAL effector nucleases (TALENs) can be used to make double-strand breaks at specific recognition sequences in the genome of a plant for gene modification or gene replacement through homologous recombination. TAL effector nucleases are a class of sequence-specific nucleases that can be used to make double-strand breaks at specific target sequences in the genome of a plant or other organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) *PNAS* 10.1073/pnas.1013133107; Scholze & Boch (2010) *Virulence* 1:428-432; Christian et al. *Genetics* (2010) 186: 757-761; Li et al. (2010) *Nuc. Acids Res*. (2010) doi: 10.1093/nar/gkq704; and Miller et al. (2011) *Nat. Biotechnol.* 29:143-148; all of which are herein incorporated by reference.

The CRISPR/Cas nuclease system can also be used to make double-strand breaks at specific recognition sequences in the genome of a plant for gene modification or gene replacement through homologous recombination. The CRISPR/Cas nuclease is an RNA-guided (simple guide RNA, sgRNA in short) DNA endonuclease system performing sequence-specific double-stranded breaks in a DNA segment homologous to the designed RNA. It is possible to design the specificity of the sequence (Cho S. W. et al., *Nat. Biotechnol.* 31:230-232, 2013; Cong L. et al., *Science* 339: 819-823, 2013; Mali P. et al., *Science* 339:823-826, 2013; Feng Z. et al., *Cell Research* 1-4, 2013).

In addition, a ZFN can be used to make double-strand breaks at specific recognition sequences in the genome of a plant for gene modification or gene replacement through homologous recombination. The Zinc Finger Nuclease (ZFN) is a fusion protein comprising the part of the FokI restriction endonuclease protein responsible for DNA cleavage and a zinc finger protein which recognizes specific, designed genomic sequences and cleaves the double-stranded DNA at those sequences, thereby producing free DNA ends (Urnov et al. (2010) *Nat. Rev. Genet.* 11:636-46; Carroll (2011) *Genetics.* 188:773-82).

Breaking DNA using site specific nucleases, such as, for example, those described herein above, can increase the rate of homologous recombination in the region of the breakage. Thus, coupling of such effectors as described above with nucleases enables the generation of targeted changes in genomes which include additions, deletions and other modifications.

The nucleic acid molecules, expression cassettes, vectors, and heterologous polynucleotides of the present invention may be used for transformation and/or genome editing of any plant species, including, but not limited to, monocots and dicots.

As used herein, the term "plant" includes seeds, plant cells, plant protoplasts, plant cell tissue cultures from which plants can be regenerated, plant calli, plant clumps, and plant cells that are intact in plants or parts of plants such as embryos, pollen, ovules, seeds, tubers, propagules, leaves, flowers, branches, fruits, roots, root tips, anthers, and the like. Progeny, variants, and mutants of the regenerated plants are also included within the scope of the invention, provided that these parts comprise the introduced polynucleotides. As used herein, "progeny" and "progeny plant" comprise any subsequent generation of a plant whether resulting from sexual reproduction and/or asexual propagation, unless it is expressly stated otherwise or is apparent from the context of usage.

As used herein, the terms "transgenic plant" and "transformed plant" are equivalent terms that refer to a "plant" as described above, wherein the plant comprises a heterologous nucleic acid molecule, heterologous polynucleotide, or heterologous polynucleotide construct that is introduced into a plant by, for example, any of the stable and transient transformation methods disclosed elsewhere herein or otherwise known in the art. Such transgenic plants and transformed plants also refer, for example, the plant into which the heterologous nucleic acid molecule, heterologous polynucleotide, or heterologous polynucleotide construct was first introduced and also any of its progeny plants that comprise the heterologous nucleic acid molecule, heterologous polynucleotide, or heterologous polynucleotide construct.

In certain embodiments of the invention, the methods involve the planting of seedlings and/or tubers and then growing such seedlings and tubers so as to produce plants derived therefrom and optionally harvesting from the plants a plant part or parts. As used herein, a "seedling" refers to a less than fully mature plant that is typically grown in greenhouse or other controlled- or semi-controlled (e.g. a cold frame) environmental conditions before planting or replanting outdoors or in a greenhouse for the production a harvestable plant part, such as, for example, a tomato fruit, a potato tuber or a tobacco leaf. As used herein, a "tuber" refers to an entire tuber or part or parts thereof, unless stated otherwise or apparent from the context of use. A preferred tuber of the present invention is a potato tuber.

In the methods of the invention involving planting a tuber, a part of tuber preferably comprises a sufficient portion of the tuber whereby the part is capable of growing into a plant under favorable conditions for the growth and development of a plant derived from the tuber. It is recognized that such favorable conditions for the growth and development of crop plants, particularly solanaceous crop plants, are generally known in the art.

In some embodiments of the present invention, a plant cell is transformed with a heterologous polynucleotide encoding an R protein of the present invention. The term "expression" as used herein refers to the biosynthesis of a gene product, including the transcription and/or translation of said gene product. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide. Examples of heterologous polynucleotides and nucleic acid molecules that encode R proteins are described elsewhere herein.

The use of the terms "DNA" or "RNA" herein is not intended to limit the present invention to polynucleotide molecules comprising DNA or RNA. Those of ordinary skill in the art will recognize that the methods and compositions of the invention encompass polynucleotide molecules comprised of deoxyribonucleotides (i.e., DNA), ribonucleotides (i.e., RNA) or combinations of ribonucleotides and deoxyribonucleotides. Such deoxyribonucleotides and ribonucleotides include both naturally occurring molecules and synthetic analogues including, but not limited to, nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). The polynucleotide molecules of the invention also encompass all forms of polynucleotide molecules including, but not limited to, single-stranded forms, double-stranded forms, hairpins, stem-and-loop structures, and the like. Furthermore, it is understood by those of ordinary skill in the art that the nucleotide sequences disclosed herein also encompasses the complement of that exemplified nucleotide sequence.

The invention is drawn to compositions and methods for enhancing the resistance of a plant to plant disease, particularly to compositions and methods for enhancing the resistance of a plant to a plant disease caused by at least one potyvirus. By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened.

The following examples are offered by way of illustration and not by way of limitation.

EXAMPLES

Example 1: Mapping of $Ry_{sto}$ Gene from dH Alicja

To clone the $Ry_{sto}$ gene, we developed a diploid potato (2n=2x=24) mapping population by a cross between PVY-resistant, heterozygous dihaploid clone dH Alicja, and susceptible, diploid clone 83-3121. dH Alicja was obtained from potato cultivar Alicja via parthenogenesis.

The extreme resistance (ER) to PVY in dH Alicja was conferred by the gene $Ry_{sto}$ which was derived from clone MPI 55.957/54. The $Ry_{sto}$ gene in MPI 55.957/54 was derived from a Solanum stoloniferum accession that is in the pedigree MPI 55.957/54. This S. stoloniferum accession was from the wild Solanum spp. collection of Max Planck Institute (Ross (1958) "Resistenz züchtung gegen die Mosaik- and andere Viren der Kartoffel," in Handbuch der Pflanzenzüchtung, 2nd ed., Vol. III, Kappert and Rudorf, eds., Paul Parey, Berlin, pp 106-125).

The mapping population consisted of 391 F1 individuals, and was evaluated for resistance to PVY as described by Flis et al. ((2005) Molecular Breeding 15:95-101). The segregation ratio of resistant versus susceptible progeny in the mapping population deviated from the 1:1 ratio expected for the segregation of a single dominant gene and was distorted towards resistance (149 susceptible and 242 PVY-resistant F1 individuals).

Example 2: SMRT RenSeq Combined with Bulked Segregant Analysis (BSA) RenSeq on 160 Susceptible Plants Yields 12 Candidate Genes We hypothesized that the underlying PVY resistance genes encode a nucleotide binding-leucine rich repeat (NLR) protein. To predict candidate gene(s) for $Ry_{sto}$, we applied R gene enrichment and sequencing (RenSeq) combined with Illumina MiSeq 250 PE sequencing to 149 bulked susceptible plants from mapping population (BS), alongside with susceptible (S) and resistant (R) parent.

RenSeq (Jupe et al. (2013) *Plant J.* 76:530-544) is a method which allows one to capture and sequence all NLR-type of resistance genes in plants. We employed an SMRT RenSeq, an improved version of RenSeq, that enables one to prepare long, enriched libraries that are suitable for using Pacific Biosciences Single-Molecule Real Time (SMRT) sequencing. Combined with bulked segregant analysis (Michelmore et al. (1991) *PNAS* 88:9828-9823) and long-read sequencing, like the PacBio platform ("SMRT RenSeq") (Witek et al. (2016) *Nat. Biotechnol.* 34:656-660), SMRT RenSeq allows one to quickly predict a set of candidate genes without a necessity of developing and screening large mapping population or building BAC libraries. To generate high confidence de novo assembly of R-parent NLRs, we also carried out SMRT RenSeq on gDNA derived from the resistant clone dH Alicja. Reads obtained from SMRT RenSeq were assembled using Geneious 8.1.2 software as described previously (Witek et al. (2016) *Nat. Biotechnol.* 34: 656-660), resulting in 1,555 contigs. R, S and BS reads from Illumina 250PE were mapped to contigs derived from SMRT RenSeq assembly using BWA (Li & Durbin (2009) *Bioinformatics* 25:1754-1760), with default settings. SNP calling and candidate prediction was performed as described previously in Jupe et al. ((2013) *Plant J.* 76:530-544) and Witek et al. ((2016) *Nat. Biotechnol.* 34:656-660). Additionally, we looked for candidate NLRs showing presence/absence polymorphism between R and S parent, and linkage to resistance based on BS samples. Numbers of pair-end mapped reads to contigs derived from SMRT RenSeq assembly were calculated using TSL Galaxy built-in scripts (MacLean & Kamoun (2012) *Nat. Biotechnol.* 30:33-34) for each R, S and BS samples. Resulting data were sorted and visualized in Microsoft Excel software. As a presence/absence polymorphism, we considered contigs with at least 250 mapped reads from R parent, and less than 10% and 18% of that number for S and BS samples, respectively.

SNP calling and presence/absence polymorphism detection resulted in 12 candidate NLR genes linked to $Ry_{sto}$ resistance. Expression of all candidate genes was confirmed using cDNA data from R parent as described previously (Andolfo et al. (2016) *BMC Plant Biol.* 14:1-12; Witek et al. (2016) *Nat. Biotechnol.* 34:656-660). Four candidate genes belonged to coiled-coil (CC) class of NLR family (CNL), and remaining eight to Toll/interleukin-1 receptor homology (TIR) domain-containing NLRs (TNL). Interestingly, when using BWA mapping criteria described above, all NLR genes linked to Ry resistance show presence/absence polymorphism, what indicates that the whole interval was introgressed from *S. stoloniferum*.

Example 3: Comparative Analysis Identifies the Same NLRs as Candidate Genes for $Ry_{sto}$ Several studies positioned Ry resistance gene from *S. stoloniferum* on the most distal end of the long arm of chromosome 12 (Flis et al. (2005) *Molecular Breeding* 15:95-101; Song et al. (2005) *Theor. Appl. Genet.* 111:879-87; van Eck et al. (2017) *Theor. Appl. Genet.* 130:515-528), what corresponds to the region downstream of 58 Mb in the reference potato genome clone DM (The Potato Genome Sequencing Consortium (2011) *Nature* 475:189-195). This region contains 18 complete and partial NLR immune receptors from both CNL and TNL groups (Jupe et al. (2013) *Plant J.* 76:530-544). To identify the homologue sequences of these NLRs from dH Alicja (putative $Ry_{sto}$ gene), we looked for NLRs in SMRT RenSeq assembly as described by Witek et al. ((2016) *Nat. Biotechnol.* 34:656-660). We identified 33 NLRs, including all 12 NLRs previously detected as linked using RenSeq data. The remaining 21 genes did not show any linked polymorphism in RenSeq data, thus suggesting that they are in repulsion phase or are not linked. This in silico analysis pointed out that all selected candidates from SMRT RenSeq data localize to the distal end of chromosome 12, the same region where $Ry_{sto}$ was previously positioned.

Example 4: Transient Expression of Nine Expressed NLR Genes in *Nicotiana benthamiana* Reveals Two that can Restrict Virus Multiplication We cloned the predicted coding sequences of 9 candidate genes into a binary expression vector under control of 35S promoter, and transformed them into *Agrobacterium* as described by Witek et al. ((2016) *Nat. Biotechnol.* 34:656-660). These constructs were transiently expressed in *Nicotiana benthamiana* leaves by infiltrating *Agrobacterium* suspension at an absorbance ($OD_{600}$) of about 1.0, followed by $PVY^{NTN}$ (isolate NIB-NTN; GenBank: AJ585342.1) inoculation as described by Yin et al. ((2012) *J. Plant Prot. Res* 52: 214-19). Seven days after infection leaf samples were collected and levels of viral mRNA were measured with quantitative-RT-PCR as described previously by Pompe-Novak et al. ((2006) *Physiol. Mol. Plant. Pathol.* 67:237-47). This analysis showed that two of the candidate genes, namely c630 and c516 (SEQ ID NO: 1 and SEQ ID NO: 6, respectively), under the control of 35S promoter reduced virus multiplication and spreading compared to WT *N. benthamiana* plants and remaining candidate contigs (FIGS. 1A and 1B). Transient delivery of candidate c630 under its native promoter (over 2 kb, nucleotides 257 to 2518 of SEQ ID NO: 1) and terminator elements (over 1 kb for splice variant 1, nucleotides 6732 to 7745 and over 0.45 kb for splice variant 2, nucleotides 7280 to 7745, of SEQ ID NO: 1), followed by PVY infection, showed the same level of virus multiplication inhibition as the 35S::c630 construct (FIG. 1A).

We further tested the functionality of candidate contigs c630 and c516 by infiltrating them into *N. benthamiana* plants systemically infected with $PVY^{NTN}$ (isolate NIB-NTN) or PVX virus. Only the infiltration of c630 into plants carrying $PVY^{NTN}$ resulted in HR (FIG. 2, left), similar to a HR in control experiment, where Rx gene (Bendahmane et al. (1999) *Plant Cell* 5:781-791) was delivered to plants infected with PVX virus (FIG. 2, right). Infiltration of c516 or Rx into $PVY^{NTN}$ carrying plants did not result in visible symptoms of cell death (data not shown).

Example 5: c630 Recognizes Multiple Strains of PVY

To test if c630 and c516 can recognize other strains of PVY virus, we infected *N. benthamiana* plants with PVY isolates 0, N, N-Wilga, NIB-NTN and unrelated viruses (PVX and TMV(U1)) as controls. Two weeks later, leaves showing symptoms of viral infection were infiltrated with *Agrobacterium* carrying candidate contigs c630, c516 and an empty plasmid. Whereas infiltration of c516 only resulted in a weak HR in plants carrying less aggressive PVY strains 0 and N, c630 infiltration resulted in a strong HR in plants carrying all PVY strains (but not control PVX or TMV) (Table 2). No cell death was observed when plants were infiltrated with *Agrobacterium* carrying an empty vector. These experiments further verified contigs c630 and c516 as candidates for the functional $Ry_{sto}$ gene.

TABLE 2

Strength* of HR After Agrobacterium Transient Delivery
of Various Constructs into N. benthamiana Plants
Systemically Infected with PVY, PVX or TMV Viruses

| Virus | 35S::c516 | 35S::c630 | empty vector |
|---|---|---|---|
| 0 (LW) | + | ++ | − |
| N (Ny) | +/− | ++ | − |
| N-Wilga | − | ++ | − |
| NIB-NTN | − | ++ | − |
| PVX (strain 0) | − | − | − |
| TMV (U1) | − | − | − |

*Strength of HR response: − no HR; +/− weak HR; + HR (5 dpi); ++ strong HR (3 dpi).

Example 6: Nicotiana tabacum Plants Stably Transformed with c630 Restrict Systemic PVY Spread We constructed stable transgenic *Nicotiana tabacum* cv. Xanthi nc plants carrying candidate genes c630 and c516 under the control of 35S promoter or native regulatory elements, using *Agrobacterium* (strain LBA 4404) transformation method described in Horsch et al. ((1985) *Science* 227:1229-1231).

Seven-week-old *N. tabacum* 35S transgenic and WT control plants were inoculated with $PVY^{NTN}$ (isolate NIB-NTN) or mock treated with water. Five days after PVY inoculation, large necrotic spots were visible on all eight transgenic plants carrying c630 candidate gene (FIG. 3, left panel), while no macroscopic symptoms could be observed on WT plants (FIG. 3, right panel) or c516 transgenic (data not shown). While typical mosaic symptoms of PVY infection were observed at 14 dpi on WT-control (FIG. 4, bottom panel) and c516 plants, transgenic plants carrying c630 remained either symptomless for PVY (lines A, B, E; FIG. 4, top panel) or showed severe infections symptoms on upper leaves leading to systemic necrotization (lines C, D, F, G and H; FIG. 5). We speculated that the latter had partial resistance that resulted in systemic virus spread, HR of veins and ultimately death of the whole plants. Quantitative RT-PCR on upper, non-inoculated leaves of stable transgenic plants showed that systemic spread of the virus was fully restricted in lines A, B and E which remained symptomless for PVY (FIG. 6A), while viral mRNA levels in remaining transgenic plants were comparable to WT controls. These results were confirmed in F1 generation (FIG. 6B). Interestingly, in tobacco plants infected and maintained at elevated temperature (32° C.), candidate gene c630 was still preventing systemic infection. This result is consistent with findings that ER conferred by Ry-$f_{sto}$ is temperature independent (Flis et al. (2005) *Molecular Breeding* 15:95-101).

In four out of seven lines transformed with c630 candidate gene under control of native regulatory elements, we observed a local response at 7 dpi similar to that in 35S::c630 transgenic plants, and systemic leaves did not show any macroscopic symptoms. The absence of virus was confirmed with quantitative RT-PCR at 7 and 14 dpi. In three lines where expression of transgene was not detectable or low, PVY spread was not restricted (FIG. 7).

These results demonstrated that c630 can restrict systemic virus spreading in stable transgenic tobacco plants when expressed under both 35S and native regulatory elements.

Example 7: Solanum tuberosum Plants Stably Transformed with c630 Under the Control of 35S Promoter Restrict Systemic PVY Spread We constructed stable transgenic *Solanum tuberosum* cv. Maris Piper (MP) and cv. Russet Burbank (RB) plants carrying gene c630 under the control of 35S promoter and native regulatory elements, using the transformation method described in Mac et al. ((2004) *Cellular and Molecular Biology Letters* 9:843-53). Transgenic plants were infected with $PVY^{NTN}$ and virus spreading was monitored in upper, non-inoculated leaves 21 dpi using ELISA test with antibodies specific to PVY. In 10 out of 12 transgenic plants with the Maris Piper background that were tested, PVY was not detected (see Table 3); lack of virus was confirmed in 6wpi in three transgenic lines (A, F and N, Table 4). We additionally tested three transgenic lines (one susceptible, two resistant) using qPCR, which confirmed the results from ELISA test. The inhibition of virus multiplication and spreading in two resistant transgenic plants correlated with detectable levels of expression of the gene c630. In susceptible transgenic plants, the expression of the transgene was not detected.

TABLE 3

PVY Detection Using ELISA Test in Systemic Leaves
of MP Plants Transformed with 35S::c630

| Line name | $OD_{550}$ | Phenotype |
|---|---|---|
| MP WT | 1.917 | S |
| N. tabacum 630A | 0.012 | R |
| N. tabacum 630E | 0.002 | R |
| MP 630A* | 0.019 | R |
| MP 630B | 0.010 | R |
| MP 630C | 0.006 | R |
| MP 630F | 0.007 | R |
| MP 630H* | 1.706 | S |
| MP 630K* | 0.013 | R |
| MP 630N | 0.003 | R |
| MP 630P | 0.015 | R |
| MP 630 R | 0.022 | R |
| MP 630T | 0.011 | R |
| MP 630Z | 1.956 | S |

WT MP was used as a susceptible control, and two lines of *N. tabacum*/35S::c630 (A and E) as resistant controls.
Table shows average values from three plants for all MP lines except for F and Z, where two plants were tested.
The absorbance was measured at a wavelength of 550 nm ($OD_{550}$).
Asterisk indicates lines where presence (S phenotype) and absence (R phenotype) of the virus was validated with qPCR.

Similar results were obtained in a Russet Burbank background, where in all four tested transgenic lines carrying gene c630 under the control of 35S promoter, lack of PVY was confirmed with ELISA test (Table 4) and quantitative RT-PCR (FIG. 9) in systemic, non-inoculated leaves at 3 wpi. Additionally, since 11 dpi, we observed strong chlorosis symptoms on infected leaves of wild-type plants, while infected leaves of transgenic plants remained symptomless till at least 3 wpi (FIG. 8).

These results confirmed that c630 is conferring ER-type of resistance against PVY in stable transgenic potato lines cv. Maris Piper and Russet Burbank when expressed under 35S promoter and is a functional $Ry_{sto}$ resistance gene.

TABLE 4

PVY Detection Using ELISA Test in Systemic Leaves
of RB Plants Transformed with 35S::c630

| Line name | $OD_{550}$ | Phenotype |
|---|---|---|
| MP WT mock | 0.046 | R |
| MP WT | 2.495 | S |
| RB WT | 0.878 | S |
| MP 630A (6 wpi) | 0.002 | R |
| MP 630F (6 wpi) | 0.000 | R |
| MP 630N (6 wpi) | 0.000 | R |

TABLE 4-continued

PVY Detection Using ELISA Test in Systemic Leaves
of RB Plants Transformed with 35S::c630

| Line name | OD$_{550}$ | Phenotype |
|---|---|---|
| RB 630A | 0.006 | R |
| RB 630B | 0.010 | R |
| RB 630C | 0.006 | R |
| RB 630D | 0.003 | R |

WT MP and RB lines were used as a susceptible controls, and three lines of *S. tuberosum*/35S::c630 (A, F, N) as resistant controls (6 wpi).
Table shows average values from three plants for RB lines except A and B, average value from two plants for line D and single measurement for line C.
The absorbance was measured at a wavelength of 550 nm (OD$_{550}$).
Column three indicates plant phenotypes; S—susceptible, R—resistant.

Example 8: *Solanum tuberosum* Plants Stably Transformed with c630 Expressed Under Native Regulatory Sequences Restrict Systemic PVY Spread Stable transgenic *Solanum tuberosum* cv. Maris Piper plants expressing c630 under its native regulatory sequences were generated as described in Example 7. Four-week-old transgenic plants were infected with PVY$^{NTN}$ as described in Example 7. Three weeks after PVY inoculation, mRNA was isolated from upper, non-inoculated leaves. The PVY mRNA levels and the expression of c630 were quantified with qPCR, relative to the EF1 and Sec3 reference genes and expressed as means±SD calculated from three biological replicates per plant line. No PVY was detected in 5 lines expressing c630 (FIGS. 10A-10B).

The results shown in FIGS. 10A-10B demonstrate that the expression of c630 under control of its native regulatory sequences in potato plants from stable transgenic potato lines restricts systemic PVY spread in such plants.

Example 9: *Nicotiana tabacum* Plants Stably Transformed with c630 Restrict Systemic PVA Spread It was shown by Barker et al. ((1996) *Theor. Appl. Genet.* 93:710-716) that resistance to Potato virus A (PVA) is linked to PVY resistance mediated by Ry-f$_{sto}$. To test whether c630 also mediates resistance against PVA, we inoculated *Nicotiana tabacum*/35S::c630 plants with two strains of PVA (strains SASA and X Bonin). After 7 dpi, we observed HR on infected leaves of tobacco plants carrying 35S::c630 construct, and there was no local response in control tobacco plants for both the plants inoculated with SASA and X Bonin. FIG. 11 illustrates the results for leaves inoculated with SASA at 7 dpi. Similar results were obtained with leaves inoculated with X Bonin (not shown). Additionally, by 7 dpi, upper non-inoculated leaves of control plants showed typical mosaic symptoms of PVA infection and also stunted growth, while the *N. tabacum*/35S::c630 stably transformed plants remained healthy till at least 21 dpi (not shown). Western blotting analysis with anti-PVA antibodies and qPCR confirmed inhibition of PVA systemic spreading (not shown). These results demonstrate that c630 can confer resistance against multiple strains of PVA in addition to conferring resistance against multiple strains of PVY as disclosed above.

Upper non-inoculated leaves of control and transgenic plants carrying 35S::c630 are being tested for the presence of PVA using specific antibodies after 7, 14 and 21 dpi.

Example 10: c630 Undergoes Alternative Splicing

To annotate the coding sequence (CDS) of c630, we mapped RenSeq cDNA reads generated from R parent using TopHat (Trapnell et al. (2009) *Bionformatics* 25:1105-1111) with default settings. Mapping pattern suggests that the gene c630 undergoes alternative splicing and two splice forms differing at 3' end can be distinguished. The dominant transcript variant consists of 4 exons (SEQ ID NO: 3) encoding 1,105 amino acids (SEQ ID NO: 2), and is supported by 78-87% cDNA reads. Remaining reads support the presence of an additional intron at 3' end, starting 27 nucleotides (nt) upstream of STOP codon of splice variant 1, followed by additional exon encoding 162 amino acids (splice variant 2, SEQ ID NO: 5) resulting a total encoded protein length of 1,258 amino acids (SEQ ID NO: 4). The gene encoded by c630 has motifs and domains typical for TNL type of resistance gene; namely a TIR domain, followed by nucleotide binding (NB-ARC) domain and multiple leucine-reach repeats (LRR). Both splice variants share less than 34% identity on amino acid level with previously described TNL type resistance proteins from *Solanum* spp., including N (GeneBank: Q40392), Y-1 (GeneBank: CAC82812), Bs4 (GeneBank: AY438027), Grol-4 (GeneBank: AAP44390) and Pvr4 (GeneBank: KT359375), see Table 5.

TABLE 5

Full-length Amino Acid Identity (%) Between c630 (splice variant one) and Functional Solanaceae TNL Resistance Proteins

| | c630 | Grol-4 | Y-1 | Bs4 | N | Pvr4 |
|---|---|---|---|---|---|---|
| c630 | | 33.3 | 31.7 | 31.7 | 32.2 | 9.2 |
| Grol-4 | | | 34.4 | 36.1 | 35.7 | 10.4 |
| Y-1 | | | | 57.9 | 55.3 | 9.0 |
| Bs4 | | | | | 55.0 | 8.6 |
| N | | | | | | 9.7 |
| Pvr4 | | | | | | |

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An expression cassette or vector comprising a nucleotide sequence selected from the group consisting of:
   (a) the nucleotide sequence set forth in SEQ ID NO: 1, 3, 5, 10, or 13;
   (b) a nucleotide sequence encoding the amino acid sequence set forth in SEQ ID NO: 2 and/or 4;
   (c) a nucleotide sequence having at least 95% sequence identity to the nucleotide sequence set forth in SEQ ID NO: 10, wherein the nucleic acid molecule is capable of conferring resistance to a plant disease caused by at least one strain of PVY, at least one strain of PVA, and/or at least one potyvirus, relative to a control plant not comprising the nucleic acid molecule; and
   (d) a nucleic acid molecule comprising a nucleotide sequence encoding an amino acid sequence having at least 95% sequence identity to the amino acid sequence set forth in SEQ ID NO: 2 or 4 or both, wherein the nucleic acid molecule is capable of conferring resistance to a plant disease caused by at least one strain of PVY, at least one strain of PVA, and/or at least one potyvirus, relative to a control plant not comprising the nucleic acid molecule.

2. A host cell or a plant transformed with an expression cassette or vector comprising a nucleotide sequence selected from the group consisting of:
   (a) the nucleotide sequence set forth in SEQ ID NO: 1, 3, 5, 10, or 13;
   (b) a nucleotide sequence encoding the amino acid sequence set forth in SEQ ID NO: 2 and/or 4;
   (c) a nucleotide sequence having at least 95% sequence identity to the nucleotide sequence set forth in SEQ ID NO: 10, wherein the nucleic acid molecule is capable of conferring resistance to a plant disease caused by at least one stain of PVY, at least one strain of PVA, and/or at least one potyvirus, relative to a control plant not comprising the nucleic acid molecule; and
   (d) a nucleic acid molecule comprising a nucleotide sequence encoding an amino acid sequence having at least 95% sequence identity to the amino acid sequence set forth in SEQ ID NO: 2 or 4 or both, wherein the nucleic acid molecule is capable of conferring resistance to a plant disease caused by at least one strain of PVY, at least one strain of PVA, and/or at least one potyvirus, relative to a control plant not comprising the nucleic acid molecule.

3. A plant or plant cell comprising stably incorporated in its genome a heterologous polynucleotide comprising a nucleotide sequence selected from the group consisting of:
   (a) the nucleotide sequence set forth in SEQ ID NO: 1, 3, 5, 10, or 13;
   (b) a nucleotide sequence encoding the amino acid sequence set forth in SEQ ID NO: 2 and/or 4;
   (c) a nucleotide sequence having at least 95% sequence identity to the nucleotide sequence set forth in SEQ ID NO: 10, wherein the nucleic acid molecule is capable of conferring resistance to a plant disease caused by at least one strain of PVY, at least one strain of PVA, and/or at least one potyvirus, relative to a control plant not comprising the nucleic acid molecule; and
   (d) a nucleic acid molecule comprising a nucleotide sequence encoding an amino acid sequence having at least 95% sequence identity to the amino acid sequence set forth in SEQ ID NO: 2 or 4 or both, wherein the nucleic acid molecule is capable of conferring resistance to a plant disease caused by at least one strain of PVY, at least one strain of PVA, and/or at least one potyvirus, relative to a control plant not comprising the nucleic acid molecule.

4. The plant or plant cell of claim 3, wherein the heterologous polynucleotide comprises the nucleotide sequence of any one of (b)-(e) and further comprises a promoter operably linked for the expression of the nucleotide sequence in a plant.

5. A method for enhancing the resistance of a plant to a plant disease caused by at least one strain of PVY, at least one strain of PVA, and/or at least one potyvirus, the method comprising modifying at least one plant cell to comprise a heterologous polynucleotide, the heterologous polynucleotide comprising a nucleotide sequence selected from the group consisting of:
   (a) the nucleotide sequence set forth in SEQ ID NO: 1, 3, 5, 10, or 13;
   (b) a nucleotide sequence encoding the amino acid sequence set forth in SEQ ID NO: 2 and/or 4;
   (c) a nucleotide sequence having at least 95% sequence identity to the nucleotide sequence set forth in SEQ ID NO: 10, wherein the nucleic acid molecule is capable of conferring resistance to a plant disease caused by at least one strain of PVY, at least one strain of PVA, and/or at least one potyvirus, relative to a control plant not comprising the nucleic acid molecule; and
   (d) a nucleic acid molecule comprising a nucleotide sequence encoding an amino acid sequence having at least 95% sequence identity to the amino acid sequence set forth in SEQ ID NO: 2 or 4 or both, wherein the nucleic acid molecule is capable of conferring resistance to a plant disease caused by at least one strain of PVY, at least one strain of PVA, and/or at least one potyvirus, relative to a control plant not comprising the nucleic acid molecule.

6. The method of claim 5, wherein the heterologous polynucleotide is stably incorporated into the genome of the plant cell, and/or wherein the plant cell is regenerated into a plant comprising in its genome the heterologous polynucleotide.

7. The method of claim 5, wherein modifying at least one plant cell to comprise a heterologous polynucleotide comprises introducing the heterologous polynucleotide into at least one plant cell.

8. The method of claim 5, wherein the heterologous polynucleotide comprises the nucleotide sequence of any one of (b)-(e) and further comprises a promoter operably linked for the expression of the nucleotide sequence in a plant.

9. The method of claim 5, wherein modifying at least one plant cell to comprise a heterologous polynucleotide comprises using genome editing to modify the nucleotide sequences of a native or non-native gene in the genome of the plant cell to comprise the nucleotide sequence of any one of (a)-(e).

10. The method of claim 9, wherein the modifying further comprise introducing a nucleic acid molecule into the plant cell, wherein the nucleic acid molecule comprises a nucleotide sequence comprising at least a part of the nucleotide sequence of any one of (a)-(e).

11. A fruit, tuber, leaf, or seed of the plant of claim 3, wherein the fruit, tuber, leaf or seed comprises the heterologous polynucleotide.

12. A method of limiting a plant disease caused by at least one strain of PVY, at least one strain of PVA, and/or at least one potyvirus in agricultural crop production, the method comprising:
(a) planting a seedling, tuber, or seed of a plant, comprising stably incorporated in its genome a heterologous polynucleotide comprising a nucleotide sequence selected from the group consisting of
  (i) the nucleotide sequence set forth in SEQ ID NO: 1, 3, 5, 10, or 13,
  (ii) a nucleotide sequence encoding the amino acid sequence set forth in SEQ ID NO: 2 and/or 4,
  (iii) a nucleotide sequence having at least 95% sequence identity to the nucleotide sequence set forth in SEQ ID NO: 10, wherein the nucleic acid molecule is capable of conferring resistance to a plant disease caused by at least one strain of PVY, at least one strain of PVA, and/or at least one potyvirus, relative to a control plant not comprising the nucleic acid molecule, and
  (iv) a nucleic acid molecule comprising a nucleotide sequence encoding an amino acid sequence having at least 95% sequence identity to the amino acid sequence set forth in SEQ ID NO: 2 or 4 or both, wherein the nucleic acid molecule is capable of conferring resistance to a plant disease caused by at least one strain of PVY, at least one strain of PVA, and/or at least one potyvirus, relative to a control plant not comprising the nucleic acid molecule; and
(b) growing the seedling, tuber, or seed under conditions favorable for the growth and development of a plant resulting therefrom, wherein the seedling, tuber, or seed comprises the nucleic acid molecule, expression cassette, vector, or heterologous polynucleotide.

13. The method of claim 12, further comprising harvesting at least one fruit, tuber, leaf, and/or seed from the plant, and optionally processing the harvested fruit, tuber, leaf, and/or seed into a food product.

14. A human or animal food product comprising a plant or a fruit, tuber, leaf, and/or seed of the plant, wherein the plant comprises stably incorporated in its genome a heterologous polynucleotide comprising a nucleotide sequence selected from the group consisting of:
(a) the nucleotide sequence set forth in SEQ ID NO: 1, 3, 5, 10, or 13;
(b) a nucleotide sequence encoding the amino acid sequence set forth in SEQ ID NO: 2 and/or 4;
a nucleotide sequence having at least 95% sequence identity to the nucleotide sequence set forth in SEQ ID NO: 10, wherein the nucleic acid molecule is capable of conferring resistance to a plant disease caused by at least one strain of PVY, at least one strain of PVA, and/or at least one potyvirus, relative to a control plant not comprising the nucleic acid molecule; and
(d) a nucleic acid molecule comprising a nucleotide sequence encoding an amino acid sequence having at least 95% sequence identity to the amino acid sequence set forth in SEQ ID NO: 2 or 4 or both, wherein the nucleic acid molecule is capable of conferring resistance to a plant disease caused by at least one strain of PVY, at least one strain of PVA, and/or at least one potyvirus, relative to a control plant not comprising the nucleic acid molecule;
wherein the fruit, tuber, leaf, and seed comprise the heterologous polynucleotide.

15. The plant or plant cell of claim 3, wherein the plant or plant cell is selected from the group consisting of potato, tomato, eggplant, pepper, tomatillo, tobacco, petunia, soybean, fruit trees, and *Brassicca* spp.

16. The method of claim 5, wherein the plant or plant cell is selected from the group consisting of potato, tomato, eggplant, pepper, tomatillo, tobacco, petunia, soybean, fruit trees, and *Brassica* spp.

17. The method of claim 12, wherein the plant or plant cell is selected from the group consisting of potato, tomato, eggplant, pepper, tomatillo, tobacco, petunia, soybean, fruit trees, and *Brassica* spp.

* * * * *

SEQUENCE LISTING

<160> NUMBER OF SEQ ID NOS: 13

<210> SEQ ID NO 1
<211> LENGTH: 8335
<212> TYPE: DNA
<213> ORGANISM: Solanum stoloniferum

<400> SEQUENCE: 1

| | | | | | |
|---|---|---|---|---|---|
| ggtacctctg | gcttgactat | aggtgccatt | tagaccaatt | aggaactgaa | taagtctttg | 60 |
| atcctataaa | gacttagaga | ttttggattt | tccattacaa | acgcagacac | aagaacaagt | 120 |
| aatatctgca | tttaaagagt | ccaactcatc | ccataaatgt | ttcaatttag | tgaaataacc | 180 |
| tgatatatca | gaattacctt | gcactaatcc | attaagttcc | ttttgaaggt | gaaaaagctt | 240 |
| ggtaccatta | gacttaccaa | acctttgttc | gaggctatcc | caaagctcct | tagctgtgtt | 300 |
| ggaatagatg | acactatctc | caatctcttt | ggacaatgag | ttgagtaacc | aagaggttac | 360 |
| catgtcatta | caacaattcc | attgagaaga | atcagaagca | tcgaaaactg | gtgcttaaca | 420 |
| ggttccattg | atgaagccta | gcttcctctt | aactgaaaga | gctatcaaga | tcgatctcct | 480 |
| ctaaccagga | aaacctcgtc | catcaaccac | agtgcttatg | aggttcattc | taggagaatc | 540 |
| agagggtga | agataataag | ggtgactgga | gtccatagca | gatgctgcag | gtgcaacaat | 600 |
| ggttccagga | ttgttggagg | gtgatgaaga | atctctcatt | gtagatgatg | agtgaatgtg | 660 |
| aattggatcg | agcttactgc | tttgatacca | tgttataaat | gtaggagacg | tttgtggaaa | 720 |
| ttttctgata | atctattgat | catcatcttc | aatctatata | tacaagtatt | ctgtgcaaga | 780 |
| aaatacaaaa | aaatcacagc | tgtacacttg | tctaaatctt | gtagaaatat | tctaacaacc | 840 |
| taactaattt | tattccatcc | tatgttgata | tagtgtgctg | ctcacgtgct | cttcttcatt | 900 |
| tctttcattc | tgcaagatga | gtggaaatta | tgtttgccaa | caaaaattca | agttaagggg | 960 |
| taaggttgcg | tacacatcat | ccgtttgtga | attttactaa | gatatgttgt | ccttgaatca | 1020 |
| ttttctgtga | ttgttataac | ttacgcgtac | attagcataa | ggtggatttt | cattttttaat | 1080 |
| tcaaaatatc | taaatgattc | ggcagtcaca | tagattggtc | aaatagttgt | ggtactaaca | 1140 |
| tgttaagttt | agcaatttaa | ttatcgatga | attattatac | atttgaacca | agaaaaaaga | 1200 |
| gagttgttat | acatattaaa | ttgaattatt | taatggttga | gtaaattttt | aattttgtta | 1260 |
| aaaagaggat | aatttatat | gtaaaaggta | attttgattt | gaagagacat | ttttaatttg | 1320 |
| ataattaatg | tattaaaaat | aatttggaag | gatagataat | ttattatcat | tctcaacaag | 1380 |
| ttagcttttg | ggtgtggttc | tcccaggtca | gtctttcttt | tctgcttttt | ctgtgttttc | 1440 |
| ttctaaattg | ttacgaaatt | tttcttcaat | ttcttaggta | gggcaacgaa | tttatatcaa | 1500 |
| tttacacaaa | ggtatcaatt | tctgttcatt | tgtttaattt | gtcagtgcaa | tactgaaaaa | 1560 |
| aggtacattt | ttatgtcatg | aattaggaag | atgataacaa | gtttcctata | gagactgaaa | 1620 |
| aaaggtaaag | tctttactct | ttgtgaacac | aataagtttg | ctggaaattt | ctaagaagtt | 1680 |
| ggtcccccatt | gaacaatgat | cctgcatttg | aacttcatta | gaggttggac | ccatttgatg | 1740 |
| ggtgaccgaa | accttggaag | tcctcgtatt | gcatctcttc | ttatgtcatt | aatttcgatc | 1800 |
| atattacaat | aaagtgtttt | aaaaagtaaa | aatgtaatga | ctttaatttc | tcacaataat | 1860 |
| gaatacctag | gatacagttt | tatgatttga | aataggaaga | tgttaagaag | ttctcataaa | 1920 |
| aggtgtggcc | tagtggtcaa | tgaagtggtt | gagagccatg | aggtctcagg | ttcaacttcc | 1980 |
| aacggagaca | aaaatattag | gtaattcttc | ccatctatcc | tagccctagc | cctggtggac | 2040 |
| agagtcatct | ggtacttgct | gttggtgaat | ggaaaagata | gttgttttta | gaagattatt | 2100 |

```
agtaaacgta ctaattgatt tatcaacata actgatggga ttatgaagtg gcttgtggag    2160
ttagtcgaga agtgctcaag ctgacctaga tactaactac taataagaaa agaacaattg    2220
atgtgagtca ccattagttg agccatttc tctagaggag gaataattca aagatgctac    2280
ggagaagatt caaagatggt gggatgaatt tgctaatatg aaagcatgat gtaaaagaa    2340 ctagtaagta aactttcttt ttctttgtgt ttgttggtgg ggcctttcat aagaagttgg    2400
acccattcac aataatgcat gttgcagaca gagtgtggaa aaatgtatat aactacaaat    2460
atgtggtgct aagaagactt catatcagat acgcgtcttt agcaatattc ttcaacaatg    2520
tctcatgctt cttcttccaa agtttgcaag tacgatatct ttttgagttt tagaggtgaa    2580
gatacacgta gaaacttcgt gagtcatctt tataatgctt tagaacagag aggactccat    2640
gctttcaaag acgatgagcg gttggaagca ggaaaatcaa tttctgctga acttttaaaa    2700
gccatagaag aggccagatt cgctgtcgta atattttcaa aaagctatgc atcgtcaaga    2760
tggtgtttag aggagcttgc acacatcata agtgtaaaa aggaattgga gcagattgtg    2820
attccagtct tctatgatgt gagtccatca gatgtacgcc atcaaaatcc cctttcgct    2880 gtttcatttt cccaacatga ggaaaaatgc aaagatgata tggagaaggt tcaaagatgg    2940 agggcgcat ttgcggaggc agggaaaata tcaggctatc atttactaaa tttcaagtaa    3000
gccttctttt ttctttttt tcgggtttct ctttatcaag aggaaaaagg accaaacttt    3060
tagccaaaaa ggaacaaaga tcctaggaaa acagaaacgt atatgattgt ttgatgatgt    3120
aattagattt aaaatgtta taattcataa ttgacattat tatgtgtttg ttttagatat    3180
tagtctatga caagtctttg cttttctatt tatttacttt gagattattt tccactgtaa    3240
cgtagggatg aggccaagtg cgtcaagaaa ctagttgatg acatatttcc taagtcactt    3300
caaattattt caccttcc ggaaagctta gtgggtatga atctcaggt tgagaaagta    3360 acctcattat tagatatgga atcaaacgat gttcgctcta ttggtatttg gggtatgggc    3420
ggcatcggca aaacagaaat tgcaaatgtt ctacatcaaa gataccgcca tcaatttgac    3480
gctgattgtt ttcttggtga tgttggaaaa cttcatcaga aaaatggact aacgtggcta    3540
caacaagtcg tcatttgcaa gctcttgggt gaaaaattga ctctaactag tgagcatgaa    3600
gggatgaata ttttaaagaa tatgcttcgc tggaagaaag ttctgttcac catcgatgac    3660
gtaaaccatc aagaacagtt ggaatttttg gttggagagc cagagtggtt tggtaggggt    3720
agcagaatta ttttaacagc aagagacaag cacctattaa tcagtcacgt tggggataat    3780
gtgtatgaag tccaactatt atctgagaat gaagcacttg aattgttcag tagacatgct    3840
tttagagaaa gatcaccaaa agaagatttt atggaacttt caagacaagt ggtgaagcat    3900
gctggtggac tcccttagc tcttaaagtt ttgggttctt catttacgg acgagacaaa    3960 aagcactgga gacacataat tgatcggctg aagagaatcc ctcacaagga tattctagga    4020
aagcttaggc ttagttttga tggtctggac aaagatgaga aggaattatt tctggatatt    4080
gtatttctag agattgcatg cttgagtgga tatgatttta atatttatgt ggaacaagta    4140
cagagatatg tgagtcgtgg tttactaatt tattaccta ttgaaaaatc tctgttatcc    4200
atcgactgga gtaatagtat tgtgattcat aatatgataa gagaaatggg agaaaatgtc    4260
atacgggaag agtacgctaa cagcagaata tggcttcccg aggagatttg tgatcttttt    4320
aaagggaagt tggtaagcaa tatttaacgt aattaataat ttcataagct cttagttctg    4380
ttaatttatt ttgtttcatt tttatttgtt agtcattaaa tattgtttca ttttttacag    4440
```

```
ataacagaaa aggtggaaag cctatgtatt ccaaaagagt actattttga agatgatctt    4500
gtcaattata gcaatatttt caagaggatg caaagcttaa aaacactcat agttggtgat    4560 ggaacttta gcacaaactg cactatcact tatcttcctt ccagcctgcg gttcattgat     4620
tggaaagggt atccttcaat ttcattgcca gagagctttg aaccatcaca gcttgtggtg    4680
ctttgtttat ataaaagtag gcttgttgaa ctttggccaa tatcaaggt aacactctct     4740 tacaaatatt agacatcaac tggagttgtt gcaaagttct tgtacagaat aatggaataa    4800
taattctgaa caaatagttg taattataga atatcatgta tataatgagg ttgaaataaa    4860
tgttttgata ggccaatgca tgtaaattaa tccatccatg atttaaatgc tactttaaat    4920
aaatgttctg atatacacaa ttaacaccaa atttttattt attttggtt atcagtcacg      4980 gcataaggcc cataaatatt tttacttttc caatatttta aaaaattaaa tcttataaaa    5040
agttacgata ttaaagaggt tttgttttca ttatgaaatt aaaagaaaag aaatatatat    5100 ttggattta agacaattat gtatctcaaa agttcttttc cggattagct accgccttta     5160
gtgatcataa caaccttatc ttctctttat cttttttcc tacaaaatat ttctattagg     5220
agtactactt aagctcactg tgtttttttt tttttttttt gaaacagaaa ttgagcaact    5280
tgaagcattt ggatctcatg gacagctgtg agttaagaaa aaccctaat tttggtgata     5340 tgccaaactt ggagacacta attttacacg ggtgtgtgaa tttggaagag gtccatccct   5400
ctcttggaca gtgcagagtg cttacttatt tgagtttgga aggttgtcgc aaacttaaga   5460
agcttccaaa atttgtctgc gtggaatctc ttgagactct caatctcctt gaatgcacaa   5520
gcttacaaga atttccagaa atctgtggag atatgcatcg cttatcgacg ctcgatgtag   5580
gatccccctg gataagaagc ttaccccat ctctcagcgg ccttagatat ttgcaattga    5640
ctgagtgtgc agttcttgaa agtattccgg acgccattca aaatcttaga tatctcagta   5700
ttttagattg caataaactt gcaacactgc caaacagcct cttgaatca cagcaattgg    5760 aatatctttt aatacaccga tgttctggat tggtaaagct ccccttatct cttggagttc    5820
aaaagattct ccgttggtta agtatagatg gatgtgagaa cttaaagaag cttccaagct   5880
cgattcagat gaaatccctt caaagtctct ggatatctga ttccccaaaa ttagacacat   5940
ttccagaaat caatggagat atgcattact tggaaatact gtctctgaag tctactggga   6000
taagagaagt gccttcatcc attgggaatc tgagcggcct cactgatcta agtcttacag    6060
gttgtgaaga tcttctaagt ctaccagaca gcctctgcaa tttgatgaaa cttcgaagtc    6120
tttacctcga cgggtgcaaa aagctagaga agcttccaga aaacattggt gatttgcaag    6180
atttacataa acttgatgcg agcgatactg caatctccca accaccttcc tccatcacta    6240
agcttggcaa actgtggaag ttacgattct cacatgaaaa acaacttcaa tattcctcaa    6300
gttttgtctt gaatcaagta tcaggtttat cgtccttgac atcacttgat cttaataatc    6360
acaacatatt gagtggactt cctgaggatt taggatcttt gcagtctttg gaaaaactga    6420
gtctaagtgg aagcaatatt tcttgtttac caaaaagctt caaaggactc ttacaccttc    6480
agcatctgaa tgtacaattc tgtcagaatc ttaataaatt gcccggagag ctaccccaa     6540 atttaaagga gctatgtgta gattatcatt tagccttaat gagcatcaga gatctcgtaa    6600
ttcattatcc taagctgtgt aggcttggga tatccgactg tggagccgtc tcaagtgaac    6660
aagttaatgt gttcctacaa tatttttatca ggacatgcat ccaggttttt atcttatata   6720
tgaaatgttg aatattctcg tcaaattgat tgatttctag tagtaataat aatttctatt    6780
ctattgcatg cagtttgact ttctccaaag agattatttt ctcattttt ttcctgatca     6840
```

-continued

```
agtcagaatt tcagagttgt ttgattatga tcggtttaca aatcaaaaag agatgtcaat  6900
tgatctgaac ccatcttggt ataccgataa attcatgggt ttttggataa gttatggtct  6960
tactacactg aactcacaa gattagaagc tacattggtc tgcaaatctg accctgaaag  7020
aaaatattcc ttgaagtata actactttgg acaattgtgt atcgagtctc cttccatttg  7080
ttgcttctac ataccatttg aaacactgtg gaatgcttct ggcaataaag aagggaagaa  7140
tccaaatgat tattacatgt tggaggtatc taataggtac agtctggaga agaacgatg  7200
ctggggaatt cgcctggagt atgaaaagga ggaggcaatg agtgatactg gtcgtccaaa  7260
aaagaaaagg aagcaatgag tgatgcaaag gtccttgttt tacatcacaa tatttaaatg  7320
ttctttattt ctttcttaaa ttccgtactc aaccaaacac gtctcataaa attgtatgga  7380
aagaatatgt tctatattgt tgatacaatt tgtatatgag gggtttgtat cgatgataga  7440
tagatgaatt ttttttttt tataatgttg ttttttgagt ttgaaacaac ttctttacac  7500
ttataataag gtagatacgt tgagtatcca acatcctttc aagatttcac tagatatgtt  7560
gttgtttgag tcattttcta tgtgattgtt ataacttacg catgagcata tatctaagat  7620
attttgcaaa taaatatta tctataaaga tagtttcaaa attcgattcc ataaactttg  7680
atcaaggaag aaaatgtata taataatc aattttgatg attgctcaac ttttttctctg  7740
gccctttat ttcttatatt tttatactaa aaataaaga aaatataaa aataaaaaac  7800
tcaaataata ataaacaaat atatatat ggggaaatat ttaacactca aattaagtgt  7860
taagtcacaa aagtcaaaaa agaaaaatca tgtgtgggaa aaatcctttg ctaaaataat  7920
tatatgtacc cctacatgaa tttatattcc cttttttccat tagaggaaaa tgatacacgt  7980
gaaccactt aatgatgaga atatatatga accatatgtc agtcacttat ttattcttat  8040
tctttctttc tttttctttt tctactttct tttcttttct tttctactta tatagaagtg  8100
tgggttaagt tgttggtatt aacacgtatg tttattgtta ataaattcaa aatcaaggat  8160
agttttgagt ttttatgttt aggctttctc cttttttttt atttaatatt tagacatttg  8220
atagatgtcc aatacttctg taattccttc catttttagat ttacatgtca tttattttt  8280
ccgttaagtt ttacttgttt actatattaa aaaaaataat aataataata ataat        8335
```

<210> SEQ ID NO 2
<211> LENGTH: 1105
<212> TYPE: PRT
<213> ORGANISM: Solanum stoloniferum

<400> SEQUENCE: 2

```
Met Ser His Ala Ser Ser Ser Lys Val Cys Lys Tyr Asp Ile Phe Leu
1               5                   10                  15

Ser Phe Arg Gly Glu Asp Thr Arg Arg Asn Phe Val Ser His Leu Tyr
            20                  25                  30

Asn Ala Leu Glu Gln Arg Gly Leu His Ala Phe Lys Asp Asp Glu Arg
        35                  40                  45

Leu Glu Ala Gly Lys Ser Ile Ser Ala Glu Leu Leu Lys Ala Ile Glu
    50                  55                  60

Glu Ala Arg Phe Ala Val Val Ile Phe Ser Lys Ser Tyr Ala Ser Ser
65                  70                  75                  80

Arg Trp Cys Leu Glu Glu Leu Ala His Ile Ile Lys Cys Lys Lys Glu
                85                  90                  95

Leu Glu Gln Ile Val Ile Pro Val Phe Tyr Asp Val Ser Pro Ser Asp
            100                 105                 110
```

```
Val Arg His Gln Asn Pro Pro Phe Ala Val Ser Phe Ser Gln His Glu
        115                 120                 125

Glu Lys Cys Lys Asp Asp Met Glu Lys Val Gln Arg Trp Arg Gly Ala
        130                 135                 140

Phe Ala Glu Ala Gly Lys Ile Ser Gly Tyr His Leu Leu Asn Phe Lys
145                 150                 155                 160

Asp Glu Ala Lys Cys Val Lys Lys Leu Val Asp Asp Ile Phe Pro Lys
                165                 170                 175

Ser Leu Gln Ile Ile Ser Pro Phe Pro Glu Ser Leu Val Gly Met Lys
            180                 185                 190

Ser Gln Val Glu Lys Val Thr Ser Leu Leu Asp Met Glu Ser Asn Asp
        195                 200                 205

Val Arg Ser Ile Gly Ile Trp Gly Met Gly Gly Ile Gly Lys Thr Glu
        210                 215                 220

Ile Ala Asn Val Leu His Gln Arg Tyr Arg His Gln Phe Asp Ala Asp
225                 230                 235                 240

Cys Phe Leu Gly Asp Val Gly Lys Leu His Gln Lys Asn Gly Leu Thr
                245                 250                 255

Trp Leu Gln Gln Val Val Ile Cys Lys Leu Leu Gly Glu Lys Leu Thr
            260                 265                 270

Leu Thr Ser Glu His Glu Gly Met Asn Ile Leu Lys Asn Met Leu Arg
        275                 280                 285

Trp Lys Lys Val Leu Phe Thr Ile Asp Asp Val Asn His Gln Glu Gln
        290                 295                 300

Leu Glu Phe Leu Val Gly Glu Pro Glu Trp Phe Gly Arg Gly Ser Arg
305                 310                 315                 320

Ile Ile Leu Thr Ala Arg Asp Lys His Leu Leu Ile Ser His Val Gly
                325                 330                 335

Asp Asn Val Tyr Glu Val Gln Leu Leu Ser Glu Asn Glu Ala Leu Glu
            340                 345                 350

Leu Phe Ser Arg His Ala Phe Arg Glu Arg Ser Pro Lys Glu Asp Phe
        355                 360                 365

Met Glu Leu Ser Arg Gln Val Val Lys His Ala Gly Gly Leu Pro Leu
        370                 375                 380

Ala Leu Lys Val Leu Gly Ser Ser Phe Tyr Gly Arg Asp Lys Lys His
385                 390                 395                 400

Trp Arg His Ile Ile Asp Arg Leu Lys Arg Ile Pro His Lys Asp Ile
                405                 410                 415

Leu Gly Lys Leu Arg Leu Ser Phe Asp Gly Leu Asp Lys Asp Glu Lys
            420                 425                 430

Glu Leu Phe Leu Asp Ile Val Phe Leu Glu Ile Ala Cys Leu Ser Gly
        435                 440                 445

Tyr Asp Phe Asn Ile Tyr Val Glu Gln Val Gln Arg Tyr Val Ser Arg
450                 455                 460

Gly Leu Leu Ile Tyr Tyr Leu Ile Glu Lys Ser Leu Leu Ser Ile Asp
465                 470                 475                 480

Trp Ser Asn Ser Ile Val Ile His Asn Met Ile Arg Glu Met Gly Glu
                485                 490                 495

Asn Val Ile Arg Glu Glu Tyr Ala Asn Ser Arg Ile Trp Leu Pro Glu
            500                 505                 510

Glu Ile Cys Asp Leu Phe Lys Gly Lys Leu Ile Thr Glu Lys Val Glu
        515                 520                 525
```

```
Ser Leu Cys Ile Pro Lys Glu Tyr Tyr Phe Glu Asp Leu Val Asn
    530                 535                 540

Tyr Ser Asn Ile Phe Lys Arg Met Gln Ser Leu Lys Thr Leu Ile Val
545                 550                 555                 560

Gly Asp Gly Thr Phe Ser Thr Asn Cys Thr Ile Thr Tyr Leu Pro Ser
                565                 570                 575

Ser Leu Arg Phe Ile Asp Trp Lys Gly Tyr Pro Ser Ile Ser Leu Pro
            580                 585                 590

Glu Ser Phe Glu Pro Ser Gln Leu Val Val Leu Cys Leu Tyr Lys Ser
        595                 600                 605

Arg Leu Val Glu Leu Trp Pro Ile Ser Lys Lys Leu Ser Asn Leu Lys
    610                 615                 620

His Leu Asp Leu Met Asp Ser Cys Glu Leu Arg Lys Thr Pro Asn Phe
625                 630                 635                 640

Gly Asp Met Pro Asn Leu Glu Thr Leu Ile Leu His Gly Cys Val Asn
                645                 650                 655

Leu Glu Glu Val His Pro Ser Leu Gly Gln Cys Arg Val Leu Thr Tyr
            660                 665                 670

Leu Ser Leu Glu Gly Cys Arg Lys Leu Lys Lys Leu Pro Lys Phe Val
        675                 680                 685

Cys Val Glu Ser Leu Glu Thr Leu Asn Leu Leu Glu Cys Thr Ser Leu
    690                 695                 700

Gln Glu Phe Pro Glu Ile Cys Gly Asp Met His Arg Leu Ser Thr Leu
705                 710                 715                 720

Asp Val Gly Ser Pro Trp Ile Arg Ser Leu Pro Pro Ser Leu Ser Gly
                725                 730                 735

Leu Arg Tyr Leu Gln Leu Thr Glu Cys Ala Val Leu Glu Ser Ile Pro
            740                 745                 750

Asp Ala Ile Gln Asn Leu Arg Tyr Leu Ser Ile Leu Asp Cys Asn Lys
        755                 760                 765

Leu Ala Thr Leu Pro Asn Ser Leu Phe Glu Ser Gln Gln Leu Glu Tyr
    770                 775                 780

Leu Leu Ile His Arg Cys Ser Gly Leu Val Lys Leu Pro Leu Ser Leu
785                 790                 795                 800

Gly Val Gln Lys Ile Leu Arg Trp Leu Ser Ile Asp Gly Cys Glu Asn
                805                 810                 815

Leu Lys Lys Leu Pro Ser Ser Ile Gln Met Lys Ser Leu Gln Ser Leu
            820                 825                 830

Trp Ile Ser Asp Ser Pro Lys Leu Asp Thr Phe Pro Glu Ile Asn Gly
        835                 840                 845

Asp Met His Tyr Leu Glu Ile Leu Ser Leu Lys Ser Thr Gly Ile Arg
    850                 855                 860

Glu Val Pro Ser Ser Ile Gly Asn Leu Ser Gly Leu Thr Asp Leu Ser
865                 870                 875                 880

Leu Thr Gly Cys Glu Asp Leu Leu Ser Leu Pro Asp Ser Leu Cys Asn
                885                 890                 895

Leu Met Lys Leu Arg Ser Leu Tyr Leu Asp Gly Cys Lys Lys Leu Glu
            900                 905                 910

Lys Leu Pro Glu Asn Ile Gly Asp Leu Gln Asp Leu His Lys Leu Asp
        915                 920                 925

Ala Ser Asp Thr Ala Ile Ser Gln Pro Pro Ser Ser Ile Thr Lys Leu
    930                 935                 940

Gly Lys Leu Trp Lys Leu Arg Phe Ser His Glu Lys Gln Leu Gln Tyr
```

```
                      945             950            955            960
      Ser  Ser  Ser  Phe  Val  Leu  Asn  Gln  Val  Ser  Gly  Leu  Ser  Ser  Leu  Thr
                                 965             970            975

Ser  Leu  Asp  Leu  Asn  Asn  His  Asn  Ile  Leu  Ser  Gly  Leu  Pro  Glu  Asp
                      980             985            990

Leu  Gly  Ser  Leu  Gln  Ser  Leu  Glu  Lys  Leu  Ser  Leu  Ser  Gly  Ser  Asn
                 995            1000           1005

Ile  Ser  Cys  Leu  Pro  Lys  Ser  Phe  Lys  Gly  Leu  Leu  His  Leu  Gln
            1010           1015           1020

His  Leu  Asn  Val  Gln  Phe  Cys  Gln  Asn  Leu  Asn  Lys  Leu  Pro  Gly
            1025           1030           1035

Glu  Leu  Pro  Pro  Asn  Leu  Lys  Glu  Leu  Cys  Val  Asp  Tyr  His  Leu
            1040           1045           1050

Ala  Leu  Met  Ser  Ile  Arg  Asp  Leu  Val  Ile  His  Tyr  Pro  Lys  Leu
            1055           1060           1065

Cys  Arg  Leu  Gly  Ile  Ser  Asp  Cys  Gly  Ala  Val  Ser  Ser  Glu  Gln
            1070           1075           1080

Val  Asn  Val  Phe  Leu  Gln  Tyr  Phe  Ile  Arg  Thr  Cys  Ile  Gln  Val
            1085           1090           1095

Phe  Ile  Leu  Tyr  Met  Lys  Cys
            1100           1105
```

<210> SEQ ID NO 3
<211> LENGTH: 3315
<212> TYPE: DNA
<213> ORGANISM: Solanum stoloniferum

<400> SEQUENCE: 3

```
atgtctcatg cttcttcttc caaagtttgc aagtacgata tcttttttgag ttttagaggt      60
gaagatacac gtagaaactt cgtgagtcat ctttataatg ctttagaaca gagaggactc     120
catgctttca aagacgatga gcggttggaa gcaggaaaat caatttctgc tgaactttta     180
aaagccatag aagaggccag attcgctgtc gtaatatttt caaaaagcta tgcatcgtca     240
agatggtgtt tagaggagct tgcacacatc ataaagtgta aaaaggaatt ggagcagatt     300
gtgattccag tcttctatga tgtgagtcca tcagatgtac gccatcaaaa tccccctttc     360
gctgtttcat tttcccaaca tgaggaaaaa tgcaaagatg atatggagaa ggttcaaaga     420
tggaggggcg catttgcgga ggcagggaaa atatcaggct atcatttact aaatttcaag     480
gatgaggcca agtgcgtcaa gaaactagtt gatgacatat ttcctaagtc acttcaaatt     540
atttcacctt tcccggaaag cttagtgggt atgaaatctc aggttgagaa gtaacctca      600
ttattagata tggaatcaaa cgatgttcgc tctattggta tttggggtat gggcggcatc     660
ggcaaaacag aaattgcaaa tgttctacat caaagatacc gccatcaatt tgacgctgat     720
tgttttcttg gtgatgttgg aaaacttcat cagaaaaatg gactaacgtg gctacaacaa     780
gtcgtcattt gcaagctctt gggtgaaaaa ttgactctaa ctagtgagca tgaagggatg     840
aatattttaa agaatatgct tcgctggaag aaagttctgt tcaccatcga tgacgtaaac     900
catcaagaac agttggaatt tttggttgga gagccagagt ggtttggtag ggtagcaga      960
attattttaa cagcaagaga caagcaccta ttaatcagtc acgttgggga taatgtgtat    1020
gaagtccaac tattatctga gaatgaagca cttgaattgt tcagtagaca tgcttttaga    1080
gaaagatcac caaagaaga ttttatggaa ctttcaagac aagtggtgaa gcatgctggt    1140
ggactccctt tagctcttaa agttttgggt tcttcatttt acggacgaga caaaaagcac    1200
```

```
tggagacaca taattgatcg gctgaagaga atccctcaca aggatattct aggaaagctt    1260
aggcttagtt ttgatggtct ggacaaagat gagaaggaat tatttctgga tattgtattt    1320
ctagagattg catgcttgag tggatatgat tttaatattt atgtggaaca agtacagaga    1380
tatgtgagtc gtggtttact aatttattac cttattgaaa aatctctgtt atccatcgac    1440
tggagtaata gtattgtgat tcataatatg ataagagaaa tgggagaaaa tgtcatacgg    1500
gaagagtacg ctaacagcag aatatggctt cccgaggaga tttgtgatct ttttaaaggg    1560
aagttgataa cagaaaaggt ggaaagccta tgtattccaa agagtactat ttttgaagat    1620
gatcttgtca attatagcaa tattttcaag aggatgcaaa gcttaaaaac actcatagtt    1680
ggtgatggaa cttttagcac aaactgcact atcacttatc ttccttccag cctgcggttc    1740
attgattgga aagggtatcc ttcaatttca ttgccagaga gctttgaacc atcacagctt    1800
gtggtgcttt gtttatataa aagtaggctt gttgaacttt ggccaatatc aaagaaattg    1860
agcaacttga agcatttgga tctcatggac agctgtgagt taagaaaaac ccctaatttt    1920
ggtgatatgc caaacttgga gacactaatt ttacacgggt gtgtgaattt ggaagaggtc    1980
catccctctc ttggacagtg cagagtgctt acttatttga gtttggaagg ttgtcgcaaa    2040
cttaagaagc ttccaaaatt tgtctgcgtg gaatctcttg agactctcaa tctccttgaa    2100
tgcacaagct acaagaatt ccagaaatc tgtggagata tgcatcgctt atcgacgctc    2160
gatgtaggat ccccctggat aagaagctta ccccatctc tcagcggcct agatatttg    2220 caattgactg agtgtgcagt tcttgaaagt attccggacg ccattcaaaa tcttagatat    2280
ctcagtattt tagattgcaa taaacttgca acactgccaa acagcctctt tgaatcacag    2340
caattggaat atctttttaat acaccgatgt tctggattgg taaagctccc cttatctctt    2400
ggagttcaaa agattctccg ttggttaagt atagatggat gtgagaactt aaagaagctt    2460
ccaagctcga ttcagatgaa atcccttcaa agtctctgga tatctgattc cccaaaatta    2520
gacacatttc cagaaatcaa tggagatatg cattacttgg aaatactgtc tctgaagtct    2580
actgggataa gagaagtgcc ttcatccatt gggaatctga gcggcctcac tgatctaagt    2640
cttacaggtt gtgaagatct tctaagtcta ccagacagcc tctgcaattt gatgaaactt    2700
cgaagtcttt acctcgacgg gtgcaaaaag ctagagaagc ttccagaaaa cattggtgat    2760
ttgcaagatt tacataaact tgatgcgagc gatactgcaa tctcccaacc accttcctcc    2820
atcactaagc ttggcaaaact gtggaagtta cgattctcac atgaaaaaca acttcaatat    2880
tcctcaagtt ttgtcttgaa tcaagtatca ggtttatcgt ccttgacatc acttgatctt    2940
aataatcaca acatattgag tggacttcct gaggatttag gatctttgca gtctttggaa    3000
aaactgagtc taagtggaag caatatttct tgtttaccaa aaagcttcaa aggactctta    3060
caccttcagc atctgaatgt acaattctgt cagaatctta ataaattgcc cggagagcta    3120
cccccaaatt taaaggagct atgtgtagat tatcatttag ccttaatgag catcagagat    3180
ctcgtaattc attatcctaa gctgtgtagg cttgggatat ccgactgtgg agccgtctca    3240
agtgaacaag ttaatgtgtt cctacaatat tttatcagga catgcatcca ggtttttatc    3300
ttatatatga aatgt                                                     3315
```

<210> SEQ ID NO 4
<211> LENGTH: 1258
<212> TYPE: PRT
<213> ORGANISM: Solanum stoloniferum

```
<400> SEQUENCE: 4

Met Ser His Ala Ser Ser Lys Val Cys Lys Tyr Asp Ile Phe Leu
1               5                   10                  15

Ser Phe Arg Gly Glu Asp Thr Arg Arg Asn Phe Val Ser His Leu Tyr
            20                  25                  30

Asn Ala Leu Glu Gln Arg Gly Leu His Ala Phe Lys Asp Asp Glu Arg
            35                  40                  45

Leu Glu Ala Gly Lys Ser Ile Ser Ala Glu Leu Leu Lys Ala Ile Glu
        50                  55                  60

Glu Ala Arg Phe Ala Val Val Ile Phe Ser Lys Ser Tyr Ala Ser Ser
65                  70                  75                  80

Arg Trp Cys Leu Glu Glu Leu Ala His Ile Ile Lys Cys Lys Lys Glu
                85                  90                  95

Leu Glu Gln Ile Val Ile Pro Val Phe Tyr Asp Val Ser Pro Ser Asp
            100                 105                 110

Val Arg His Gln Asn Pro Pro Phe Ala Val Ser Phe Ser Gln His Glu
            115                 120                 125

Glu Lys Cys Lys Asp Asp Met Glu Lys Val Gln Arg Trp Arg Gly Ala
        130                 135                 140

Phe Ala Glu Ala Gly Lys Ile Ser Gly Tyr His Leu Leu Asn Phe Lys
145                 150                 155                 160

Asp Glu Ala Lys Cys Val Lys Lys Leu Val Asp Asp Ile Phe Pro Lys
                165                 170                 175

Ser Leu Gln Ile Ile Ser Pro Phe Pro Glu Ser Leu Val Gly Met Lys
            180                 185                 190

Ser Gln Val Glu Lys Val Thr Ser Leu Leu Asp Met Glu Ser Asn Asp
        195                 200                 205

Val Arg Ser Ile Gly Ile Trp Gly Met Gly Gly Ile Gly Lys Thr Glu
210                 215                 220

Ile Ala Asn Val Leu His Gln Arg Tyr Arg His Gln Phe Asp Ala Asp
225                 230                 235                 240

Cys Phe Leu Gly Asp Val Gly Lys Leu His Gln Lys Asn Gly Leu Thr
                245                 250                 255

Trp Leu Gln Gln Val Val Ile Cys Lys Leu Leu Gly Glu Lys Leu Thr
            260                 265                 270

Leu Thr Ser Glu His Glu Gly Met Asn Ile Leu Lys Asn Met Leu Arg
        275                 280                 285

Trp Lys Lys Val Leu Phe Thr Ile Asp Asp Val Asn His Gln Glu Gln
290                 295                 300

Leu Glu Phe Leu Val Gly Glu Pro Glu Trp Phe Gly Arg Gly Ser Arg
305                 310                 315                 320

Ile Ile Leu Thr Ala Arg Asp Lys His Leu Leu Ile Ser His Val Gly
                325                 330                 335

Asp Asn Val Tyr Glu Val Gln Leu Leu Ser Glu Asn Glu Ala Leu Glu
            340                 345                 350

Leu Phe Ser Arg His Ala Phe Arg Glu Arg Ser Pro Lys Glu Asp Phe
        355                 360                 365

Met Glu Leu Ser Arg Gln Val Val Lys His Ala Gly Gly Leu Pro Leu
370                 375                 380

Ala Leu Lys Val Leu Gly Ser Ser Phe Tyr Gly Arg Asp Lys Lys His
385                 390                 395                 400

Trp Arg His Ile Ile Asp Arg Leu Lys Arg Ile Pro His Lys Asp Ile
                405                 410                 415
```

```
Leu Gly Lys Leu Arg Leu Ser Phe Asp Gly Leu Asp Lys Asp Glu Lys
            420                 425                 430

Glu Leu Phe Leu Asp Ile Val Phe Leu Glu Ile Ala Cys Leu Ser Gly
            435                 440                 445

Tyr Asp Phe Asn Ile Tyr Val Glu Gln Val Gln Arg Tyr Val Ser Arg
450                 455                 460

Gly Leu Leu Ile Tyr Tyr Leu Ile Glu Lys Ser Leu Leu Ser Ile Asp
465                 470                 475                 480

Trp Ser Asn Ser Ile Val Ile His Asn Met Ile Arg Glu Met Gly Glu
                485                 490                 495

Asn Val Ile Arg Glu Glu Tyr Ala Asn Ser Arg Ile Trp Leu Pro Glu
                500                 505                 510

Glu Ile Cys Asp Leu Phe Lys Gly Lys Leu Ile Thr Glu Lys Val Glu
            515                 520                 525

Ser Leu Cys Ile Pro Lys Glu Tyr Tyr Phe Glu Asp Asp Leu Val Asn
        530                 535                 540

Tyr Ser Asn Ile Phe Lys Arg Met Gln Ser Leu Lys Thr Leu Ile Val
545                 550                 555                 560

Gly Asp Gly Thr Phe Ser Thr Asn Cys Thr Ile Thr Tyr Leu Pro Ser
                565                 570                 575

Ser Leu Arg Phe Ile Asp Trp Lys Gly Tyr Pro Ser Ile Ser Leu Pro
            580                 585                 590

Glu Ser Phe Glu Pro Ser Gln Leu Val Val Leu Cys Leu Tyr Lys Ser
        595                 600                 605

Arg Leu Val Glu Leu Trp Pro Ile Ser Lys Lys Leu Ser Asn Leu Lys
            610                 615                 620

His Leu Asp Leu Met Asp Ser Cys Glu Leu Arg Lys Thr Pro Asn Phe
625                 630                 635                 640

Gly Asp Met Pro Asn Leu Glu Thr Leu Ile Leu His Gly Cys Val Asn
                645                 650                 655

Leu Glu Glu Val His Pro Ser Leu Gly Gln Cys Arg Val Leu Thr Tyr
            660                 665                 670

Leu Ser Leu Glu Gly Cys Arg Lys Leu Lys Leu Pro Lys Phe Val
        675                 680                 685

Cys Val Glu Ser Leu Glu Thr Leu Asn Leu Leu Glu Cys Thr Ser Leu
            690                 695                 700

Gln Glu Phe Pro Glu Ile Cys Gly Asp Met His Arg Leu Ser Thr Leu
705                 710                 715                 720

Asp Val Gly Ser Pro Trp Ile Arg Ser Leu Pro Pro Ser Leu Ser Gly
                725                 730                 735

Leu Arg Tyr Leu Gln Leu Thr Gly Cys Ala Val Leu Glu Ser Ile Pro
            740                 745                 750

Asp Ala Ile Gln Asn Leu Arg Tyr Leu Ser Ile Leu Asp Cys Asn Lys
        755                 760                 765

Leu Ala Thr Leu Pro Asn Ser Leu Phe Glu Ser Gln Gln Leu Glu Tyr
            770                 775                 780

Leu Leu Ile His Arg Cys Ser Gly Leu Val Lys Leu Pro Leu Ser Leu
785                 790                 795                 800

Gly Val Gln Lys Ile Leu Arg Trp Leu Ser Ile Asp Gly Cys Glu Asn
                805                 810                 815

Leu Lys Lys Leu Pro Ser Ser Ile Gln Met Lys Ser Leu Gln Ser Leu
            820                 825                 830
```

```
Trp Ile Ser Asp Ser Pro Lys Leu Asp Thr Phe Pro Glu Ile Asn Gly
            835                 840                 845
Asp Met His Tyr Leu Glu Ile Leu Ser Leu Lys Ser Thr Gly Ile Arg
850                 855                 860
Glu Val Pro Ser Ser Ile Gly Asn Leu Ser Gly Leu Thr Asp Leu Ser
865                 870                 875                 880
Leu Thr Gly Cys Glu Asp Leu Leu Ser Leu Pro Asp Ser Leu Cys Asn
            885                 890                 895
Leu Met Lys Leu Arg Ser Leu Tyr Leu Asp Gly Cys Lys Lys Leu Glu
            900                 905                 910
Lys Leu Pro Glu Asn Ile Gly Asp Leu Gln Asp Leu His Lys Leu Asp
            915                 920                 925
Ala Ser Asp Thr Ala Ile Ser Gln Pro Pro Ser Ser Ile Thr Lys Leu
            930                 935                 940
Gly Lys Leu Trp Lys Leu Arg Phe Ser His Glu Lys Gln Leu Gln Tyr
945                 950                 955                 960
Ser Ser Ser Phe Val Leu Asn Gln Val Ser Gly Leu Ser Ser Leu Thr
            965                 970                 975
Ser Leu Asp Leu Asn Asn His Asn Ile Leu Ser Gly Leu Pro Glu Asp
            980                 985                 990
Leu Gly Ser Leu Gln Ser Leu Glu  Lys Leu Ser Leu Ser  Gly Ser Asn
            995                 1000                1005
Ile Ser  Cys Leu Pro Lys Ser  Phe Lys Gly Leu Leu  His Leu Gln
    1010                1015                1020
His Leu  Asn Val Gln Phe Cys  Gln Asn Leu Asn Lys  Leu Pro Gly
    1025                1030                1035
Glu Leu  Pro Pro Asn Leu Lys  Glu Leu Cys Val Asp  Tyr His Leu
    1040                1045                1050
Ala Leu  Met Ser Ile Arg Asp  Leu Val Ile His Tyr  Pro Lys Leu
    1055                1060                1065
Cys Arg  Leu Gly Ile Ser Asp  Cys Gly Ala Val Ser  Ser Glu Gln
    1070                1075                1080
Val Asn  Val Phe Leu Gln Tyr  Phe Ile Arg Thr Cys  Ile Gln Phe
    1085                1090                1095
Asp Phe  Leu Gln Arg Asp Tyr  Phe Leu Ile Phe Pro  Asp Gln
    1100                1105                1110
Val Arg  Ile Ser Glu Leu Phe  Asp Tyr Asp Arg Phe  Thr Asn Gln
    1115                1120                1125
Lys Glu  Met Ser Ile Asp Leu  Asn Pro Ser Trp Tyr  Thr Asp Lys
    1130                1135                1140
Phe Met  Gly Phe Trp Ile Ser  Tyr Gly Leu Thr Thr  Leu Asn Tyr
    1145                1150                1155
Thr Arg  Leu Glu Ala Thr Leu  Val Cys Lys Ser Asp  Pro Glu Arg
    1160                1165                1170
Lys Tyr  Ser Leu Lys Tyr Asn  Tyr Phe Gly Gln Leu  Cys Ile Glu
    1175                1180                1185
Ser Pro  Ser Ile Cys Cys Phe  Tyr Ile Pro Phe Glu  Thr Leu Trp
    1190                1195                1200
Asn Ala  Ser Gly Asn Lys Glu  Gly Lys Asn Pro Asn  Asp Tyr Tyr
    1205                1210                1215
Met Leu  Glu Val Ser Asn Arg  Tyr Ser Leu Glu Lys  Glu Arg Cys
    1220                1225                1230
Trp Gly  Ile Arg Leu Glu Tyr  Glu Lys Glu Glu Ala  Met Ser Asp
```

Thr Gly Arg Pro Lys Lys Lys Arg Lys Gln
1250              1255

<210> SEQ ID NO 5
<211> LENGTH: 3774
<212> TYPE: DNA
<213> ORGANISM: Solanum stoloniferum

<400> SEQUENCE: 5

| | | | | | |
|---|---|---|---|---|---|
| atgtctcatg | cttcttcttc | caaagtttgc | aagtacgata | tcttttttgag | ttttagaggt | 60 |
| gaagatacac | gtagaaactt | cgtgagtcat | ctttataatg | ctttagaaca | gagaggactc | 120 |
| catgctttca | aagacgatga | gcggttggaa | gcaggaaaat | caatttctgc | tgaactttta | 180 |
| aaagccatag | aagaggccag | attcgctgtc | gtaatatttt | caaaaagcta | tgcatcgtca | 240 |
| agatggtgtt | tagaggagct | tgcacacatc | ataaagtgta | aaaaggaatt | ggagcagatt | 300 |
| gtgattccag | tcttctatga | tgtgagtcca | tcagatgtac | gccatcaaaa | tccccctttc | 360 |
| gctgtttcat | tttcccaaca | tgaggaaaaa | tgcaagatg | atatggagaa | ggttcaaaga | 420 |
| tggagggggcg | catttgcgga | ggcagggaaa | atatcaggct | atcatttact | aaatttcaag | 480 |
| gatgaggcca | agtgcgtcaa | gaaactagtt | gatgacatat | tcctaagtc | acttcaaatt | 540 |
| atttcacctt | tcccggaaag | cttagtgggt | atgaaatctc | aggttgagaa | gtaacctca | 600 |
| ttattagata | tggaatcaaa | cgatgttcgc | tctattggta | tttggggtat | gggcggcatc | 660 |
| ggcaaaacag | aaattgcaaa | tgttctacat | caaagatacc | gccatcaatt | tgacgctgat | 720 |
| tgttttcttg | gtgatgttgg | aaaacttcat | cagaaaaatg | gactaacgtg | gctacaacaa | 780 |
| gtcgtcattt | gcaagctctt | gggtgaaaaa | ttgactctaa | ctagtgagca | tgaagggatg | 840 |
| aatattttaa | agaatatgct | tcgctggaag | aaagttctgt | tcaccatcga | tgacgtaaac | 900 |
| catcaagaac | agttggaatt | tttggttgga | gagccagagt | ggtttggtag | ggtagcaga | 960 |
| attattttaa | cagcaagaga | caagcaccta | ttaatcagtc | acgttgggga | taatgtgtat | 1020 |
| gaagtccaac | tattatctga | aatgaagca | cttgaattgt | tcagtagaca | tgcttttaga | 1080 |
| gaaagatcac | caaaagaaga | ttttatggaa | cttcaagac | aagtggtgaa | gcatgctggt | 1140 |
| ggactccctt | tagctcttaa | agttttgggt | tcttcatttt | acggacgaga | caaaaagcac | 1200 |
| tggagacaca | taattgatcg | gctgaagaga | atccctcaca | aggatattct | aggaaagctt | 1260 |
| aggcttagtt | ttgatggtct | ggacaaagat | gagaaggaat | tatttctgga | tattgtatt | 1320 |
| ctagagattg | catgcttgag | tggatatgat | tttaatattt | atgtgaaaca | agtacagaga | 1380 |
| tatgtgagtc | gtggtttact | aatttattac | cttattgaaa | aatctctgtt | atccatcgac | 1440 |
| tggagtaata | gtattgtgat | tcataatatg | ataagagaaa | tggagaaaaa | tgtcatacgg | 1500 |
| gaagagtacg | ctaacagcag | aatatggctt | cccgaggaga | tttgtgatct | ttttaaggg | 1560 |
| aagttgataa | cagaaaaggt | ggaaagccta | tgtattccaa | agagtacta | ttttgaagat | 1620 |
| gatcttgtca | attatagcaa | tatttttcaag | aggatgcaaa | gcttaaaaac | actcatagtt | 1680 |
| ggtgatggaa | cttttagcac | aaactgcact | atcacttatc | ttccttccag | cctgcggttc | 1740 |
| attgattgga | aagggtatcc | ttcaatttca | ttgccagaga | gctttgaacc | atcacagctt | 1800 |
| gtggtgctt | gtttatataa | aagtaggctt | gttgaacttt | ggccaatatc | aaagaaattg | 1860 |
| agcaacttga | agcatttgga | tctcatggac | agctgtgagt | taagaaaaac | ccctaattt | 1920 |
| ggtgatatgc | caaacttgga | gacactaatt | ttacacgggt | gtgtgaattt | ggaagaggtc | 1980 |

```
catccctctc ttggacagtg cagagtgctt acttatttga gtttggaagg ttgtcgcaaa    2040
cttaagaagc ttccaaaatt tgtctgcgtg aatctcttg agactctcaa tctccttgaa    2100
tgcacaagct tacaagaatt ccagaaatc tgtggagata tgcatcgctt atcgacgctc    2160
gatgtaggat cccctggat aagaagctta ccccatctc tcagcggcct tagatattg     2220
caattgactg agtgtgcagt tcttgaaagt attccggacg ccattcaaaa tcttagatat   2280
ctcagtattt tagattgcaa taaacttgca acactgccaa acagcctctt tgaatcacag   2340
caattggaat atctttaat acaccgatgt tctggattgg taaagctccc cttatctctt    2400
ggagttcaaa agattctccg ttggttaagt atagatggat gtgagaactt aaagaagctt   2460
ccaagctcga ttcagatgaa atcccttcaa agtctctgga tatctgattc cccaaaatta   2520
gacacatttc cagaaatcaa tggagatatg cattacttgg aaatactgtc tctgaagtct   2580
actgggataa gagaagtgcc ttcatccatt gggaatctga gcggcctcac tgatctaagt   2640
cttacaggtt gtgaagatct tctaagtcta ccagacagcc tctgcaattt gatgaaactt   2700
cgaagtcttt acctcgacgg gtgcaaaaag ctagagaagc ttccagaaaa cattggtgat   2760
ttgcaagatt tacataaact tgatgcgagc gatactgcaa tctcccaacc accttcctcc   2820
atcactaagc ttggcaaact gtggaagtta cgattctcac atgaaaaaca acttcaatat   2880
tcctcaagtt ttgtcttgaa tcaagtatca ggtttatcgt ccttgacatc acttgatctt   2940
aataatcaca acatattgag tggacttcct gaggatttag gatctttgca gtctttggaa   3000
aaactgagtc taagtggaag caatatttct tgtttaccaa aaagcttcaa aggactctta   3060
caccttcagc atctgaatgt acaattctgt cagaatctta ataaattgcc cggagagcta   3120
cccccaaatt taaaggagct atgtgtagat tatcatttag ccttaatgag catcagagat   3180
ctcgtaattc attatcctaa gctgtgtagg cttgggatat ccgactgtgg agccgtctca   3240
agtgaacaag ttaatgtgtt cctacaatat tttatcagga catgcatcca gtttgacttt   3300
ctccaaagag attattttct cattttttt cctgatcaag tcagaatttc agagttgttt    3360
gattatgatc ggtttacaaa tcaaaagag atgtcaattg atctgaaccc atcttggtat    3420
accgataaat tcatgggttt ttggataagt tatggtctta ctacactgaa ctacacaaga   3480
ttagaagcta cattggtctg caaatctgac cctgaaagaa atattccttt gaagtataac   3540
tactttggac aattgtgtat cgagtctcct tccatttgtt gcttctacat accatttgaa   3600
acactgtgga atgcttctgg caataaagaa gggaagaatc caaatgatta ttacatgttg   3660
gaggtatcta ataggtacag tctggagaaa aacgatgct ggggaattcg cctggagtat    3720
gaaaaggagg aggcaatgag tgatactggt cgtccaaaaa agaaaaggaa gcaa         3774
```

<210> SEQ ID NO 6
<211> LENGTH: 8206
<212> TYPE: DNA
<213> ORGANISM: Solanum stoloniferum

<400> SEQUENCE: 6

```
agtttatgaa tatataaagt gatgatttgg agttgaataa ttaaaattta gtaacaagca      60
aataagacta ttaaacataa aagcagtagt tcagtttttc ctaacctaac tttaaatatt     120
aggaaaatag aaaattatgt gattatagaa agattttaat tatgacaagt ggaagacaga     180
ctcttattgt aataaaatat aattatttaa ggtggtgttt tctttttcta ctaatgcaag     240
atagcatcct ccttttaaag gaaaacataa acaataaat taaatatgtg aggacaattt      300
tacttgtgtt ctaaataatt gactatttta acaatttatt ttaagaaata cttttattga    360
```

-continued

```
ttttgaagtc ctaaatttta gttacataat tcaaatagtg caaggttttt gataatcaac      420
tttaaatgaa ttttcaattt ctaaatatta ggaaaattat tgaatgatta ttttatctag      480
tgtaaaatct atctttaagg ggtaaaaaag tttaattcat tatctttatt cgtgcatatt      540
cttgatattt ttaaatttct tggcatctaa aacactctca tcattttttt gagataaatt      600
tgatctaacg gggaaattct tcaaataaga taaaggtaaa acgctctctt tgaaagatat      660
atacactaca tcaaaaatga tatttagcaa caattaatta atgataatag tttaattgcc      720
gctaaatata tatatatata tatagtttta gtggtaatta acactctttg taaatgtctc      780
tgaagtcaat agctacatta gatcaataaa taattaacta atgtcagtaa agactttaac      840
agtctttatt aatgtgtata ttccgttaaa agtagttgtt tttgttatag tgatacttgt      900
actgcttctg cctctcaagg actttaacag tcgtgcatat atttattgcg gctaaatgtt      960 gtttttttg ttgtattgat acttgcactg cttctgcctc tcaaggactc tatgcattga     1020 acttcccttta tatctttagg ggagtataaa caaacatctg agttgctctc tccttcttcc     1080
tctttgcaga agcattatag attcttttag tcaccaactt actgagagaa gagatgtctt     1140
gggaaaattt gcatcgactt ttcaattttg taatcatccc taaaatttcg atacacaaac     1200
tccagctctt cacactggaa cgcgaattcc acaaaatttt catttgcttg cagagattca     1260
cagatgaacc taacatgcta gatgtcactc agaaagtcca aactctgttt gaagatgttg     1320
catttatcct ttctccactg tacctaactg acaactttga tgtctgtgcc tctgaggtgc     1380
aaaacaagat tttgttaatc aagaaggaaa taagagccaa atactccttt cctaaaatat     1440
cattacaact ttcagccgag tttgttagtg atatcatcca ttctgtgcta gagaatattg     1500
gtggtctagt gaagattcat gatccatatt caccttctta tgttcccgaa acagtagagg     1560
aacatataga agatgtttca aaggaattga atttgctgct aattttcgtc tactttgttt     1620
cagagaggtt cctagagcat cagagccaac atcatattat tttcttcact catgttttag     1680
ctgtgtctgt ccacacatca atgcttctct ggttgtattt accagacttg gatccagagc     1740
aaatgaatgt tatgctttct gatttcttac gaatgacgat taagccgatt caaccatgca     1800
tccgcaagat ctatgttgat gtcttgctat ctctaaagtc gacaatacaa tcaggatggt     1860
atcccaacat ccgaaatgag gatgcagttg acagcgaagg ggtattttg gagaccatcc     1920 tacacaattt ggtggaggta ccaactaata gtaactctag tcagagagtt gctttgaagg     1980
atcacttgga aacccttcaa aacatgctca acctttttgag tgccaatatc ttccgtgtgc     2040
caataaaaga tcttgaattt cttctttgag atatagagat tgtggttatt gatgttggac     2100
ttctggtata ctcattatat gaagatgagg aggagaagga agacatggca ccaggaggag     2160
tgcacattac acaagttctt gatttgtcaa gcaacattca acgtctaagc atagacatct     2220
acctcaccat tcggaaggca ttccaatcta atttgcctag gattcatgga ctaggctatg     2280
ttgattgcca tttaaacaac ctgaagaagt tccaaatcct ccattcagat tcactagctt     2340
ctgtcatgga caaacttcaa tcaattcaga aagaatttga gagcttgcaa ccttttctac     2400
aggctgttgc agaagcgcga cacaatgacc ttgatgcaat tcaacattgt gctacacaat     2460
tgattggcaa agcacatgag gtagaataca tagttgatgc ttgtataagg gaagaagctc     2520
ctcaactccc atcttgttgg tgagactctg attccccaca ctgtgattct acctcatttt     2580
cccttcccct accatttttt ttaaaaaaat ataaaaattt aaactaacaa tacagtacaa     2640
tataattgat atcaaccatc ccaaacaagg tgcaacgggt tgtgtggtag ctgtatgaga     2700
```

```
aacaaattat ccatatgtta attttcgtat aatttatatg atgtttgata ggtagataaa    2760
ttataactta atataattta taagattaac ttttgactca taagttaaaa attataactt    2820 gtgattttt aacattttat cttaaactca agtgcttata agtactttaa tagtttacct    2880
aaaattaaca cttcaacagt cgttagataa agtgtataag aataatgcta ataaaaatgt    2940
attagtaatg cttgcatcaa ttatacatag attattttta tgcattgttc ggtttgatgc    3000
attaaaaatt tacaaagata tgtttcacta ttatggtgga aaagatttaa aagaaaaaaa    3060
aaagattttg acaggcaatt gagtgattaa acatgctaat gcatgcattt aaaacgattg    3120
cattgcgaat atttagaaat ccatggtatt agcaatacag agttacacat agattagaaa    3180
aaattagcaa acaaagtact agtaataggc aagggtaatg catgcattat ttttcgaaa     3240 taacgacaac taaaggcgag aatggataat aagtagcaaa tagagctcat agcatagagt    3300
ctattctggt aggcaatctt gtgaagaaat tgagtggagc agatggtagg ttgtgatgga    3360
accatggatg tcttaacaca taaaatccag tgactagagt tgcaactcga aacccatga     3420 aatagagaac aatgacagca atcaagcagg aaataacaaa cagtttggtc gctgtagggt    3480
ctctccatga caccaaagag ttcagcctct ccagttgatt agctatgtca ccagccacat    3540
tctgaatact tccagcaata cttttcaaac gggtcatacc ttatccgaac aatatcaatt    3600
cgacgtgaag tagggaaagt atcaaactcc tcgtccagtt catcaggatg agcatcatca    3660
gcacaagaaa gacgaatgtc tatgaaggga ggatgcctag gcctatatct ataattccaa    3720
actacgatta aggagagcga gaggaaaatg gtaggcagaa tacactccgg atatagaact    3780
agtatcaaat acaagacatg gatcacaaga gtcgtaatgg gattttttcca actgcaaatt    3840 tgatcaaacc atttcctaat agaatttgag agtttgcaac cttttctaca ggctgttgca    3900
gaagcgcgac acaatgacct tgacgaaatt caacattgtg caacacaatt gattggcaaa    3960
gcacatgagg tagaatacat agttgatgct tgtataaggg aagaagctcc tgtctgctgc    4020
ctcgagcatt ggatcttgga tatcatggag gatattactc ttatcagaga agaggtagca    4080
gagattcgtg aaaagaaaat ggatttggta gcattgaaca ctgtccctgt taatacatca    4140
aatttggcaa ggtctccaat gatgaatgaa gaaattattg gttttgagga tgaaatagaa    4200
aagttaagag accaactaat aaaaggcacg aaagggcgcg atgttatatc agttgttggt    4260
atgccaggtc taggcaagac aacttttggcc tacagactct actatgacag gttagtctct    4320
tctcacttca acattcgtgc acagtgttgt gtgtctcaag tatattcacg taaggacttg    4380
ttaatagcaa ttttacgtga tgctatcagt gagaactttg agtgtagaga aaacaagct    4440 gatgaattag ctgatctgct tcgcaaaact ttatttcccg aaagatatct catccttgtt    4500
gatgatgtgt gggaaactag tgtgtgggat gatctaatag gttctttcca tgatgccaat    4560
aacggaagta gaattattct aacaacgcga aatcatgaag ttgccatgta cactagattt    4620
caaagtgatc cgcttccgct tcgtatgttt aacaatggtg aaagttggga gttactccga    4680
aaaaaagtgt ttggtgaaga aagtttctct ccactcctaa cagaaattgg gcaacaaata    4740 gcaaaaagt gtggtcaact gcctctttca gttgtttgg tggctggtat tctggctgag    4800
atggagaaga aagtagaatg ttggaatcaa ctggccaaca atttaggtcc ccacattcat    4860
gaagactcaa gggccgttat agaacaaagt tatcagattt tacccctatcg tttgagacct    4920 tgctttcttt actttggagc acttttagag gatagtgtga ttagtgttcc aaagttaaca    4980
cagttgtgga tctcagaagg attcgtaaaa agttgtgaag gcaagaactt ggaggatata    5040
gcagaaggct attttggaaaa tcttattgga agaaatctag tgatgggaac gaagaggagt    5100
```

```
tctcgtggta agatcaaagc atgtcgcatt catgacctat tgcatgattt ctgcaaggag      5160
agagcaaagg acgatatgcg tctcctatgg caaaaatggt aatataccaa tcattgctac      5220
tcttttcact tatattgaca tttaatcata taattttact aatttctgta tatatttgta      5280
gggatcaaaa tgccaatccg tcttctcgcc tttctggtca caagcaacta gctcaccgca      5340
tgtgcattta tggtgaaggg tatcgtgctg agagttggag ctcgtgcttg tcacatgttg      5400
tttctataat tttgcataac aatcgtcttt cagttggcct cgactctcac attttccacg      5460
gcgtaaagtt tctaaaagtg ttagatatgg agttcactag aattaattct ttctcatttg      5520
atctagtcta cctcaggtat tttgctgcag aaacttcccg cttttcaaac aaagccggtt      5580
gtcgcgaact tgaaactctg aaattaaaat ctctcagtga agtgtcacta cccattacat      5640
tctgggagat ggataaattg agacatgtgg atatttccaa ttgcagcttc accagtgaaa      5700
ttgcaaggga attgattgag aactccaaag accttcatga tctgcaaact ctatccactc      5760
cgtgcttttc ttgtgctcag gaagcggaat tgattttgag aaaaacacct aatcttctgg      5820
aactgagatg caaagtcaag ggtgttgata ctttgagtg ctatgtattg aactttccag       5880
cacgcattga aacactcaag attcatctta gctacacacg tgacactaaa acaatcccct      5940
tctgcatctc cgcgccaact ctcacaaact tgacactgaa gaacttttac ctacattgtc      6000
agcatttatc acaaattggt tcacttcaga accttcaagt gctcagtctg aaaggtattt      6060
cctttgaaac ttgtaaatgg gaagtgcgtg atgacgagtt ccctcagctc aaagtcttga      6120
aattacattc tggaaaagct cactttgaag aatggtctgt cgcggatgat gcctttccta      6180
accttgaaca cttggttttg agggattgca aatttcttaa ggagatccct tcttggtttg      6240
ctgaaatctc ttctctgaag tccattgagg taaggaattg caatgaaaat gttgacaagt      6300
cagccagtga tataagggaa acacaagttg aagattacca gaactccaag ttcgaggtct      6360
ttatcaccag agagaataac aagtcagatt caggtacgca actcataaaa ttcaactatg      6420
aacagtccta aactctgtga attcatttct tctgttactc taacttcctt tttaaaggta      6480
aaagttcttg aattagcacc aaggtttgaa atactattgt gcaccttgac taattctcta      6540
ggtacctact acctccaacc gcacatgtac tagataactg atgatcaaaa gaatcaact       6600 agtgacttca aaagagaccc atgaggtctc aagttcaaat ccagtagtgt caaaaacact      6660
atgcgatggt gggcagagtt accaggtacg tatgttggta ggaggtagca ggtacccta       6720 gaattactca aagtgcacac aagctaaacc aaataccatg gttaattatt aaaaaataaa      6780
taaaaaatat gctcttactt tctgtttggg tatgttgttg tagtagtaca acattttga       6840 gcaattaact tattggaacc ttttctttt taacagcata ggaagactag agttgtatca       6900
ggagctgttt agaagatcag tacgtaattt tttttgaagc ttaattaata aatcatgtac      6960
ttttggtctt gaatgtattg agtaacattg aatccatgtt gaactatagt tctatgagct      7020
atttataata ttttctagat ttcttttct tcttacgtat gtccatttac actcatcttt       7080
catgctatgg aggaagaact ttgacgtaac cggtaaagtt gttgtcatgt aactagaagg      7140
tcatgtacga gttcgacatg tggaaaatac ctcttgcaga aagcgagagc ttagtcatta      7200
ggctacccta ttttgtact cgttttgtat tccttccaat gcttgccact caaaccctat       7260
atcctatctc agggtcacgt caagtagatt ccactttaga gataagtttt ttatcttaat      7320
ggatcaaaat agattaagac tatcagaagt tacttagtct cattcgagaa tttaatctcc      7380
ttagcgtgac aaagagccca ttcaatagca tttgtgccag cttgaaagga cgtactacca      7440
```

-continued

```
gtctaccatg atatctaatg ctctctcaat gtcaataggg actcaacaac ttttgataaa    7500
atataataaa agcaacgtcg ataggattca acaactttt ggtgaaataa aatatataaa     7560
agtaaagtaa ctatttccta aaattatcca atttgtagac cacaagttac ctttgtctat    7620 gaaccttta tgttaactt aatgagaaat tcatttgttt atttccctct tgttattaaa     7680
gctaaagaat tctggcaata atttatacag tgtttggtat ggtagaaaaa aaagttatt    7740 aatatataaa attaatacaa aattaggttg acaatccaca taactaataa aatattatga    7800
gttaacctat atattatttt atgcaggata gaaggtggaa taactaatac atgaaaaatt    7860
aattccgtat aaataataca taggttcact cattactaat ttatacatta ctaatatgtg    7920
gttaactctt accaactacc aaacaataat cacgtcctgt aaatttggta agttttaatt    7980
gactattgag atcaggggcg gctctacagc tttgaaaaaa aaagcaattg ccttaagccc    8040
caaaatttga ggggcctcat ttttaaaaaa aataataggt tataagtatt ttttttttaa    8100
atatcgagta ttacttgtag aaaataaaaa cttccataa aagagcaaag aagtaataga     8160
agttcgacaa attatgaata ccatgtctca agaaagatta aataat                   8206
```

<210> SEQ ID NO 7
<211> LENGTH: 939
<212> TYPE: PRT
<213> ORGANISM: Solanum stoloniferum

<400> SEQUENCE: 7

```
Met Ala Pro Gly Gly Val His Ile Thr Gln Val Leu Asp Leu Ser Ser
1               5                   10                  15

Asn Ile Gln Arg Leu Ser Ile Asp Ile Tyr Leu Thr Ile Arg Lys Ala
            20                  25                  30

Phe Gln Ser Asn Leu Pro Arg Ile His Gly Leu Gly Tyr Val Asp Cys
        35                  40                  45

His Leu Asn Asn Leu Lys Lys Phe Gln Ile Leu His Ser Asp Ser Leu
    50                  55                  60

Ala Ser Val Met Asp Lys Leu Gln Ser Ile Gln Lys Glu Phe Glu Ser
65                  70                  75                  80

Leu Gln Pro Phe Leu Gln Ala Val Ala Glu Ala Arg His Asn Asp Leu
                85                  90                  95

Asp Ala Ile Gln His Cys Ala Thr Gln Leu Ile Gly Lys Ala His Glu
            100                 105                 110

Val Glu Tyr Ile Val Asp Ala Cys Ile Arg Glu Glu Ala Pro Gln Leu
        115                 120                 125

Pro Ser Cys Trp Ala Val Ala Glu Ala Arg His Asn Asp Leu Asp Glu
    130                 135                 140

Ile Gln His Cys Ala Thr Gln Leu Ile Gly Lys Ala His Glu Val Glu
145                 150                 155                 160

Tyr Ile Val Asp Ala Cys Ile Arg Glu Glu Ala Pro Val Cys Cys Leu
                165                 170                 175

Glu His Trp Ile Leu Asp Ile Met Glu Asp Ile Thr Leu Ile Arg Glu
            180                 185                 190

Glu Val Ala Glu Ile Arg Glu Lys Lys Met Asp Leu Val Ala Leu Asn
        195                 200                 205

Thr Val Pro Val Asn Thr Ser Asn Leu Ala Arg Ser Pro Met Met Asn
    210                 215                 220

Glu Glu Ile Ile Gly Phe Glu Asp Glu Ile Glu Lys Leu Arg Asp Gln
225                 230                 235                 240
```

-continued

```
Leu Ile Lys Gly Thr Lys Gly Arg Asp Val Ile Ser Val Val Gly Met
            245                 250                 255
Pro Gly Leu Gly Lys Thr Thr Leu Ala Tyr Arg Leu Tyr Tyr Asp Arg
        260                 265                 270
Leu Val Ser Ser His Phe Asn Ile Arg Ala Gln Cys Cys Val Ser Gln
    275                 280                 285
Val Tyr Ser Arg Lys Asp Leu Leu Ile Ala Ile Leu Arg Asp Ala Ile
290                 295                 300
Ser Glu Asn Phe Glu Cys Arg Glu Lys Gln Ala Asp Glu Leu Ala Asp
305                 310                 315                 320
Leu Leu Arg Lys Thr Leu Phe Pro Arg Tyr Leu Ile Leu Val Asp
                325                 330                 335
Asp Val Trp Glu Thr Ser Val Trp Asp Asp Leu Ile Gly Ser Phe His
            340                 345                 350
Asp Ala Asn Asn Gly Ser Arg Ile Ile Leu Thr Thr Arg Asn His Glu
        355                 360                 365
Val Ala Met Tyr Thr Arg Phe Gln Ser Asp Pro Leu Pro Leu Arg Met
    370                 375                 380
Phe Asn Gly Glu Ser Trp Glu Leu Leu Arg Lys Val Phe Gly
385                 390                 395                 400
Glu Glu Ser Phe Ser Pro Leu Leu Thr Glu Ile Gly Gln Gln Ile Ala
                405                 410                 415
Lys Lys Cys Gly Gln Leu Pro Leu Ser Val Val Leu Val Ala Gly Ile
            420                 425                 430
Leu Ala Glu Met Glu Lys Lys Val Glu Cys Trp Asn Gln Leu Ala Asn
        435                 440                 445
Asn Leu Gly Pro His Ile His Glu Asp Ser Arg Ala Val Ile Glu Gln
    450                 455                 460
Ser Tyr Gln Ile Leu Pro Tyr Arg Leu Arg Pro Cys Phe Leu Tyr Phe
465                 470                 475                 480
Gly Ala Leu Leu Glu Asp Ser Val Ile Ser Val Pro Lys Leu Thr Gln
                485                 490                 495
Leu Trp Ile Ser Glu Gly Phe Val Lys Ser Cys Glu Gly Lys Asn Leu
            500                 505                 510
Glu Asp Ile Ala Glu Gly Tyr Leu Glu Asn Leu Ile Gly Arg Asn Leu
        515                 520                 525
Val Met Gly Thr Lys Arg Ser Ser Arg Gly Lys Ile Lys Ala Cys Arg
    530                 535                 540
Ile His Asp Leu Leu His Asp Phe Cys Lys Glu Arg Ala Lys Asp Asp
545                 550                 555                 560
Met Arg Leu Leu Trp Gln Lys Trp Asp Gln Asn Ala Asn Pro Ser Ser
                565                 570                 575
Arg Leu Ser Gly His Lys Gln Leu Ala His Arg Met Cys Ile Tyr Gly
            580                 585                 590
Glu Gly Tyr Arg Ala Gly Asp Trp Ser Ser Cys Leu Ser His Val Val
        595                 600                 605
Ser Ile Ile Leu His Asn Asn Arg Leu Ser Val Gly Leu Asp Ser His
    610                 615                 620
Ile Phe His Gly Val Lys Phe Leu Lys Val Leu Asp Met Glu Phe Thr
625                 630                 635                 640
Arg Ile Asn Ser Phe Ser Phe Asp Leu Val Tyr Leu Arg Tyr Phe Ala
                645                 650                 655
Ala Glu Thr Ser Arg Phe Ser Asn Lys Ala Gly Cys Arg Glu Leu Glu
```

```
                660              665               670
Thr Leu Lys Leu Lys Ser Leu Ser Glu Val Ser Leu Pro Ile Thr Phe
                675              680               685

Trp Glu Met Asp Lys Leu Arg His Val Asp Ile Ser Asn Cys Ser Phe
    690              695              700

Thr Ser Glu Ile Ala Arg Glu Leu Ile Glu Asn Ser Lys Asp Leu His
705             710              715              720

Asp Leu Gln Thr Leu Ser Thr Pro Cys Phe Ser Cys Ala Gln Glu Ala
                725              730              735

Glu Leu Ile Leu Arg Lys Thr Pro Asn Leu Leu Glu Leu Arg Cys Lys
            740              745              750

Val Lys Gly Val Asp Asn Phe Glu Cys Tyr Val Leu Asn Phe Pro Ala
        755              760              765

Arg Ile Glu Thr Leu Lys Ile His Leu Ser Tyr Thr Arg Asp Thr Lys
    770              775              780

Thr Ile Pro Phe Cys Ile Ser Ala Pro Thr Leu Thr Asn Leu Thr Leu
785             790              795              800

Lys Asn Phe Tyr Leu His Cys Gln His Leu Ser Gln Ile Gly Ser Leu
                805              810              815

Gln Asn Leu Gln Val Leu Ser Leu Lys Gly Ile Ser Phe Glu Thr Cys
            820              825              830

Lys Trp Glu Val Arg Asp Asp Glu Phe Pro Gln Leu Lys Val Leu Lys
        835              840              845

Leu His Ser Gly Lys Ala His Phe Glu Glu Trp Ser Val Ala Asp Asp
    850              855              860

Ala Phe Pro Asn Leu Glu His Leu Val Leu Arg Asp Cys Lys Phe Leu
865             870              875              880

Lys Glu Ile Pro Ser Trp Phe Ala Glu Ile Ser Ser Leu Lys Ser Ile
                885              890              895

Glu Val Arg Asn Cys Asn Glu Asn Val Asp Lys Ser Ala Ser Asp Ile
            900              905              910

Arg Glu Thr Gln Val Glu Asp Tyr Gln Asn Ser Lys Phe Glu Val Phe
        915              920              925

Ile Thr Arg Glu Asn Asn Lys Ser Asp Ser Ala
    930              935

<210> SEQ ID NO 8
<211> LENGTH: 2817
<212> TYPE: DNA
<213> ORGANISM: Solanum stoloniferum

<400> SEQUENCE: 8
atggcaccag aggagtgca cattacacaa gttcttgatt tgtcaagcaa cattcaacgt      60
ctaagcatag acatctacct caccattcgg aaggcattcc aatctaattt gcctaggatt    120
catggactag ctatgttga ttgccattta acaacctga agaagttcca atcctccat      180 tcagattcac tagcttctgt catggacaaa cttcaatcaa ttcagaaaga atttgagagc    240
ttgcaacctt ttctacaggc tgttgcagaa gcgcgacaca atgaccttga tgcaattcaa    300
cattgtgcta cacaattgat tggcaaagca catgaggtag aatacatagt tgatgcttgt    360
ataagggaag aagctcctca actcccatct tgttgggctg ttgcagaagc gcgacacaat    420
gaccttgacg aaattcaaca ttgtgcaaca caattgattg gcaaagcaca tgaggtagaa    480
tacatagttg atgcttgtat aagggaagaa gctcctgtct gctgcctcga gcattggatc    540
```

```
ttggatatca tggaggatat tactcttatc agagaagagg tagcagagat tcgtgaaaag      600
aaaatggatt tggtagcatt gaacactgtc cctgttaata catcaaattt ggcaaggtct      660
ccaatgatga atgaagaaat tattggtttt gaggatgaaa tagaaaagtt aagagaccaa      720
ctaataaaag gcacgaaagg gcgcgatgtt atatcagttg ttggtatgcc aggtctaggc      780
aagacaactt tggcctacag actctactat gacaggttag tctcttctca cttcaacatt      840
cgtgcacagt gttgtgtgtc tcaagtatat tcacgtaagg acttgttaat agcaatttta      900
cgtgatgcta tcagtgagaa cttgagtgt agagaaaaac aagctgatga attagctgat       960
ctgcttcgca aaactttatt tcccgaaaga tatctcatcc ttgttgatga tgtgtgggaa      1020
actagtgtgt gggatgatct aataggttct ttccatgatg ccaataacgg aagtagaatt      1080
attctaacaa cgcgaaatca tgaagttgcc atgtacacta gatttcaaag tgatccgctt      1140
ccgcttcgta tgtttaacaa tggtgaaagt tgggagttac tccgaaaaaa agtgtttggt      1200
gaagaaagtt tctctccact cctaacagaa attgggcaac aaatagcaaa aagtgtggt       1260
caactgcctc tttcagttgt tttggtggct ggtattctgg ctgagatgga gaagaaagta      1320
gaatgttgga atcaactggc caacaattta ggtccccaca ttcatgaaga ctcaagggcc      1380
gttatagaac aaagttatca gattttaccc tatcgtttga gccttgctt tctttacttt       1440
ggagcacttt tagaggatag tgtgattagt gttccaaagt taacacagtt gtggatctca      1500
gaaggattcg taaaaagttg tgaaggcaag aacttggagg atatagcaga aggctatttg      1560
gaaaatctta ttggaagaaa tctagtgatg ggaacgaaga ggagttctcg tggtaagatc      1620
aaagcatgtc gcattcatga cctattgcat gatttctgca aggagagagc aaaggacgat      1680
atgcgtctcc tatggcaaaa atgggatcaa aatgccaatc cgtcttctcg cctttctggt      1740
cacaagcaac tagctcaccg catgtgcatt tatggtgaag ggtatcgtgc tggagattgg      1800
agctcgtgct tgtcacatgt tgtttctata attttgcata acaatcgtct ttcagttggc      1860
ctcgactctc acatttttcca cggcgtaaag tttctaaaag tgttagatat ggagttcact      1920
agaattaatt ctttctcatt tgatctagtc tacctcaggt attttgctgc agaaacttcc      1980
cgcttttcaa acaaagccgg ttgtcgcgaa cttgaaactc tgaaattaaa atctctcagt      2040
gaagtgtcac tacccattac attctgggag atggataaat tgagacatgt ggatatttcc      2100
aattgcagct tcaccagtga aattgcaagg gaattgattg agaactccaa agaccttcat      2160
gatctgcaaa ctctatccac tccgtgcttt tcttgtgctc aggaagcgga attgattttg      2220
agaaaaacac ctaatcttct ggaactgaga tgcaaagtca agggtgttga taactttgag      2280
tgctatgtat tgaactttcc agcacgcatt gaaacactca agattcatct tagctacaca      2340
cgtgacacta aaacaatccc cttctgcatc tccgcgccaa ctctcacaaa cttgacactg      2400
aagaactttt acctacattg tcagcattta tcacaaattg gttcacttca gaaccttcaa      2460
gtgctcagtc tgaaaggtat ttccctttgaa acttgtaaat gggaagtgcg tgatgacgag      2520
ttccctcagc tcaaagtctt gaaattacat tctggaaaag ctcactttga agaatggtct      2580
gtcgcggatg atgccttttcc taaccttgaa cacttggttt tgagggattg caaatttctt      2640
aaggagatcc cttcttggtt tgctgaaatc tcttctctga agtccattga ggtaaggaat      2700
tgcaatgaaa atgttgacaa gtcagccagt gatataaggg aaacacaagt tgaagattac      2760
cagaactcca agttcgaggt ctttatcacc agagagaata acaagtcaga ttcagca         2817
```

<210> SEQ ID NO 9
<211> LENGTH: 6321

```
<212> TYPE: DNA
<213> ORGANISM: Artificial sequence
<220> FEATURE:
<223> OTHER INFORMATION: synthetic nucleic acid construct
<220> FEATURE:
<221> NAME/KEY: promoter
<222> LOCATION: (1)..(426)
<223> OTHER INFORMATION: CaMV 35S promoter
<220> FEATURE:
<221> NAME/KEY: 5'UTR
<222> LOCATION: (443)..(504)
<220> FEATURE:
<221> NAME/KEY: misc_feature
<222> LOCATION: (581)..(1059)
<223> OTHER INFORMATION: Splice Variants 1 and 2 - CDS
<220> FEATURE:
<221> NAME/KEY: misc_feature
<222> LOCATION: (1309)..(2395)
<223> OTHER INFORMATION: Splice Variants 1 and 2 - CDS
<220> FEATURE:
<221> NAME/KEY: misc_feature
<222> LOCATION: (2504)..(2791)
<223> OTHER INFORMATION: Splice Variants 1 and 2 - CDS
<220> FEATURE:
<221> NAME/KEY: misc_feature
<222> LOCATION: (3331)..(4794)
<223> OTHER INFORMATION: Splice Variant 1 - CDS
<220> FEATURE:
<221> NAME/KEY: misc_feature
<222> LOCATION: (3331)..(4767)
<223> OTHER INFORMATION: Splice Variant 2 - CDS
<220> FEATURE:
<221> NAME/KEY: misc_feature
<222> LOCATION: (4857)..(5342)
<223> OTHER INFORMATION: Splice Variant 2 -CDS
<220> FEATURE:
<221> NAME/KEY: terminator
<222> LOCATION: (5608)..(6321)
<223> OTHER INFORMATION: OCS terminator

<400> SEQUENCE: 9
gtcaacatgg tggagcacga cactctggtc tactccaaaa atgtcaaaga tacagtctca      60
gaagatcaaa gggctattga gacttttcaa caaaggataa tttcgggaaa cctcctcgga     120
ttccattgcc cagctatctg tcacttcatc gaaaggacag tagaaaagga aggtggctcc     180
tacaaatgcc atcattgcga taaaggaaag gctatcattc aagatctctc tgccgacagt     240
ggtcccaaag atggaccccc acccacgagg agcatcgtgg aaaaagaaga ggttccaacc     300
acgtctacaa agcaagtgga ttgatgtgac atctccactg acgtaaggga tgacgcacaa     360
tcccactatc cttcgcaaga cccttcctct atataaggaa gttcatttca tttggagagg     420
acacgctcga gtataagagc tcatttttac aacaattacc aacaacaaca acaacaaac      480 aacattacaa ttacatttac aattatcgat acaagctgag gcttaatggt gctaagaaga     540
cttcatatca gatacgcgtc tttagcaata ttcttcaaca atgtctcatg cttcttcttc     600
caaagtttgc aagtacgata tcttttttgag ttttagaggt gaagatacac gtagaaactt     660
cgtgagtcat ctttataatg ctttagaaca gagaggactc catgctttca aagacgatga     720
gcggttggaa gcaggaaaat caatttctgc tgaactttta aaagccatag aagaggccag     780
attcgctgtc gtaatatttt caaaaagcta tgcatcgtca agatggtgtt tagaggagct     840
tgcacacatc ataaagtgta aaaggaatt ggagcagatt gtgattccag tcttctatga     900
tgtgagtcca tcagatgtac gccatcaaaa tccccctttc gctgtttcat tttcccaaca     960
tgaggaaaaa tgcaaagatg atatggagaa ggttcaaaga tggaggggcg catttgcgga    1020
ggcagggaaa atatcaggct atcatttact aaatttcaag taagccttct tttttctttt    1080
ttttcgggtt tctcttatc aagaggaaaa aggaccaaac ttttagccaa aaaggaacaa    1140
```

```
agatcctagg aaaacagaaa cgtatatgat tgtttgatga tgtaattaga tttaaaaatg    1200
ttataattca taattgacat tattatgtgt ttgttttaga tattagtcta tgacaagtct    1260
ttgcttttct atttatttac tttgagatta ttttccactg taacgtaggg atgaggccaa    1320
gtgcgtcaag aaactagttg atgacatatt tcctaagtca cttcaaatta tttcacccttt   1380 cccggaaagc ttagtgggta tgaaatctca ggttgagaaa gtaacctcat tattagatat    1440
ggaatcaaac gatgttcgct ctattggtat ttggggtatg ggcggcatcg gcaaaacaga    1500
aattgcaaat gttctacatc aaagataccg ccatcaattt gacgctgatt gttttcttgg    1560
tgatgttgga aaacttcatc agaaaaatgg actaacgtgg ctacaacaag tcgtcatttg    1620
caagctcttg ggtgaaaaat tgactctaac tagtgagcat gaagggatga atattttaaa    1680
gaatatgctt cgctggaaga aagttctgtt caccatcgat gacgtaaacc atcaagaaca    1740
gttggaattt ttggttggag agccagagtg gtttggtagg ggtagcagaa ttattttaac    1800
agcaagagac aagcacctat taatcagtca cgttggggat aatgtgtatg aagtccaact    1860
attatctgag aatgaagcac ttgaattgtt cagtagacat gcttttagag aaagatcacc    1920
aaaagaagat tttatggaac tttcaagaca agtggtgaag catgctggtg gactcccttt    1980
agctcttaaa gttttgggtt cttcatttta cggacgagac aaaaagcact ggagacacat    2040
aattgatcgg ctgaagagaa tccctcacaa ggatattcta ggaaagctta ggcttagttt    2100
tgatggtctg gacaaagatg agaaggaatt atttctggat attgtatttc tagagattgc    2160
atgcttgagt ggatatgatt ttaatattta tgtggaacaa gtacagagat atgtgagtcg    2220
tggtttacta atttattacc ttattgaaaa atctctgtta tccatcgact ggagtaatag    2280
tattgtgatt cataatatga taagagaaat gggagaaaat gtcatacggg aagagtacgc    2340
taacagcaga atatggcttc ccgaggagat ttgtgatctt tttaagggaa agttggtaag    2400
caatatttaa cgtaattaat aatttctaaa gctcttagtt ctgttaattt atttttgtttc   2460 atttttattt gttagtcatt aaatattgtt tcatttttta cagataacag aaaaggtgga    2520
aagcctatgt attccaaaag agtactattt tgaagatgat cttgtcaatt atagcaatat    2580
tttcaagagg atgcaaagct taaaaacact catagttggt gatggaactt ttagcacaaa    2640
ctgcactatc acttatcttc cttccagcct gcggttcatt gattggaaag ggtatccttc    2700
aatttcattg ccagagagct ttgaaccatc acagcttgtg gtgctttgtt tatataaaag    2760
taggcttgtt gaactttggc caatatcaaa ggtaacactc tcttacaaat attagacatc    2820
aactggagtt gttgcaaagt tcttgtacag aataatggaa taataattct gaacaaaatag   2880 ttgtaattat agaatatcat gtatataatg aggttgaaat aaatgttttg ataggccaat    2940
gcatgtaaat taatccatcc atgatttaaa tgctacttta aataaatgtt ctgatataca    3000
caattaacac caaattttta tttattttg gttatcagtc acggcataag gcccataaat     3060
atttttactt ttccaatatt ttaaaaaatt aaatcttata aaaagttacg atattaaaga    3120
ggttttgttt tcattatgaa attaaaagaa aagaaatata tatttggatt ttaagacaat    3180
tatgtatctc aaaagttctt ttccggatta gctaccgcct ttagtgatca taacaacctt    3240
atcttctctt tatctttttt tcctacaaaa tatttctatt aggagtacta cttaagctca    3300
ctgtgttttt tttttttttt tttgaaacag aaattgagca acttgaagca tttggatctc    3360
atggacagct gtgagttaag aaaaacccct aattttggtg atatgccaaa cttgagacca   3420
ctaattttac acgggtgtgt gaatttggaa gaggtccatc cctctcttgg acagtgcaga    3480
```

```
gtgcttactt atttgagttt ggaaggttgt cgcaaactta agaagcttcc aaaatttgtc   3540
tgcgtggaat ctcttgagac tctcaatctc cttgaatgca caagcttaca agaatttcca   3600
gaaatctgtg gagatatgca tcgcttatcg acgctcgatg taggatcccc ctggataaga   3660
agcttacccc catctctcag cggccttaga tatttgcaat tgactgagtg tgcagttctt   3720
gaaagtattc cggacgccat tcaaaatctt agatatctca gtattttaga ttgcaataaa   3780
cttgcaacac tgccaaacag cctctttgaa tcacagcaat tggaatatct tttaatacac   3840
cgatgttctg gattggtaaa gctcccctta tctcttggag ttcaaaagat tctccgttgg   3900
ttaagtatag atggatgtga gaacttaaag aagcttccaa gctcgattca gatgaaatcc   3960
cttcaaagtc tctggatatc tgattcccca aaattagaca catttccaga aatcaatgga   4020
gatatgcatt acttggaaat actgtctctg aagtctactg ggataagaga agtgccttca   4080
tccattggga atctgagcgg cctcactgat ctaagtctta caggttgtga agatcttcta   4140
agtctaccag acagcctctg caatttgatg aaacttcgaa gtctttacct cgacgggtgc   4200
aaaaagctag agaagcttcc agaaaacatt ggtgatttgc aagatttaca taaacttgat   4260
gcgagcgata ctgcaatctc ccaaccacct tcctccatca ctaagcttgg caaactgtgg   4320
aagttacgat tctcacatga aaaacaactt caatattcct caagttttgt cttgaatcaa   4380
gtatcaggtt tatcgtcctt gacatcactt gatcttaata atcacaacat attgagtgga   4440
cttcctgagg atttaggatc tttgcagtct ttggaaaaac tgagtctaag tggaagcaat   4500
atttcttgtt taccaaaaag cttcaaagga ctcttacacc ttcagcatct gaatgtacaa   4560
ttctgtcaga atcttaataa attgcccgga gagctacccc caaatttaaa ggagctatgt   4620
gtagattatc atttagcctt aatgagcatc agagatctcg taattcatta tcctaagctg   4680
tgtaggcttg ggatatccga ctgtggagcc gtctcaagtg aacaagttaa tgtgttccta   4740 caatattta tcaggacatg catccaggtt tttatcttat atatgaaatg ttgaatattc   4800
tcgtcaaatt gattgatttc tagtagtaat aataatttct attctattgc atgcagtttg   4860
actttctcca aagagattat tttctcattt ttttcctga tcaagtcaga atttcagagt   4920
tgtttgatta tgatcggttt acaaatcaaa aagagatgtc aattgatctg aacccatctt   4980
ggtataccga taaattcatg ggttttttgga taagttatgg tcttactaca ctgaactaca   5040
caagattaga agctacattg gtctgcaaat ctgaccctga aagaaaatat tccttgaagt   5100
ataactactt tggacaattg tgtatcgagt ctccttccat ttgttgcttc tacataccat   5160
ttgaaacact gtggaatgct tctggcaata aagaagggaa gaatccaaat gattattaca   5220
tgttggaggt atctaatagg tacagtctgg agaaagaacg atgctgggga attcgcctgg   5280
agtatgaaaa ggaggaggca atgagtgata ctggtcgtcc aaaaaagaaa aggaagcaat   5340
gagtgatgca aaggtccttg ttttacatca caatatttaa atgttcttta tttctttctt   5400
aaattccgta ctcaaccaaa cacgtctcat aaaattgtat ggaaagaata tgttctatat   5460
tgttgataca atttgtatat gaggggtttg tatcgatgat agatagatga attttttttt   5520
ttttataatg ttggttttg agtttgaaac aacttcttta cacttataat aaggtagata   5580
cgttgagtat cctaaacctc agcgcttgtc ctgctttaat gagatatgcg agaagcctat   5640
gatcgcatga tatttgcttt caattctgtt gtgcacgttg taaaaaacct gagcatgtgt   5700
agctcagatc cttaccgccg gtttcggttc attctaatga atatatcacc cgttactatc   5760 gtattttat gaataatatt ctccgttcaa tttactgatt gtaccctact acttatatgt   5820
acaatattaa aatgaaaaca atatattgtg ctgaataggt ttatagcgac atctatgata   5880
```

```
gagcgccaca ataacaaaca attgcgtttt attattacaa atccaatttt aaaaaaagcg    5940
gcagaaccgg tcaaacctaa aagactgatt acataaatct tattcaaatt tcaaaagtgc    6000
cccaggggct agtatctacg acacaccgag cggcgaacta ataacgctca ctgaagggaa    6060
ctccggttcc ccgccggcgc gcatgggtga gattccttga agttgagtat tggccgtccg    6120
ctctaccgaa agttacgggc accattcaac ccggtccagc acggcggccg ggtaaccgac    6180
ttgctgcccc gagaattatg cagcattttt ttggtgtatg tgggcccaa atgaagtgca     6240 ggtcaaacct tgacagtgac gacaaatcgt tgggcgggtc cagggcgaat tttgcgacaa    6300
catgtcgagg ctcagcagga c                                              6321
```

<210> SEQ ID NO 10
<211> LENGTH: 5065
<212> TYPE: DNA
<213> ORGANISM: Solanum stoloniferum

<400> SEQUENCE: 10

```
ggtgctaaga agacttcata tcagatacgc gtctttagca atattcttca acaatgtctc      60
atgcttcttc ttccaaagtt tgcaagtacg atatctttt gagttttaga ggtgaagata      120
cacgtagaaa cttcgtgagt catctttata atgcttaga acagagagga ctccatgctt      180
tcaaagacga tgagcggttg gaagcaggaa atcaatttc tgctgaactt ttaaaagcca      240
tagaagaggc cagattcgct gtcgtaatat tttcaaaaag ctatgcatcg tcaagatggt     300
gtttagagga gcttgcacac atcataaagt gtaaaaagga attggagcag attgtgattc      360
cagtcttcta tgatgtgagt ccatcagatg tacgccatca aaatccccct ttcgctgttt     420
cattttccca acatgaggaa aaatgcaaag atgatatgga aaggttcaa agatggaggg      480 gcgcatttgc ggaggcaggg aaaatatcag gctatcattt actaaatttc aagtaagcct     540
tcttttttct ttttttcgg gtttctcttt atcaagagga aaaaggacca aactttttagc     600 caaaaaggaa caaagatcct aggaaaacag aaacgtatat gattgtttga tgatgtaatt    660
agatttaaaa atgttataat tcataattga cattattatg tgtttgtttt agatattagt    720
ctatgacaag tctttgcttt tctatttatt tactttgaga ttatttttcca ctgtaacgta    780 gggatgaggc caagtgcgtc aagaaactag ttgatgacat atttcctaag tcacttcaaa    840
ttatttcacc tttcccggaa agcttagtgg gtatgaaatc tcaggttgag aaagtaacct    900
cattattaga tatggaatca aacgatgttc gctctattgg tatttggggt atgggcggca    960
tcggcaaaac agaaattgca aatgttctac atcaaagata ccgccatcaa tttgacgctg    1020
attgttttct tggtgatgtt ggaaaacttc atcagaaaaa tggactaacg tggctacaac    1080
aagtcgtcat ttgcaagctc ttgggtgaaa aattgactct aactagtgag catgaaggga    1140
tgaatatttt aaagaatatg cttcgctgga agaaagttct gttcaccatc gatgacgtaa    1200
accatcaaga acagttggaa tttttggttg gagagccaga gtggtttggt aggggtagca    1260
gaattatttt aacagcaaga gacaagcacc tattaatcag tcacgttggg gataatgtgt    1320
atgaagtcca actattatct gagaatgaag cacttgaatt gttcagtaga catgcttta    1380 gagaaagatc accaaaagaa gatttatgg aactttcaag acaagtggtg aagcatgctg    1440
gtggactccc tttagctctt aaagttttgg gttcttcatt ttacggacga gacaaaaagc    1500
actggagaca cataattgat cggctgaaga gaatccctca caaggatatt ctaggaaagc    1560
ttaggcttag ttttgatggt ctggacaaag atgagaagga attatttctg gatattgtat    1620
```

```
ttctagagat tgcatgcttg agtggatatg attttaatat ttatgtggaa caagtacaga    1680
gatatgtgag tcgtggttta ctaatttatt accttattga aaaatctctg ttatccatcg    1740
actggagtaa tagtattgtg attcataata tgataagaga aatgggagaa aatgtcatac    1800
gggaagagta cgctaacagc agaatatggc ttcccgagga gatttgtgat cttttttaaag   1860 ggaagttggt aagcaatatt taacgtaatt aataatttca taagctctta gttctgttaa    1920
tttattttgt ttcattttta tttgttagtc attaaatatt gtttcatttt ttacagataa    1980
cagaaaaggt ggaaagccta tgtattccaa aagagtacta ttttgaagat gatcttgtca    2040
attatagcaa tattttcaag aggatgcaaa gcttaaaaac actcatagtt ggtgatggaa    2100
cttttagcac aaactgcact atcacttatc ttccttccag cctgcggttc attgattgga    2160
aagggtatcc ttcaatttca ttgccagaga gctttgaacc atcacagctt gtggtgcttt    2220
gtttatataa aagtaggctt gttgaacttt ggccaatatc aaaggtaaca ctctcttaca    2280
aatattagac atcaactgga gttgttgcaa agttcttgta cagaataatg gaataataat    2340
tctgaacaaa tagttgtaat tatagaatat catgtatata atgaggttga aataaatgtt    2400
ttgataggcc aatgcatgta aattaatcca tccatgattt aaatgctact ttaaataaat    2460
gttctgatat acacaattaa caccaaattt ttattttatt ttggttatca gtcacggcat    2520
aaggcccata atatttttta cttttccaat attttaaaaa attaaatctt ataaaaagtt    2580
acgatattaa agaggttttg ttttcattat gaaattaaaa gaaagaaat atatatttgg     2640 attttaagac aattatgtat ctcaaaagtt cttttccgga ttagctaccg cctttagtga    2700
tcataacaac cttatcttct ctttatcttt ttttcctaca aaatatttct attaggagta    2760
ctacttaagc tcactgtgtt tttttttttt tttttgaaa cagaaattga gcaacttgaa     2820
gcatttggat ctcatggaca gctgtgagtt aagaaaaacc cctaattttg gtgatatgcc    2880
aaacttggag acactaattt tacacgggtg tgtgaatttg aagaggtcc atccctctct     2940 tggacagtgc agagtgctta cttatttgag tttggaaggt tgtcgcaaac ttaagaagct    3000
tccaaaattt gtctgcgtgg aatctcttga gactctcaat ctccttgaat gcacaagctt    3060
acaagaattt ccagaaatct gtggagatat gcatcgctta tcgacgctcg atgtaggatc    3120
cccctggata agaagcttac ccccatctct cagcggcctt agatatttgc aattgactga    3180
gtgtgcagtt cttgaaagta ttccggacgc cattcaaaat cttagatatc tcagtatttt    3240
agattgcaat aaacttgcaa cactgccaaa cagcctcttt gaatcacagc aattggaata    3300
tcttttaata caccgatgtt ctggattggt aaagctcccc ttatctcttg gagttcaaaa    3360
gattctccgt tggttaagta tagatggatg tgagaactta agaagcttc caagctcgat     3420 tcagatgaaa tcccttcaaa gtctctggat atctgattcc ccaaaattag acacatttcc    3480
agaaatcaat ggagatatgc attacttgga aatactgtct ctgaagtcta ctgggataag    3540
agaagtgcct tcatccattg ggaatctgag cggcctcact gatctaagtc ttacaggttg    3600
tgaagatctt ctaagtctac cagacagcct ctgcaatttg atgaaacttc gaagtcttta    3660
cctcgacggg tgcaaaaagc tagagaagct tccagaaaac attggtgatt tgcaagattt    3720
acataaactt gatgcgagcg atactgcaat ctcccaacca ccttcctcca tcactaagct    3780
tggcaaactg tggaagttac gattctcaca tgaaaaacaa cttcaatatt cctcaagttt    3840
tgtcttgaat caagtatcag gtttatcgtc cttgacatca cttgatctta ataatcacaa    3900
catattgagt ggacttcctg aggatttagg atctttgcag tctttggaaa aactgagtct    3960
aagtggaagc aatatttctt gtttaccaaa aagcttcaaa ggactcttac accttcagca    4020
```

```
tctgaatgta caattctgtc agaatcttaa taaattgccc ggagagctac ccccaaattt    4080
aaaggagcta tgtgtagatt atcatttagc cttaatgagc atcagagatc tcgtaattca    4140
ttatcctaag ctgtgtaggc ttgggatatc cgactgtgga gccgtctcaa gtgaacaagt    4200
taatgtgttc ctacaatatt ttatcaggac atgcatccag ttttttatct tatatatgaa    4260
atgttgaata ttctcgtcaa attgattgat ttctagtagt aataataatt tctattctat    4320
tgcatgcagt ttgactttct ccaaagagat tattttctca ttttttttcc tgatcaagtc    4380
agaatttcag agttgtttga ttatgatcgg tttacaaatc aaaagagat gtcaattgat     4440 ctgaacccat cttggtatac cgataaattc atgggttttt ggataagtta tggtcttact    4500
acactgaact acacaagatt agaagctaca ttggtctgca atctgaccc tgaaagaaaa     4560 tattccttga agtataacta ctttggacaa ttgtgtatcg agtctccttc catttgttgc    4620
ttctacatac catttgaaac actgtggaat gcttctggca taaagaagg gaagaatcca    4680 aatgattatt acatgttgga ggtatctaat aggtacagtc tggagaaaga acgatgctgg   4740
ggaattcgcc tggagtatga aaaggaggag gcaatgagtg atactggtcg tccaaaaaag   4800
aaaaggaagc aatgagtgat gcaaaggtcc ttgttttaca tcacaatatt taaatgttct   4860
ttatttcttt cttaaattcc gtactcaacc aaacacgtct cataaaattg tatggaaaga  4920
atatgttcta tattgttgat acaatttgta tatgaggggt ttgtatcgat gatagataga   4980 tgaattttt tttttttata atgttggttt ttgagtttga acaacttct ttacacttat     5040 aataaggtag atacgttgag tatcc                                         5065
```

<210> SEQ ID NO 11
<211> LENGTH: 7488
<212> TYPE: DNA
<213> ORGANISM: Artificial sequence
<220> FEATURE:
<223> OTHER INFORMATION: synthetic nucleic acid construct
<220> FEATURE:
<221> NAME/KEY: promoter
<222> LOCATION: (1)..(426)
<223> OTHER INFORMATION: CaMV 35S promoter
<220> FEATURE:
<221> NAME/KEY: 5'UTR
<222> LOCATION: (443)..(504)
<220> FEATURE:
<221> NAME/KEY: misc_feature
<222> LOCATION: (1539)..(1934)
<223> OTHER INFORMATION: CDS
<220> FEATURE:
<221> NAME/KEY: misc_feature
<222> LOCATION: (3286)..(4592)
<223> OTHER INFORMATION: CDS
<220> FEATURE:
<221> NAME/KEY: misc_feature
<222> LOCATION: (4676)..(5787)
<223> OTHER INFORMATION: CDS
<220> FEATURE:
<221> NAME/KEY: misc_feature
<222> LOCATION: (6271)..(6275)
<223> OTHER INFORMATION: CDS
<220> FEATURE:
<221> NAME/KEY: terminator
<222> LOCATION: (6775)..(7488)
<223> OTHER INFORMATION: OCS terminator

<400> SEQUENCE: 11

```
gtcaacatgg tggagcacga cactctggtc tactccaaaa atgtcaaaga tacagtctca     60
gaagatcaaa gggctattga gacttttcaa caaaggataa tttcgggaaa cctcctcgga   120
ttccattgcc cagctatctg tcacttcatc gaaaggacag tagaaaagga aggtggctcc   180
```

| | |
|---|---|
| tacaaatgcc atcattgcga taaaggaaag gctatcattc aagatctctc tgccgacagt | 240 |
| ggtcccaaag atggaccccc acccacgagg agcatcgtgg aaaaagaaga ggttccaacc | 300 |
| acgtctacaa agcaagtgga ttgatgtgac atctccactg acgtaaggga tgacgcacaa | 360 |
| tcccactatc cttcgcaaga cccttcctct atataaggaa gttcatttca tttggagagg | 420 |
| acacgctcga gtataagagc tcattttttac aacaattacc aacaacaaca aacaacaaac | 480 |
| aacattacaa ttacatttac aattatcgat acaagctgag gcttaatatg tcttgggaaa | 540 |
| atttgcatcg acttttcaat tttgtaatca tccctaaaat ttcgatacac aaactccagc | 600 |
| tcttcacact ggaacgcgaa ttccacaaaa ttttcatttg cttgcagaga ttcacagatg | 660 |
| aacctaacat gctagatgtc actcagaaag tccaaactct gtttgaagat gttgcattta | 720 |
| tcctttctcc actgtaccta actgacaact ttgatgtctg tgcctctgag gtgcaaaaca | 780 |
| agattttgtt aatcaagaag gaaataagag ccaaatactc cttttcctaaa atatcattac | 840 |
| aactttcagc cgagtttgtt agtgatatca tccattctgt gctagagaat attggtggtc | 900 |
| tagtgaagat tcatgatcca tattcacctc tttatgttcc cgaaacagta gaggaacata | 960 |
| tagaagatgt ttcaaaggaa ttgaatttgc tgctaatttt cgtctacttt gtttcagaga | 1020 |
| ggttcctaga gcatcagagc caacatcata ttattttctt cactcatgtt ttagctgtgt | 1080 |
| ctgtccacac atcaatgctt ctctggttgt atttaccaga cttggatcca gagcaaatga | 1140 |
| atgttatgct ttctgatttc ttacgaatga cgattaagcc gattcaacca tgcatccgca | 1200 |
| agatctatgt tgatgtcttg ctatctctaa agtcgacaat acaatcagga tggtatccca | 1260 |
| acatccgaaa tgaggatgca gttgacagcg aagggggtatt tttggagacc atcctacaca | 1320 |
| atttggtgga ggtaccaact aatagtaact ctagtcagag agttgctttg aaggatcact | 1380 |
| tggaaaccct tcaaaacatg ctcaaccttt tgagtgccaa tatcttccgt gtgccaataa | 1440 |
| aagatcttga atttcttctt tgagatatag agattgtggt tattgatgtt ggacttctgg | 1500 |
| tatactcatt atatgaagat gaggaggaga aggaagacat ggcaccagga ggagtgcaca | 1560 |
| ttacacaagt tcttgatttg tcaagcaaca ttcaacgtct aagcatagac atctacctca | 1620 |
| ccattcggaa ggcattccaa tctaatttgc ctaggattca tggactaggc tatgttgatt | 1680 |
| gccatttaaa caacctgaag aagttccaaa tcctccattc agattcacta gcttctgtca | 1740 |
| tggacaaact tcaatcaatt cagaaagaat ttgagagctt gcaaccttttt ctacaggctg | 1800 |
| ttgcagaagc gcgacacaat gaccttgatg caattcaaca ttgtgctaca caattgattg | 1860 |
| gcaaagcaca tgaggtagaa tacatagttg atgcttgtat aagggaagaa gctcctcaac | 1920 |
| tcccatcttg ttggtgagac tctgattccc cacactgtga ttctacctca ttttcccttc | 1980 |
| ccctaccatt ttttttaaaa aaatataaaa atttaaacta acaatacagt acaatataat | 2040 |
| tgatatcaac catcccaaac aaggtgcaac gggttgtgtg gtagctgtat gagaaacaaa | 2100 |
| ttatccatat gttaatttttc gtataattta tatgatgttt gataggtaga taaattataa | 2160 |
| cttaatataa tttataagat taacttttga ctcataagtt aaaaattata acttgtgatt | 2220 |
| ttttaacatt ttatcttaaa ctcaagtgct tataagtact ttaatagttt acctaaaatt | 2280 |
| aacacttcaa cagtcgttag ataaagtgta taagaataat gctaaataaa atgtattagt | 2340 |
| aatgcttgca tcaattatac atagattatt tttatgcatt gttcggtttg atgcattaaa | 2400 |
| aatttacaaa gatatgtttc actattatgg tggaaaagat ttaaagaaa aaaaaaagat | 2460 |
| tttgacaggc aattgagtga ttaaacatgc taatgcatgc atttaaaacg attgcattgc | 2520 |

```
gaatatttag aaatccatgg tattagcaat acagagttac acatagatta gaaaaaatta   2580
gcaaacaaag tactagtaat aggcaagggt aatgcatgca ttatttttc gaaataacga    2640 caactaaagg cgagaatgga taataagtag caaatagagc tcatagcata gagtctattc   2700
tggtaggcaa tcttgtgaag aaattgagtg gagcagatgg taggttgtga tggaaccatg   2760
gatgtcttaa cacataaaat ccagtgacta gagttgcaac tcgaaaaccc atgaaataga   2820
gaacaatgac agcaatcaag caggaaataa caaacagttt ggtcgctgta gggtctctcc   2880
atgacaccaa agagttcagc ctctccagtt gattagctat gtcaccagcc acattctgaa   2940
tacttccagc aatacttttc aaacgggtca taccttatcc gaacaatatc aattcgacgt   3000
gaagtaggga aagtatcaaa ctcctcgtcc agttcatcag gatgagcatc atcagcacaa   3060
gaaagacgaa tgtctatgaa gggaggatgc ctaggcctat atctataatt ccaaactacg   3120
attaaggaga gcgagaggaa aatggtaggc agaatacact ccggatatag aactagtatc   3180
aaatacaaga catggatcac aagagtcgta atgggatttt tccaactgca aatttgatca   3240
aaccatttcc taatagaatt tgagagtttg caaccttttc tacaggctgt tgcagaagcg   3300
cgacacaatg accttgacga aattcaacat tgtgcaacac aattgattgg caaagcacat   3360
gaggtagaat acatagttga tgcttgtata agggaagaag ctcctgtctg ctgcctcgag   3420
cattggatct tggatatcat ggaggatatt actcttatca gaagaggt agcagagatt     3480 cgtgaaaaga aaatggattt ggtagcattg aacactgtcc ctgttaatac atcaaatttg   3540
gcaaggtctc caatgatgaa tgaagaaatt attggttttg aggatgaaat agaaaagtta   3600
agagaccaac taataaaagg cacgaaaggg cgcgatgtta tatcagttgt tggtatgcca   3660
ggtctaggca agacaacttt ggcctacaga ctctactatg acaggttagt ctcttctcac   3720
ttcaacattg tgcacagtg ttgtgtgtct caagtatatt cacgtaagga cttgttaata   3780
gcaattttac gtgatgctat cagtgagaac tttgagtgta gagaaaaaca agctgatgaa   3840
ttagctgatc tgcttcgcaa aactttattt cccgaaagat atctcatcct tgttgatgat   3900
gtgtgggaaa ctagtgtgtg ggatgatcta ataggttctt tccatgatgc caataacgga   3960
agtagaatta ttctaacaac gcgaaatcat gaagttgcca tgtacactag atttcaaagt   4020
gatccgcttc cgcttcgtat gtttaacaat ggtgaaagtt gggagttact ccgaaaaaaa   4080
gtgtttggtg aagaaagttt ctctccactc taacagaaa ttgggcaaca aatagcaaaa    4140
aagtgtggtc aactgcctct ttcagttgtt ttggtggctg gtattctggc tgagatggag   4200
aagaaagtag aatgttggaa tcaactggcc aacaatttag gtccccacat tcatgaagac   4260
tcaagggccg ttatagaaca aagttatcag attttacct atcgtttgag accttgcttt    4320
ctttactttg gagcactttt agaggatagt gtgattagtg ttccaaagtt aacacagttg   4380
tggatctcag aaggattcgt aaaaagttgt gaaggcaaga acttggagga tatagcagaa   4440
ggctatttgg aaaatcttat tggaagaaat ctagtgatgg gaacgaagag gagttctcgt   4500
ggtaagatca aagcatgtcg cattcatgac ctattgcatg atttctgcaa ggagagagca   4560
aaggacgata tgcgtctcct atggcaaaaa tggtaatata ccaatcattg ctactctttt   4620
cacttatatt gacatttaat catataattt tactaatttc tgtatatatt tgtagggatc   4680
aaaatgccaa tccgtcttct cgcctttctg gtcacaagca actagctcac cgcatgtgca   4740
tttatggtga agggtatcgt gctggagatt ggagctcgtg cttgtcacat gttgtttcta   4800
taattttgca taacaatcgt ctttcagttg gcctcgactc tcacattttc cacggcgtaa   4860
agtttctaaa agtgttagat atggagttca ctagaattaa ttctttctca tttgatctag   4920
```

```
tctacctcag gtattttgct gcagaaactt cccgcttttc aaacaaagcc ggttgtcgcg    4980
aacttgaaac tctgaaatta aaatctctca gtgaagtgtc actacccatt acattctggg    5040
agatggataa attgagacat gtggatattt ccaattgcag cttcaccagt gaaattgcaa    5100
gggaattgat tgagaactcc aaagaccttc atgatctgca aactctatcc actccgtgct    5160
tttcttgtgc tcaggaagcg gaattgattt tgagaaaaac acctaatctt ctggaactga    5220
gatgcaaagt caagggtgtt gataactttg agtgctatgt attgaacttt ccagcacgca    5280
ttgaaacact caagattcat cttagctaca cacgtgacac taaaacaatc cccttctgca    5340
tctccgcgcc aactctcaca aacttgacac tgaagaactt ttacctacat tgtcagcatt    5400
tatcacaaat tggttcactt cagaaccttc aagtgctcag tctgaaaggt atttcctttg    5460
aaacttgtaa atgggaagtg cgtgatgacg agttccctca gctcaaagtc ttgaaattac    5520
attctggaaa agctcacttt gaagaatggt ctgtcgcgga tgatgccttt cctaaccttg    5580
aacacttggt tttgagggat tgcaaatttc ttaaggagat cccttcttgg tttgctgaaa    5640
tctcttctct gaagtccatt gaggtaagga attgcaatga aaatgttgac aagtcagcca    5700
gtgatataag ggaaacacaa gttgaagatt accagaactc caagttcgag gtctttatca    5760
ccagagagaa taacaagtca gattcaggta cgcaactcat aaaattcaac tatgaacagt    5820
cctaaactct gtgaattcat ttcttctgtt actctaactt cctttttaaa ggtaaaagtt    5880
cttgaattag caccaaggtt tgaaatacta ttgtgcacct tgactaattc tctaggtacc    5940
tactacctcc aaccgcacat gtactagata actgatgatc aaaagaaatc aactagtgac    6000
ttcaaaagag acccatgagg tctcaagttc aaatccagta gtgtcaaaaa cactatgcga    6060
tggtgggcag agttaccagg tacgtatgtt ggtaggaggt agcaggtacc cctagaatta    6120
ctcaaagtgc acacaagcta aaccaaatac catggttaat tattaaaaaa taaataaaaa    6180
atatgctctt actttctgtt tgggtatgtt gttgtagtag tacaacattt ttgagcaatt    6240
aacttattgg aaccttttct tttttaacag cataggaaga ctagagttgt atcaggagct    6300
gtttagaaga tcagtacgta atttttttg aagcttaatt aataaatcat gtacttttgg    6360
tcttgaatgt attgagtaac attgaatcca tgttgaacta tagttctatg agctatttat    6420
aatattttct agatttcttt tcttcttac gtatgtccat ttacactcat ctttcatgct    6480
atggaggaag aactttgacg taaccggtaa agttgttgtc atgtaactag aaggtcatgt    6540
acgagttcga catgtggaaa atacctcttg cagaaagcga gagcttagtc attaggctac    6600 cctattttg tactcgtttt gtattccttc caatgcttgc cactcaaacc ctatatccta    6660
tctcagggtc acgtcaagta gattccactt tagagataag ttttttatct taatggatca    6720
aaatagatta agactatcag aagttactta gtctcattct aaacctcagc gcttgtcctg    6780
ctttaatgag atatgcgaga agcctatgat cgcatgatat ttgctttcaa ttctgttgtg    6840
cacgttgtaa aaaacctgag catgtgtagc tcagatcctt accgccggtt tcggttcatt    6900
ctaatgaata tatcacccgt tactatcgta tttttatgaa taatattctc cgttcaattt    6960
actgattgta ccctactact tatatgtaca atattaaaat gaaaacaata tattgtgctg    7020
aataggttta tagcgacatc tatgatagag cgccacaata acaaacaatt gcgttttatt    7080
attacaaatc caattttaaa aaaagcggca gaaccggtca aacctaaaag actgattaca    7140
taaatcttat tcaaatttca aaagtgcccc agggggctagt atctacgaca caccgagcgg    7200
cgaactaata acgctcactg aagggaactc cggttccccg ccggcgcgca tgggtgagat    7260
```

```
tccttgaagt tgagtattgg ccgtccgctc taccgaaagt tacgggcacc attcaacccg    7320
gtccagcacg gcggccgggt aaccgacttg ctgccccgag aattatgcag cattttttttg   7380 gtgtatgtgg gccccaaatg aagtgcaggt caaaccttga cagtgacgac aaatcgttgg    7440
gcgggtccag ggcgaatttt gcgacaacat gtcgaggctc agcaggac                 7488
```

<210> SEQ ID NO 12
<211> LENGTH: 6232
<212> TYPE: DNA
<213> ORGANISM: Solanum stoloniferum

<400> SEQUENCE: 12

```
atgtcttggg aaaatttgca tcgactttc aattttgtaa tcatccctaa aatttcgata     60
cacaaactcc agctcttcac actggaacgc gaattccaca aaattttcat ttgcttgcag   120
agattcacag atgaacctaa catgctagat gtcactcaga aagtccaaac tctgtttgaa   180
gatgttgcat ttatccttc tccactgtac ctaactgaca ctttgatgt ctgtgcctct     240 gaggtgcaaa acaagatttt gttaatcaag aaggaaataa gagccaaata ctcctttcct   300
aaaatatcat tacaactttc agccgagttt gttagtgata tcatccattc tgtgctagag   360
aatattggtg gtctagtgaa gattcatgat ccatattcac ctcttatgt tcccgaaaca    420 gtagaggaac atatagaaga tgtttcaaag gaattgaatt tgctgctaat tttcgtctac   480
tttgtttcag agaggttcct agagcatcag agccaacatc atattatttt cttcactcat   540
gttttagctg tgtctgtcca cacatcaatg cttctctggt tgtatttacc agacttggat   600
ccagagcaaa tgaatgttat gctttctgat ttccttacgaa tgacgattaa gccgattcaa   660
ccatgcatcc gcaagatcta tgttgatgtc ttgctatctc taaagtcgac aatacaatca   720
ggatggtatc ccaacatccg aaatgaggat gcagttgaca gcgaagggt attttttggag   780 accatcctac acaatttggt ggaggtacca actaatagta actctagtca gagagttgct   840
ttgaaggatc acttggaaac ccttcaaaac atgctcaacc ttttgagtgc caatatcttc   900
cgtgtgccaa taaagatct tgaatttctt ctttgagata tagagattgt ggttattgat    960
gttggacttc tggtatactc attatatgaa gatgaggagg agaaggaaga catggcacca  1020
ggaggagtgc acattacaca agttcttgat ttgtcaagca acattcaacg tctaagcata  1080
gacatctacc tcaccattcg gaaggcattc caatctaatt tgcctaggat tcatggacta  1140
ggctatgttg attgccattt aaacaacctg aagaagttcc aaatcctcca ttcagattca  1200
ctagcttctg tcatggacaa acttcaatca attcagaaag aatttgagag cttgcaacct  1260
tttctacagg ctgttgcaga agcgcgacac aatgaccttg atgcaattca acattgtgct  1320
acacaattga ttggcaaagc acatgaggta gaatacatag ttgatgcttg tataagggaa  1380
gaagctcctc aactcccatc ttgttggtga gactctgatt ccccacactg tgattctacc  1440
tcattttccc ttccctacc attttttttta aaaaatata aaaatttaaa ctaacaatac    1500
agtacaatat aattgatatc aaccatccca aacaaggtgc aacgggttgt gtggtagctg  1560
tatgagaaac aaattatcca tatgttaatt ttcgtataat ttatatgatg tttgataggt  1620
agataaatta taacttaata taatttataa gattaacttt tgactcataa gttaaaaatt  1680
ataacttgtg attttttaac attttatctt aaactcaagt gcttataagt actttaatag  1740
tttacctaaa attaacactt caacagtcgt tagataaagt gtataagaat aatgctaaat  1800
aaaatgtatt agtaatgctt gcatcaatta tacatagatt atttttatgc attgttcggt  1860
ttgatgcatt aaaaatttac aaagatatgt ttcactatta tggtggaaaa gatttaaaag  1920
```

```
aaaaaaaaaa gattttgaca ggcaattgag tgattaaaca tgctaatgca tgcatttaaa   1980
acgattgcat tgcgaatatt tagaaatcca tggtattagc aatacagagt tacacataga   2040
ttagaaaaaa ttagcaaaca aagtactagt aataggcaag ggtaatgcat gcattatttt   2100
ttcgaaataa cgacaactaa aggcgagaat ggataataag tagcaaatag agctcatagc   2160
atagagtcta ttctggtagg caatcttgtg aagaaattga gtggagcaga tggtaggttg   2220
tgatggaacc atggatgtct taacacataa aatccagtga ctagagttgc aactcgaaaa   2280
cccatgaaat agagaacaat gacagcaatc aagcaggaaa taacaaacag tttggtcgct   2340
gtagggtctc tccatgacac caaagagttc agcctctcca gttgattagc tatgtcacca   2400
gccacattct gaatacttcc agcaatactt ttcaaacggg tcataccttc tccgaacaat   2460
atcaattcga cgtgaagtag ggaaagtatc aaactcctcg tccagttcat caggatgagc   2520
atcatcagca caagaaagac gaatgtctat gaagggagga tgcctaggcc tatatctata   2580
attccaaact acgattaagg agagcgagag gaaaatggta ggcagaatac actccggata   2640
tagaactagt atcaaataca agacatggat cacaagagtc gtaatgggat ttttccaact   2700
gcaaatttga tcaaaccatt tcctaataga atttgagagt ttgcaacctt ttctacaggc   2760
tgttgcagaa gcgcgacaca atgaccttga cgaaattcaa cattgtgcaa cacaattgat   2820
tggcaaagca catgaggtag aatacatagt tgatgcttgt ataagggaag aagctcctgt   2880
ctgctgcctc gagcattgga tcttggatat catggaggat attactctta tcagagaaga   2940
ggtagcagag attcgtgaaa agaaaatgga tttggtagca ttgaacactg tccctgttaa   3000
tacatcaaat ttggcaaggt ctccaatgat gaatgaagaa attattggtt tgaggatga    3060 aatagaaaag ttaagagacc aactaataaa aggcacgaaa gggcgcgatg ttatatcagt   3120
tgttggtatg ccaggtctag gcaagacaac tttggcctac agactctact atgacaggtt   3180
agtctcttct cacttcaaca ttcgtgcaca gtgttgtgtg tctcaagtat attcacgtaa   3240
ggacttgtta atagcaattt tacgtgatgc tatcagtgag aactttgagt gtagagaaaa   3300
acaagctgat gaattagctg atctgcttcg caaaacttta tttcccgaaa gatatctcat   3360
ccttgttgat gatgtgtggg aaactagtgt gtgggatgat ctaataggtt cttttccatga   3420 tgccaataac ggaagtagaa ttattctaac aacgcgaaat catgaagttg ccatgtacac   3480
tagatttcaa agtgatccgc ttccgcttcg tatgtttaac aatggtgaaa gttgggagtt   3540
actccgaaaa aaagtgtttg gtgaagaaag tttctctcca ctcctaacag aaattgggca   3600
acaaatagca aaaagtgtg gtcaactgcc tctttcagtt gttttggtgg ctggtattct   3660
ggctgagatg gagaagaaag tagaatgttg gaatcaactg gccaacaatt taggtcccca   3720
cattcatgaa gactcaaggg ccgttataga acaaagttat cagattttac cctatcgttt   3780
gagaccttgc tttctttact ttggagcact tttagaggat agtgtgatta gtgttccaaa   3840
gttaacacag ttgtggatct cagaaggatt cgtaaaaagt tgtgaaggca agaacttgga   3900
ggatatagca gaaggctatt tggaaaatct tattggaaga aatctagtga tgggaacgaa   3960
gaggagttct cgtggtaaga tcaaagcatg tcgcattcat gacctattgc atgatttctg   4020
caaggagaga gcaaaggacg atatgcgtct cctatggcaa aaatggtaat ataccaatca   4080
ttgctactct tttcacttat attgacattt aatcatataa ttttactaat ttctgtatat   4140
atttgtaggg atcaaaatgc caatccgtct tctcgccttt ctggtcacaa gcaactagct   4200
caccgcatgt gcatttatgg tgaagggtat cgtgctggag attggagctc gtgcttgtca   4260
```

| | |
|---|---|
| catgttgttt ctataatttt gcataacaat cgtctttcag ttggcctcga ctctcacatt | 4320 |
| ttccacggcg taaagtttct aaaagtgtta gatatggagt tcactagaat taattctttc | 4380 |
| tcatttgatc tagtctacct caggtatttt gctgcagaaa cttcccgctt ttcaaacaaa | 4440 |
| gccggttgtc gcgaacttga aactctgaaa ttaaaatctc tcagtgaagt gtcactaccc | 4500 |
| attacattct gggagatgga taaattgaga catgtggata tttccaattg cagcttcacc | 4560 |
| agtgaaattg caagggaatt gattgagaac tccaaagacc ttcatgatct gcaaactcta | 4620 |
| tccactccgt gcttttcttg tgctcaggaa gcggaattga ttttgagaaa acacctaat | 4680 |
| cttctggaac tgagatgcaa agtcaagggg gttgataact ttgagtgcta tgtattgaac | 4740 |
| tttccagcac gcattgaaac actcaagatt catcttagct acacacgtga cactaaaaca | 4800 |
| atcccttct gcatctccgc gccaactctc acaaacttga cactgaagaa ctttttaccta | 4860 |
| cattgtcagc atttatcaca aattggttca cttcagaacc ttcaagtgct cagtctgaaa | 4920 |
| ggtatttcct ttgaaacttg taaatgggaa gtgcgtgatg acgagttccc tcagctcaaa | 4980 |
| gtcttgaaat tacattctgg aaaagctcac tttgaagaat ggtctgtcgc ggatgatgcc | 5040 |
| tttcctaacc ttgaacactt ggttttgagg gattgcaaat ttcttaagga gatcccttct | 5100 |
| tggtttgctg aaatctcttc tctgaagtcc attgaggtaa ggaattgcaa tgaaaatgtt | 5160 |
| gacaagtcag ccagtgatat aagggaaaca caagttgaag attaccagaa ctccaagttc | 5220 |
| gaggtctttta tcaccagaga gaataacaag tcagattcag gtacgcaact cataaaattc | 5280 |
| aactatgaac agtcctaaac tctgtgaatt catttcttct gttactctaa cttcctttt | 5340 |
| aaaggtaaaa gttcttgaat tagcaccaag gtttgaaata ctattgtgca ccttgactaa | 5400 |
| ttctctaggt acctactacc tccaaccgca catgtactag ataactgatg atcaaaagaa | 5460 |
| atcaactagt gacttcaaaa gagacccatg aggtctcaag ttcaaatcca gtagtgtcaa | 5520 |
| aaacactatg cgatggtggg cagagttacc aggtacgtat gttggtagga ggtagcaggt | 5580 |
| acccctagaa ttactcaaag tgcacacaag ctaaaccaaa taccatggtt aattattaaa | 5640 |
| aaataaataa aaaatatgct cttactttct gtttgggtat gttgttgtag tagtacaaca | 5700 |
| ttttttgagca attaacttat tggaaccttt tcttttttaa cagcatagga agactagagt | 5760 |
| tgtatcagga gctgtttaga agatcagtac gtaattttt ttgaagctta attaataaat | 5820 |
| catgtacttt tggtcttgaa tgtattgagt aacattgaat ccatgttgaa ctatagttct | 5880 |
| atgagctatt tataatattt tctagatttc ttttttcttct tacgtatgtc catttacact | 5940 |
| catctttcat gctatggagg aagaactttg acgtaaccgg taaagttgtt gtcatgtaac | 6000 |
| tagaaggtca tgtacgagtt cgacatgtgg aaaatacctc ttgcagaaag cgagagctta | 6060 |
| gtcattaggc tacccatttt ttgtactcgt tttgtattcc ttccaatgct tgccactcaa | 6120 |
| accctatatc ctatctcagg gtcacgtcaa gtagattcca ctttagagat aagttttta | 6180 |
| tcttaatgga tcaaaataga ttaagactat cagaagttac ttagtctcat tc | 6232 |

<210> SEQ ID NO 13
<211> LENGTH: 7488
<212> TYPE: DNA
<213> ORGANISM: Solanum stoloniferum

<400> SEQUENCE: 13

| | |
|---|---|
| ccaaacctttt gttcgaggct atcccaaagc tccttagctg tgttggaata gatgacacta | 60 |
| tctccaatct ctttggacaa tgagttgagt aaccaagagg ttaccatgtc attacaacaa | 120 |
| ttccattgag aagaatcaga agcatcgaaa actggtgctt aacaggttcc attgatgaag | 180 |

```
cctagcttcc tcttaactga aagagctatc aagatcgatc tcctctaacc aggaaaacct    240
cgtccatcaa ccacagtgct tatgaggttc attctaggag aatcagaggg gtgaagataa    300
taagggtgac tggagtccat agcagatgct gcaggtgcaa caatggttcc aggattgttg    360
gagggtgatg aagaatctct cattgtagat gatgagtgaa tgtgaattgg atcgagctta    420
ctgctttgat accatgttat aaatgtagga gacgtttgtg gaaattttct gataatctat    480
tgatcatcat cttcaatcta tatatacaag tattctgtgc aagaaaatac aaaaaaatca    540
cagctgtaca cttgtctaaa tcttgtagaa atattctaac aacctaacta attttattcc    600
atcctatgtt gatatagtgt gctgctcacg tgctcttctt catttctttc attctgcaag    660
atgagtggaa attatgtttg ccaacaaaaa ttcaaagtta agggtaaggt tgcgtacaca    720
tcatccgttt gtgaaatttt actagatatg ttgtccttga atcattttct gtgattgtta    780
taacttacgc gtacattagc ataaggtgga ttttcatttt taattcaaaa tatctaaatg    840
attcggcagt cacatagatt ggtcaaatag ttgtggtact aacatgttaa gtttagcaat    900
ttaattatcg atgaattatt atacatttga accaagaaaa aagagagttg ttatacatat    960
taaattgaat tatttaatgg ttgagtaaat tttaatttt gttaaaaaga ggataatttt      1020
atatgtaaaa ggtaattttg atttgaagag acatttttaa tttgataatt aatgtattaa    1080
aaataatttg gaaggataga taatttatta tcattctcaa caagttagct tttgggtgtg    1140
gttctcccag gtcagtcttt cttttctgct ttttctgtgt tttcttctaa attgttacga    1200
aatttttctt caatttctta ggtagggcaa cgaatttata tcaatttaca caaaggtatc    1260
aatttctgtt catttgttta atttgtcagt gcaatactga aaaaaggtac attttatgt     1320 catgaattag gaagatgata acaagtttcc tatagagact gaaaaaaggt aaagtcttta    1380
ctctttgtga acacaataag tttgctggaa atttctaaga agttggtccc cattgaacaa    1440
tgatcctgca tttgaacttc attagaggtt ggacccattt gatgggtgac cgaaaccttg    1500
gaagtcctcg tattgcatct cttcttatgt cattaatttc gatcatatta caataaagtg    1560
ttttaaaaag taaaaatgta atgactttaa tttctcacaa taatgaatac ctaggataca    1620
gttttatgat ttgaaatagg aagatgttaa gaagttctca taaaaggtgt ggcctagtgg    1680
tcaatgaagt ggttgagagc catgaggtct caggttcaac ttccaacgga gacaaaaata    1740
ttaggtaatt cttcccatct atcctagccc tagccctggt ggacagagtc atctggtact    1800
tgctgttggt gaatggaaaa gatagttgtt tttagaagat tattagtaaa cgtactaatt    1860
gatttatcaa cataactgat gggattatga agtggcttgt ggagttagtc gagaagtgct    1920
caagctgacc tagatactaa ctactaataa gaaaagaaca attgatgtga gtcaccatta    1980
gttgagccat tttctctaga ggaggaataa ttcaaagatg ctacgagaa gattcaagat      2040 tggtgggatg aatttgctaa tatgaaagca tgatgtaaaa agaactagta agtaaacttt    2100
cttttctctt tgtgtttgttg gtggggcctt tcataagaag ttggacccat tcacaataat    2160
gcatgttgca gacagagtgt ggaaaaatgt atataactac aaatatgtgg tgctaagaag    2220
acttcatatc agatacgcgt ctttagcaat attcttcaac aatgtctcat gcttcttctt    2280
ccaaagtttg caagtacgat atcttttga gtttagagg tgaagataca cgtagaaact     2340
tcgtgagtca tctttataat gctttagaac agagaggact ccatgctttc aaagacgatg    2400
agcggttgga agcaggaaaa tcaatttctg ctgaactttt aaaagccata gaagaggcca    2460
gattcgctgt cgtaatattt tcaaaaagct atgcatcgtc aagatggtgt ttagaggagc    2520
```

```
ttgcacacat cataaagtgt aaaaaggaat tggagcagat tgtgattcca gtcttctatg    2580
atgtgagtcc atcagatgta cgccatcaaa atcccccttt cgctgtttca ttttcccaac    2640
atgaggaaaa atgcaaagat gatatggaga aggttcaaag atggaggggc gcatttgcgg    2700
aggcagggaa aatatcaggc tatcatttac taaatttcaa gtaagccttc ttttttcttt    2760
tttttcgggt ttctctttat caagaggaaa aaggaccaaa cttttagcca aaaaggaaca    2820
aagatcctag gaaaacagaa acgtatatga ttgtttgatg atgtaattag atttaaaaat    2880
gttataattc ataattgaca ttattatgtg tttgttttag atattagtct atgacaagtc    2940
tttgcttttc tatttattta ctttgagatt attttccact gtaacgtagg gatgaggcca    3000
agtgcgtcaa gaaactagtt gatgacatat ttcctaagtc acttcaaatt atttcacctt    3060
tcccggaaag cttagtgggt atgaaatctc aggttgagaa agtaacctca ttattagata    3120
tggaatcaaa cgatgttcgc tctattggta tttggggtat gggcggcatc ggcaaaacag    3180
aaattgcaaa tgttctacat caaagatacc gccatcaatt tgacgctgat tgttttcttg    3240
gtgatgttgg aaaacttcat cagaaaaatg gactaacgtg gctacaacaa gtcgtcattt    3300
gcaagctctt gggtgaaaaa ttgactctaa ctagtgagca tgaagggatg aatattttaa    3360
agaatatgct tcgctggaag aaagttctgt tcaccatcga tgcgtaaaac catcaagaac    3420
agttggaatt tttggttgga gagccagagt ggtttggtag gggtagcaga attattttaa    3480
cagcaagaga caagcaccta ttaatcagtc acgttgggga taatgtgtat gaagtccaac    3540
tattatctga gaatgaagca cttgaattgt tcagtagaca tgcttttaga gaaagatcac    3600
caaaagaaga ttttatggaa cttttcaagac aagtggtgaa gcatgctggt ggactccctt    3660
tagctcttaa agttttgggt tcttcatttt acggacgaga caaaaagcac tggagacaca    3720
taattgatcg gctgaagaga atccctcaca aggatattct aggaaagctt aggcttagtt    3780
ttgatggtct ggacaaagat gagaaggaat tatttctgga tattgtattt ctagagattg    3840
catgcttgag tggatatgat tttaatattt atgtggaaca agtacagaga tatgtgagtc    3900 gtggttact aatttattac cttattgaaa aatctctgtt atccatcgac tggagtaata    3960
gtattgtgat tcataatatg ataagagaaa tgggagaaaa tgtcatacgg gaagagtacg    4020
ctaacagcag aatatggctt cccgaggaga tttgtgatct ttttaaaggg aagttggtaa    4080
gcaatattta acgtaattaa taatttcata agctcttagt tctgttaatt tattttgttt    4140 cattttatt tgttagtcat taaatattgt ttcattttt acagataaca gaaaaggtgg    4200
aaagcctatg tattccaaaa gagtactatt ttgaagatga tcttgtcaat tatagcaata    4260
ttttcaagag gatgcaaagc ttaaaaacac tcatagttgg tgatggaact tttagcacaa    4320
actgcactat cacttatctt ccttccagcc tgcggttcat tgattggaaa gggtatcctt    4380
caatttcatt gccagagagc tttgaaccat cacagcttgt ggtgctttgt ttatataaaa    4440
gtaggcttgt tgaactttgg ccaatatcaa aggtaacact ctcttacaaa tattagacat    4500
caactggagt tgttgcaaag ttcttgtaca gaataatgga ataataattc tgaacaaata    4560
gttgtaatta tagaatatca tgtatataat gaggttgaaa taaatgtttt gataggccaa    4620
tgcatgtaaa ttaatccatc catgattaa atgctacttt aaataaatgt tctgatatac    4680
acaattaaca ccaaattttt atttattttt ggttatcagt cacggcataa ggcccataaa    4740
tatttttact tttccaatat tttaaaaaat taaatcttat aaaaagttac gatattaaag    4800
aggttttgtt tcattatga aattaaaaga aagaaaatat atatttggat tttaagacaa    4860
ttatgtatct caaaagttct tttccggatt agctaccgcc tttagtgatc ataacaacct    4920
```

| | | | | |
|---|---|---|---|---|
| tatcttctct | ttatcttttt | ttcctacaaa | atatttctat | taggagtact acttaagctc | 4980 |
| actgtgtttt | tttttttttt | ttttgaaaca | gaaattgagc | aacttgaagc atttggatct | 5040 |
| catggacagc | tgtgagttaa | gaaaaacccc | taattttggt | gatatgccaa acttggagac | 5100 |
| actaatttta | cacgggtgtg | tgaatttgga | agaggtccat | ccctctcttg gacagtgcag | 5160 |
| agtgcttact | tatttgagtt | tggaaggttg | tcgcaaactt | aagaagcttc caaaatttgt | 5220 |
| ctgcgtggaa | tctcttgaga | ctctcaatct | ccttgaatgc | acaagcttac aagaatttcc | 5280 |
| agaaatctgt | ggagatatgc | atcgcttatc | gacgctcgat | gtaggatccc cctggataag | 5340 |
| aagcttaccc | ccatctctca | gcggccttag | atatttgcaa | ttgactgagt gtgcagttct | 5400 |
| tgaaagtatt | ccggacgcca | ttcaaaatct | tagatatctc | agtattttag attgcaataa | 5460 |
| acttgcaaca | ctgccaaaca | gcctctttga | atcacagcaa | ttggaatatc ttttaataca | 5520 |
| ccgatgttct | ggattggtaa | agctccccct | atctcttgga | gttcaaaaga ttctccgttg | 5580 |
| gttaagtata | gatggatgtg | agaacttaaa | gaagcttcca | agctcgattc agatgaaatc | 5640 |
| ccttcaaagt | ctctggatat | ctgattcccc | aaaattagac | acatttccag aaatcaatgg | 5700 |
| agatatgcat | tacttggaaa | tactgtctct | gaagtctact | gggataagag aagtgccttc | 5760 |
| atccattggg | aatctgagcg | gcctcactga | tctaagtctt | acaggttgtg aagatcttct | 5820 |
| aagtctacca | gacagcctct | gcaatttgat | gaaacttcga | agtctttacc tcgacgggtg | 5880 |
| caaaaagcta | gagaagcttc | cagaaaacat | tggtgatttg | caagatttac ataaacttga | 5940 |
| tgcgagcgat | actgcaatct | cccaaccacc | ttcctccatc | actaagcttg gcaaactgtg | 6000 |
| gaagttacga | ttctcacatg | aaaaacaact | tcaatattcc | tcaagttttg tcttgaatca | 6060 |
| agtatcaggt | ttatcgtcct | tgacatcact | tgatcttaat | aatcacaaca tattgagtgg | 6120 |
| acttcctgag | gatttaggat | ctttgcagtc | tttggaaaaa | ctgagtctaa gtggaagcaa | 6180 |
| tatttcttgt | ttaccaaaaa | gcttcaaagg | actcttacac | cttcagcatc tgaatgtaca | 6240 |
| attctgtcag | aatcttaata | aattgcccgg | agagctaccc | ccaaatttaa aggagctatg | 6300 |
| tgtagattat | catttagcct | taatgagcat | cagagatctc | gtaattcatt atcctaagct | 6360 |
| gtgtaggctt | gggatatccg | actgtggagc | cgtctcaagt | gaacaagtta atgtgttcct | 6420 |
| acaatatttt | atcaggacat | gcatccaggt | ttttatctta | tatatgaaat gttgaatatt | 6480 |
| ctcgtcaaat | tgattgattt | ctagtagtaa | taataatttc | tattctattg catgcagttt | 6540 |
| gactttctcc | aaagagatta | ttttctcatt | ttttttcctg | atcaagtcag aatttcagag | 6600 |
| ttgtttgatt | atgatcggtt | tacaaatcaa | aaagagatgt | caattgatct gaacccatct | 6660 |
| tggtataccg | ataaattcat | gggtttttgg | ataagttatg | gtcttactac actgaactac | 6720 |
| acaagattag | aagctacatt | ggtctgcaaa | tctgaccctg | aaagaaaata ttccttgaag | 6780 |
| tataactact | ttggacaatt | gtgtatcgag | tctccttcca | tttgttgctt ctacatacca | 6840 |
| tttgaaacac | tgtggaatgc | ttctggcaat | aaagaaggga | agaatccaaa tgattattac | 6900 |
| atgttggagg | tatctaatag | gtacagtctg | gagaaagaac | gatgctgggg aattcgcctg | 6960 |
| gagtatgaaa | aggaggaggc | aatgagtgat | actggtcgtc | caaaaaagaa aaggaagcaa | 7020 |
| tgagtgatgc | aaaggtcctt | gttttacatc | acaatattta | aatgttcttt atttctttct | 7080 |
| taaattccgt | actcaaccaa | acacgtctca | taaaattgta | tggaaagaat atgttctata | 7140 |
| ttgttgatac | aatttgtata | tgagggggttt | gtatcgatga | tagatagatg aatttttttt | 7200 |
| tttttataat | gttggttttt | gagtttgaaa | caacttcttt | acacttataa taaggtagat | 7260 |

```
                                                 -continued
acgttgagta tccaacatcc tttcaagatt tcactagata tgttgttgtt tgagtcattt    7320
tctatgtgat tgttataact tacgcatgag catatatcta agatattttg caaataaaat    7380
attatctata aagatagttt caaaattcga ttccataaac tttgatcaag gaagaaaatg    7440
tatatataat aatcaatttt gatgattgct caactttttc tctggccc                7488
```